(12) United States Patent
Alvaro et al.

(10) Patent No.: US 8,633,214 B2
(45) Date of Patent: Jan. 21, 2014

(54) SPIRO (PIPERIDINE-4,2'-PYRROLIDINE)-1-(3,5-TRIFLUOROMETHYLPHENYL) METHYLCARBOXAMIDES AS NK1 TACHIKYNIN RECEPTOR ANTAGONISTS

(71) Applicant: NeRRe Therapeutics Limited, Stevenage (GB)

(72) Inventors: Giuseppe Alvaro, Verona (IT); Emiliano Castiglioni, Verona (IT); Agostino Marasco, Verona (IT)

(73) Assignee: Nerre Therapeutics Limited, London (GB)

( * ) Notice: Subject to any disclaimer, the term of this patent is extended or adjusted under 35 U.S.C. 154(b) by 0 days.

(21) Appl. No.: 13/682,889

(22) Filed: Nov. 21, 2012

(65) Prior Publication Data

US 2013/0123250 A1 May 16, 2013

Related U.S. Application Data

(63) Continuation of application No. 12/989,699, filed on Oct. 26, 2010, now Pat. No. 8,367,692.

(30) Foreign Application Priority Data

May 1, 2008 (GB) .................................. 0808030.1
Apr. 29, 2009 (WO) .................. PCT/EP2009/055190

(51) Int. Cl.
*C07D 401/04* (2006.01)
*A61K 31/438* (2006.01)

(52) U.S. Cl.
USPC ............................................ 514/278; 546/17

(58) Field of Classification Search
USPC ...................................... 546/17, 18; 514/278
See application file for complete search history.

(56) References Cited

U.S. PATENT DOCUMENTS 6,013,652 A 1/2000 Maccoss et al.
6,329,401 B1 12/2001 Mendel et al.

FOREIGN PATENT DOCUMENTS

WO 9429309 12/1994
WO 01/30348 5/2001

OTHER PUBLICATIONS

Duffy, Potential therapeutic targets for neurokinin-1 receptor antagonists, Expert Opinion Emerg Drugs 9(1): 9-21 (2004).
Andersen, Monica L. et al. "Sleep disturbance induced by substance P in mice." *Behavioural Brian Research* 167 (2006) pp. 212-218.
Zhang, Gongliang et. al. "Substance P promotes sleep in the ventrolateral preoptic area of rats." *Brain Research* 1028 (2004) pp. 225-232.

*Primary Examiner* — Rita Desai
(74) *Attorney, Agent, or Firm* — Steinfl & Bruno LLP

(57) ABSTRACT

Compounds of formula (I) or pharmaceutically acceptable salts thereof

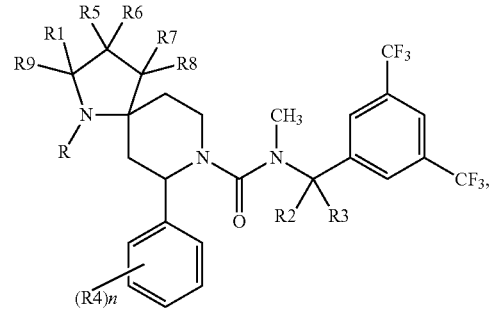

processes for their preparation, compositions containing them, and uses thereof in the treatment of diseases and conditions for which antagonism of NK1 is beneficial.

6 Claims, No Drawings

SPIRO (PIPERIDINE-4,2'-PYRROLIDINE)-1-(3,5-TRIFLUOROMETHYLPHENYL) METHYLCARBOXAMIDES AS NK1 TACHIKYNIN RECEPTOR ANTAGONISTS

This application is filed pursuant to 35 USC 111 (a) as a United States 5 Continuation Application of U.S. National Phase application Ser. No. 12/989,699 filed Oct. 26, 2010, which claims priority from PCT/EP2009/055190 filed Apr. 29, 2009, which claims priority from GB 0808030.1 filed May 1, 2008 in the United Kingdom, all of which are incorporated herein in their entirety.

FIELD OF THE INVENTION

The present invention relates to novel spiro bicyclic compounds having pharmacological activity, to processes for their preparation, to compositions containing them and to their medical uses.

DESCRIPTION OF THE INVENTION

The present invention provides, in a first aspect, a compound of formula (I) or a pharmaceutically acceptable salt thereof,

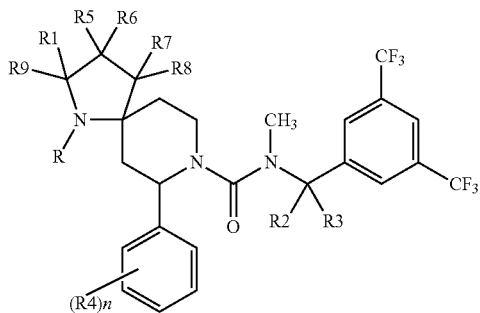

(I)

wherein
R is hydrogen or $C_{1-4}$ alkyl;
$R_1$ is hydrogen, $C_{1-4}$ alkyl, C(O)OH, C(O)NH$_2$ or ($C_{1-4}$ alkylene)$R_{10}$;
$R_2$ and $R_3$ are independently hydrogen, $C_{1-4}$ alkyl or $R_2$ together with $R_3$ and together with the carbon atom to which they are attached form a $C_{3-8}$ cycloalkyl group;
$R_4$ is $C_{1-4}$ alkyl, $C_{1-4}$ alkoxy or halogen;
$R_5$ and $R_7$ are independently hydrogen, hydroxy, halogen, C(O)NH$_2$, C(O)OH or ($C_{1-4}$ alkylene) $R_{10}$;
$R_6$ and $R_8$ are independently hydrogen or halogen;
$R_9$ is hydrogen, ($C_{1-4}$ alkylene)$R_{10}$, C(O)NH$_2$, C(O)OH or $R_9$ together with R form a 6 membered heterocyclic ring optionally containing a further heteroatom selected from oxygen, sulphur or nitrogen;
$R_{10}$ is hydrogen, halogen, hydroxy, C(O)NH$_2$, C(O)NH(C$_{1-4}$ alkyl), C(O)N(C$_{1-4}$ alkyl)$_2$ or C(O)OH;
n is 0, 1 or 2.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a pharmaceutically acceptable anion or cation. Suitably pharmaceutically acceptable salts of the compound of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesutfonic, acids; base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

The invention includes within its scope all possible stoichiometric and non-stoichiometric forms of the salts of the compounds of formula (I).

The compounds of formula (I) can exist as zwitterions.

Compounds of formula (I) may be obtained as crystalline forms. It is to be understood that these crystalline forms or a mixture thereof are encompassed within the scope of the invention.

Furthermore, some of the crystalline forms of the compounds of structure (I) may exist as polymorphs, which are included in the present invention.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Salts, solvates and hydrates of compounds of formula (I) therefore form an aspect of the invention.

Hereinafter, compounds of formula (I), their pharmaceutically acceptable salts, solvates, hydrates and crystalline forms thereof defined in any aspect of the invention (except intermediate compounds in chemical processes) are referred to as "the compounds of the invention".

The subject invention also includes isotopically-labelled compounds, which are identical to those recited in formula (I) but for the fact that one or more atoms are replaced by an atom having an atomic mass or mass number different from the atomic mass or mass number usually found in nature. Examples of isotopes that can be incorporated into compounds of the invention or pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the invention that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances.

Isotopically labelled compounds of the invention can generally be prepared by carrying out the procedures disclosed in the Schemes and/or in the Examples below, by substituting a readily available isotopically labelled reagent for a non-isotopically labelled reagent.

It will be appreciated by those skilled in the art that the compounds of formula (I) contain at least two chiral centres (namely the carbon atom shown as * in the formulae from (1a) to (1d)).

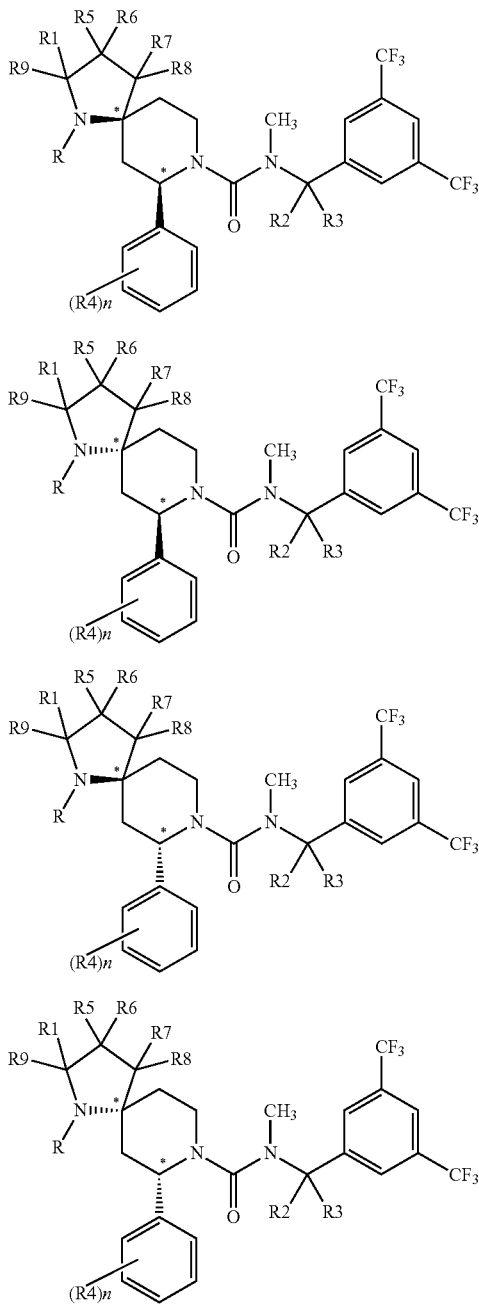

The wedge shaped bond indicates that the bond is above the plane of the paper and it is referred to as β configuration. The broken bond indicates that the bond is below the plane of the paper and is in the α configuration.

Further asymmetric carbon atoms are possible in the compounds of formula (I), such as when $R_2$ and $R_3$, $R_1$ and $R_9$, $R_5$ and $R_6$, $R_7$ and $R_8$ are not the same group.

It is to be understood that all stereoisomeric forms, including all enantiomers, diastereoisomers and all mixtures thereof, including racemates, are encompassed within the scope of the present invention and the reference to compounds of formula (I) includes all stereoisomeric forms unless otherwise stated.

The term 'halogen' as used herein refers to a fluorine, chlorine, bromine or iodine atom.

The term '$C_{1-4}$ alkyl' as used herein as a group or a part of the group refers to a linear or branched saturated hydrocarbon group containing from 1 to 4 carbon atoms. Examples of such groups include methyl, ethyl, n-propyl, isopropyl, n-butyl, isobutyl, sec-butyl, tert butyl, and the like.

The term 'C1-4 alkylene' as used herein refers to a linear or branched saturated hydrocarbon linker group containing from 1 to 4 carbon atoms. Examples of such groups include methylene and ethylene and the like.

The term '$C_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

Examples of a 6-heterocyclic ring optionally containing a further heteroatom selected from oxygen, sulphur or nitrogen include piperidinyl, piperazinyl, morpholinyl, thiomorpholinyl, and the like.

In one embodiment, the invention provides a compound having formula (IA) or a pharmaceutically acceptable salt thereof:

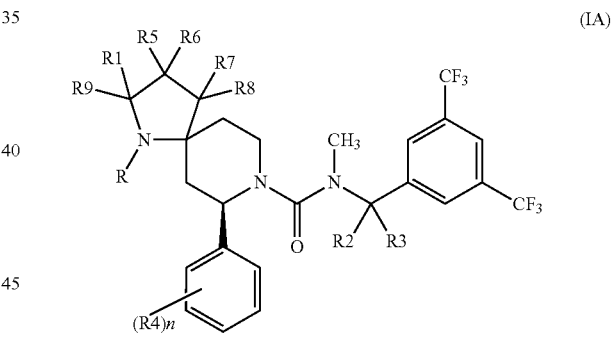

wherein
R is hydrogen or $C_{1-4}$ alkyl;
$R_1$ is hydrogen, $C_{1-4}$ alkyl, C(O)OH, C(O)NH$_2$ or ($C_{1-4}$ alkylene)$R_{10}$;
$R_2$ and $R_3$ are independently hydrogen, $C_{1-4}$ alkyl or $R_2$ together with $R_3$ and together with the carbon atom to which they are attached form a $C_{3-8}$ cycloalkyl group;
$R_4$ is $C_{1-4}$ alkyl, $C_{1-4}$ alkoxy or halogen;
$R_5$ and $R_7$ are independently hydrogen, hydroxy, halogen, C(O)NH$_2$, C(O)OH or ($C_{1-4}$ alkylene) $R_{10}$;
$R_6$ and $R_8$ are independently hydrogen or halogen;
$R_9$ is hydrogen, ($C_{1-4}$ alkylene)$R_{10}$, C(O)NH$_2$, C(O)OH or $R_9$ together with R form a 6 membered heterocyclic ring optionally containing a further heteroatom selected from oxygen, sulphur or nitrogen;
$R_{10}$ is hydrogen, halogen, hydroxy, C(O)NH$_2$, C(O)NH($C_{1-4}$ alkyl), C(O)N($C_{1-4}$ alkyl)$_2$ or C(O)OH;
n is 0, 1 or 2.

In one embodiment of the invention, R is hydrogen.

In one embodiment of the invention, $R_1$ is hydrogen or methyl.

In one embodiment of the invention, $R_9$ is hydrogen, C(O)NH$_2$, CH$_2$OH, or $R_9$ together with R form a morpholine ring.

In one embodiment of the invention $R_2$ and $R_3$ are independently hydrogen or methyl.

In a further embodiment of the invention $R_4$ is independently methyl or fluorine and n is 2.

In one embodiment of the invention, R, $R_1$, $R_5$, $R_6$, $R_7$, $R_8$ and $R_9$ are hydrogen.

In one embodiment of the invention, $R_9$ is hydrogen, C(O)NH$_2$, CH$_2$OH or $R_9$ together with R form a morpholine ring.

In a further embodiment of the invention, $R_9$ is C(O)NH$_2$, CH$_2$OH, or $R_9$ together with R form morpholine and R, $R_1$, $R_5$, $R_6$, $R_7$, $R_8$ are hydrogen.

In a further embodiment of the invention, R, $R_5$, $R_6$, $R_7$, $R_8$ are hydrogen, $R_9$ is C(O)NH$_2$, CH$_2$OH or $R_9$ together with R form a morpholine ring and $R_1$ is methyl.

In a yet further alternative embodiment, R, $R_1$, $R_5$, $R_6$, $R_8$, $R_9$ are hydrogen and $R_7$ is C(O)OH or CH$_2$(OH).

In a yet further alternative embodiment, R, $R_1$, $R_6$, $R_7$, $R_8$, $R_9$ are hydrogen and $R_5$ is C(O)OH or CH$_2$(OH).

In a yet further alternative embodiment, R is hydrogen, $R_1$ is hydrogen or methyl, $R_2$ and $R_3$ are independently hydrogen or methyl, $R_4$ is independently methyl or fluorine and n is 2, $R_5$ is hydrogen or C(O)OH, $R_6$ is hydrogen, $R_7$ is hydrogen or C(O)OH, $R_8$ and $R_9$ is C(O)NH$_2$, CH$_2$OH or $R_9$ together with R form a morpholine ring.

Compounds according to the invention include examples 1-37 as shown below, or a pharmaceutically acceptable salt thereof.

In one embodiment, the invention provides a compound selected from the group consisting of:

(5R,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (diastereoisomer 1);

(5R,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (diastereoisomer 2);

(2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;

(2S,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;

(2R,5S,7R)-N$^8$-{[3,5-bis(trifluoromethyl)phenyl]methyl}-7-(4-fluoro-2-methylphenyl)-N$^8$-methyl-1,8-diazaspiro[4.5]decane-2,8-dicarboxamide;

(2S,5S,7R)-N$^8$-{[3,5-bis(trifluoromethyl)phenyl]methyl}-7-(4-fluoro-2-methylphenyl)-N$^8$-methyl-1,8-diazaspiro[4.5]decane-2,8-dicarboxamide;

(2R,5S,7R)-N$^8$-{(1S)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;

(2S,5S,7R)-N$^8$-{(1S)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;

sodium (5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-3-carboxylate;

lithium (4S,5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-4-carboxylate;

(5S,7R)-N-{(1R)-1-[3,5-bis(trifluoromethyl)phenyl]ethyl}-7-(4-fluoro-2-methylphenyl)-N-methyl-1,8-diazaspiro[4.5]decane-8-carboxamide;

(2R,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide;

(2S,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide;

(2S,5S,7R)-N$^8$-{(1R)-1-[3,5-bis(trifluoromethyl)phenyl]ethyl}-7-(4-fluoro-2-methylphenyl)-N$^8$,2-dimethyl-1,8-diazaspiro[4.5]decane-2,8-dicarboxamide;

(2R,5S,7R)-N$^8$-{(1R)-1-[3,5-bis(trifluoromethyl)phenyl]ethyl}-7-(4-fluoro-2-methylphenyl)-N$^8$,2-dimethyl-1,8-diazaspiro[4.5]decane-2,8-dicarboxamide;

(2R,4S,8a'R)-N-{(1R)-1-[3,5-bis(trifluoromethyl)phenyl]ethyl}-2-(4-fluoro-2-methylphenyl)-N,8a'-dimethyl-hexahydro-1H-spiro[piperidine-4,6'-pyrrolo[2,1-c][1,4]oxazine]-1-carboxamide;

(2R,4S,8a'S)-N-{(1R)-1-[3,5-bis(trifluoromethyl)phenyl]ethyl}-2-(4-fluoro-2-methylphenyl)-N,8a'-dimethyl-hexahydro-1H-spiro[piperidine-4,6'-pyrrolo[2,1-c][1,4]oxazine]-1-carboxamide;

(2R,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide;

(2R,4S,8a'R)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide;

(2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide and (2R,4S,8a'S)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide;

or a pharmaceutically acceptable salt thereof.

In a further embodiment, the invention provides a compound having formula (Ia):

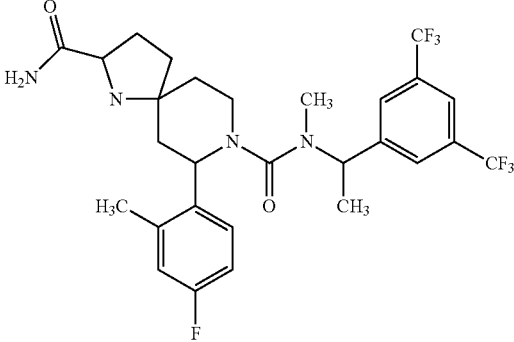

(Ia)

or a pharmaceutically acceptable salt thereof.

In a further alternative embodiment, the invention provides a compound having formula (Ib):

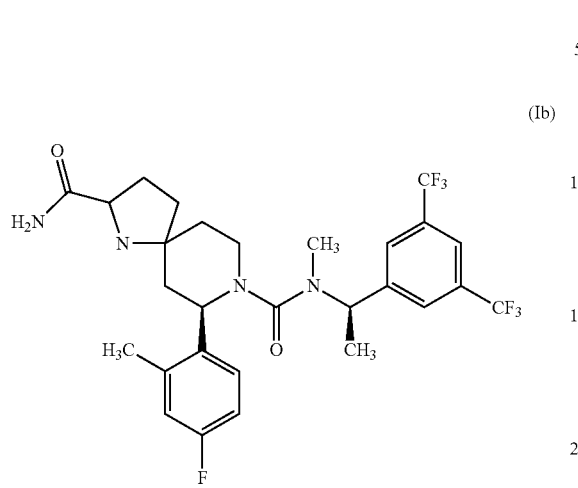

or a pharmaceutically acceptable salt thereof.

In a further embodiment, the compound of the invention is (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (Ic):

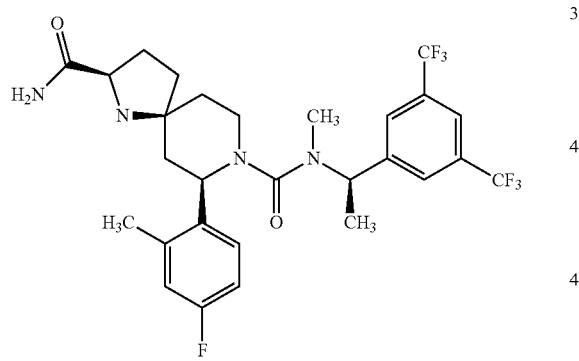

or a pharmaceutically acceptable salt thereof.

In a yet further embodiment, the invention provides (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (Ic).

In a yet further embodiment, the invention provides the hydrochloride salt of (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (Ic).

In a yet further embodiment, the invention provides (2S,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (Id):

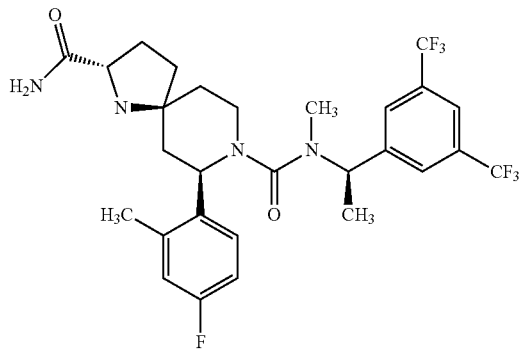

or a pharmaceutically acceptable salt thereof.

The present invention also provides a process for the preparation of the compound of formula (I) or a pharmaceutically acceptable salt thereof, which process comprises:

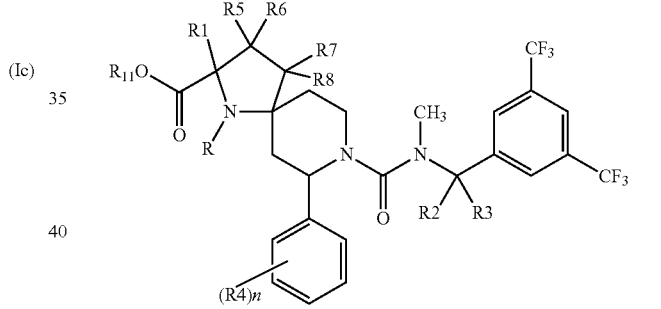

(a) reacting a compound of formula (II), wherein $R_{11}$ is methyl or ethyl and R, $R_1$, $R_2$, $R_3$, $R_4$, $R_5$, $R_6$, $R_7$, $R_8$ and $R_9$ are as defined in formula (I), (i) with ammonia in a suitable solvent such as methanol at a temperature ranging from 20-70° C., to obtain compounds of formula (I) wherein $R_9$ is C(O)NH$_2$;

or (ii) with a suitable metal hydroxide such as lithium or sodium hydroxide in a suitable solvent such as methanol, water, THF at a suitable temperature ranging from room temperature to reflux to obtain compounds of formula (I) wherein $R_9$ is C(O)$_2$H;

or (iii) with a suitable reducing agent such as lithium borohydride in a suitable solvent such as THF at a suitable temperature ranging from −78° C. to room temperature to obtain compounds of formula (I) wherein $R_9$ is CH$_2$OH;

or (b) reacting a compound of formula (III), wherein $R_1, R_2, R_3, R_4, R_5, R_6, R_7$ and $R_8$ are as defined in formula (I),

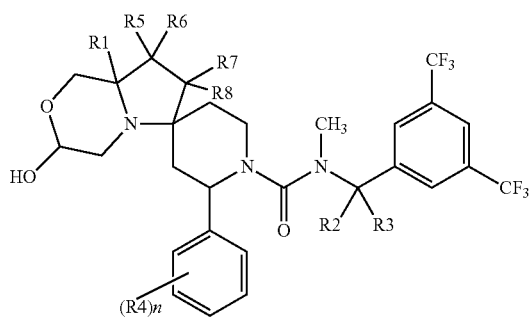

(III)

with a suitable reducing agent, such as triethylsilane in the presence of a suitable Lewis acid, such as boron trifluoride, in a suitable solvent such as dichloromethane at a suitable temperature, optionally using microwaves irradiation to obtain compounds of formula (I) wherein $R_9$ together with R form a 6 membered heterocyclic ring containing a further heteroatom selected from oxygen;

or (c) reacting a compound of formula (IV), wherein R, $R_2, R_3, R_4, R_6$ and $R_8$ are as defined in formula (I) and $R_5$ and $R_7$ are independently hydrogen, halogen, $C(O)NH_2$, or $(C_{1-4}$ alkylene)$R_{10}$, wherein $R_{10}$ is hydrogen, halogen, $C(O)NH_2$, $C(O)NH(C_{1-4}$ alkyl), $C(O)N(C_{1-4}$ alkyl)$_2$.

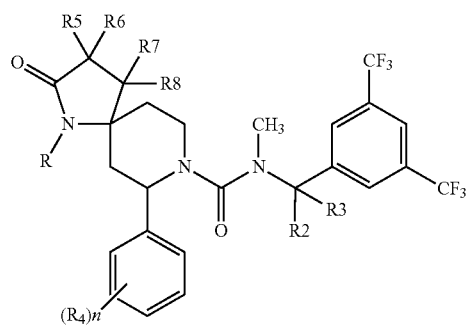

(IV)

with Meerwein's salt and with sodium cyanoborohydride to obtain compounds of formula (I) wherein R, $R_2, R_3, R_4, R_6$, and $R_8$, are as defined in formula (I), $R_1$ and $R_9$ are hydrogen and $R_5$ and $R_7$ are independently hydrogen, halogen, $C(O)NH_2$, or $(C_{1-4}$ alkylene)$R_{10}$, wherein $R_{10}$ is hydrogen, halogen, $C(O)NH_2$, $C(O)NH(C_{1-4}$ alkyl), $C(O)N(C_{1-4}$ alkyl)$_2$ or (d) reacting a compound of formula (IV), wherein R, $R_2, R_3, R_4, R_6$, and $R_8$ are as defined in formula (I) and $R_5$ and $R_7$ are independently $C(O)OR_{11}$ or $(C_{1-4}$ alkylene) $C(O)OR_{11}$,
(i) with Meerwein's salt and with sodium cyanoborohydride followed by hydrolysis reaction with a suitable metal hydroxide such as lithium or sodium hydroxide in a suitable solvent such as methanol, water, THF at a suitable temperature ranging from room temperature to reflux to obtain compounds of formula (I) wherein R, $R_2, R_3, R_4, R_6$ and $R_8$ are as defined in formula (I), $R_1$ and $R_9$ are hydrogen and $R_5$ and $R_7$ are independently $C(O)_2H$ or $(C_{1-4}$ alkylene) $C(O)_2H$ or
(ii) with Meerwein's salt and with sodium cyanoborohydride followed by addition of a selective reducing agent such as lithium borohydride, to obtain compounds of formula (I) wherein R, $R_2, R_3, R_4, R_6$ and $R_8$ are as defined in formula (I), $R_1$ and $R_9$ are hydrogen and $R_5$ and $R_7$ are independently $CH_2OH$ or $(C_{1-4}$ alkylene) $CH_2OH$;

or (e) basic hydrolysis reaction of a compound of formula (V)

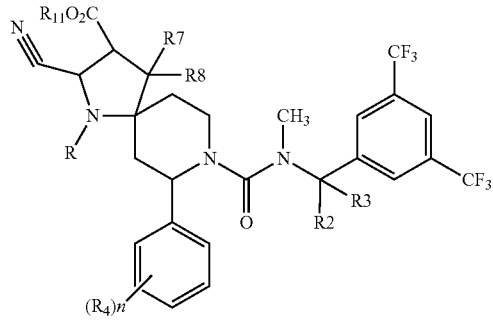

(V)

wherein R, $R_2, R_3, R_4, R_7$ and $R_8$, are as defined in formula (I), $R_1$ and $R_6$ are hydrogen and $R_{11}$ is methyl or ethyl, with a metal hydroxide such an aqueous solution of LiOH and H2O2 in a suitable solvent such as Tetrahydrofuran (THF) at a suitable temperature such as reflux temperature to obtain a compound of formula (I) wherein R, $R_2, R_3, R_4, R_7$ and $R_8$ are as defined in formula (I) and $R_1$ and $R_6$ are hydrogen, $R_5$ is $C(O)_2H$, and $R_9$ is $C(O)NH2$;

optionally thereafter followed by conversion to a pharmaceutically acceptable salt.

Some compounds of formula (I) may be obtained by reaction of a compound of formula (I).

Thus, compounds of formula (I), wherein $R_9$ is $CH_2R_{10}$ in which $R_{10}$ is halogen may be prepared by reaction of a compound of formula (I), wherein $R_9$ is $CH_2OH$ with suitable reagents such as (diethylamino)sulfur trifluoride (DAST) in a suitable solvent such as dichloromethane at a suitable temperature ranging from −78° C. to room temperature (see for example Organic & Biomolecular Chemistry, 2(5), 797-802; 2004) or thionyl chloride in a suitable solvent such as dichloromethane or chloroform at a suitable temperature ranging from low temperature to reflux (see for example Tetrahedron: Asymmetry, 14(20), 3153-3172; 2003). Alternatively, the reaction may be carried out using carbon tetrachloride and triphenylphosphine in a suitable solvent such as dichloromethane at a suitable temperature ranging from room temperature to reflux (see for example Journal of Medicinal Chemistry, 49(24), 7013-7023; 2006).

Compounds of formula (I) wherein R is $C_{1-4}$ alkyl, may be prepared by reductive amination of a compound of Formula (I), wherein R is hydrogen, with a suitable aldehyde $R_{12}CHO$, wherein $R_{12}$ is $C_{1-3}$ alkyl, and a suitable reducing agent.

For example, when R represents a methyl said reductive amination reaction may typically comprise reacting a compound of formula (I), wherein R is hydrogen, with a suitable aldehyde, such as formaldehyde (36% water solution), in a suitable solvent such as methanol at a suitable temperature such as room temperature for a time ranging from few minutes to hours followed by the addition of a suitable reducing agent such as sodium cyanoborohydride at a suitable temperature ranging from −40° C. to room temperature. Further reductive agents include, but are not limited to, sodium triacetoxyborohydride or sodium borohydride. Alternatively, the reductive step may be carried out by hydrogenation at a suitable hydrogen pressure such as 1 atm in the presence of a suitable catalyst such as palladium on carbon at a suitable temperature ranging from room temperature to high temperature.

Compounds of formula (I), wherein $R_7$ is $CH_2X$ wherein X is halogen or $R_7$ is $CH_3$, $R_9$ is $C(O)NH_2$ and R, $R_2$, $R_3$, $R_4$, $R_5$, $R_6$, $R_9$, $R_{10}$ are as described in formula (I), may be prepared from a compound of formula (I) wherein $R_7$ is $CH_2OH$, $R_9$ is $C(O)NH_2$ and R, $R_2$, $R_3$, $R_4$, $R_8$, $R_{10}$ are as described in formula in accordance with the following Scheme 1.

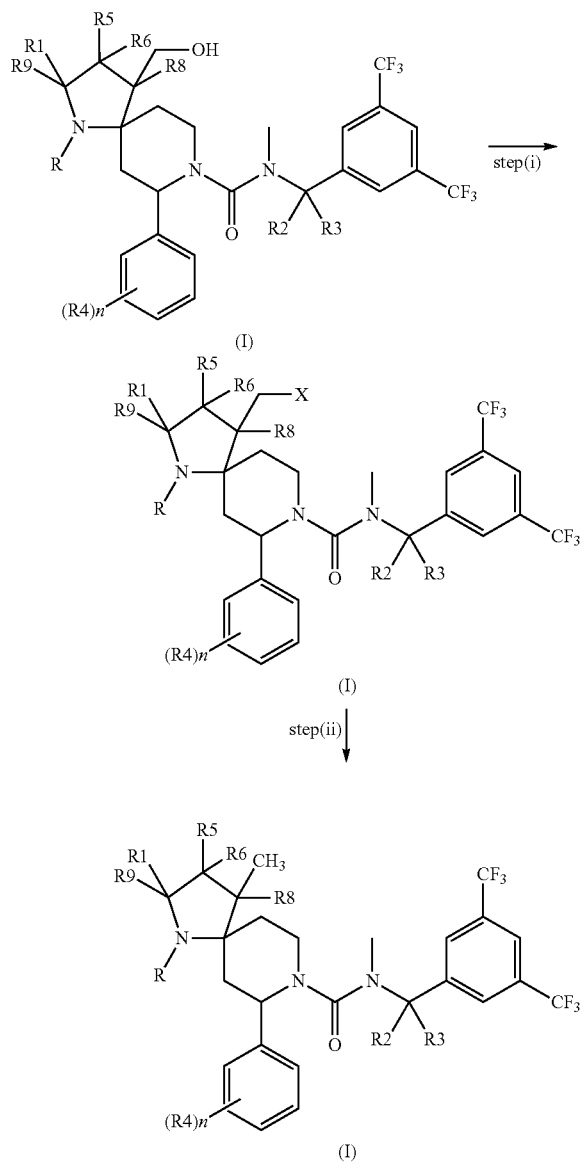

Step (i) typically comprises a suitable protection of pyrrolidine nitrogen and reaction with a suitable reagent such as (diethylamino)sulfur trifluoride (DAST) in a suitable solvent such as dichloromethane at a suitable temperature ranging from −78° C. to room temperature (see for example Organic & Biomolecular Chemistry, 2(5), 797-802; 2004) or such as thionyl chloride in a suitable solvent such as dichloromethane or chloroform at a suitable temperature ranging from low temperature to reflux (see for example Tetrahedron: Asymmetry, 14(20), 3153-3172; 2003). Alternatively the reaction may be carried out using carbon tetrachloride and triphenylphosphine in a suitable solvent such as dichloromethane at a suitable temperature ranging from room temperature to reflux (see for example Journal of Medicinal Chemistry, 49(24), 7013-7023; 2006).

Step (ii) typically comprises reduction of a suitable halogenated compound, such as a chloride, to a methyl group with Raney®-Nickel in a suitable solvent such as ethanol at high temperature (see for example Journal of Organic Chemistry, 65(19), 6249-6253; 2000).

Compounds of formula (I) wherein $R_8$ is halogen, may be prepared by a reaction of a compound of formula (I), wherein $R_8$ is hydrogen by the addition of a suitable base, followed by a suitable halogenating agent. Thus, for example for preparing compounds of formula (I) wherein $R_8$ is fluorine, the reaction is carried out with the addition of a suitable base such as lithium diisopropylamide, in the presence of N-fluorobenzenesulfonimide in a suitable solvent such as THF at a temperature ranging from −78° C. to room temperature.

Compounds of formula (II) wherein $R_1$ is $C_{1-4}$ alkyl, ($C_{1-4}$ alkylene)OH, ($C_{1-4}$ alkylene)halogen and R is hydrogen may be prepared by reaction of compound of Formula (II), wherein $R_1$ is hydrogen, in accordance with the following Scheme 2.

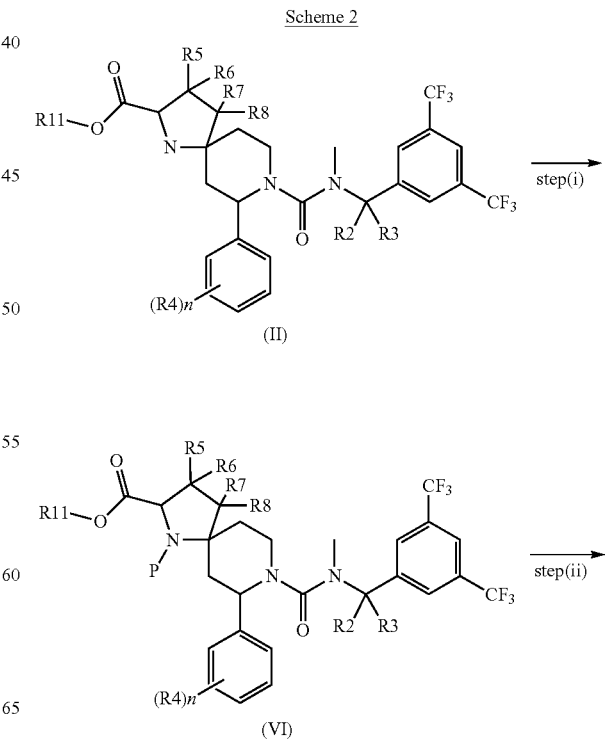

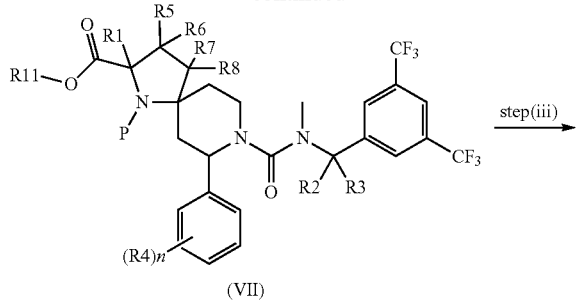

(VII)

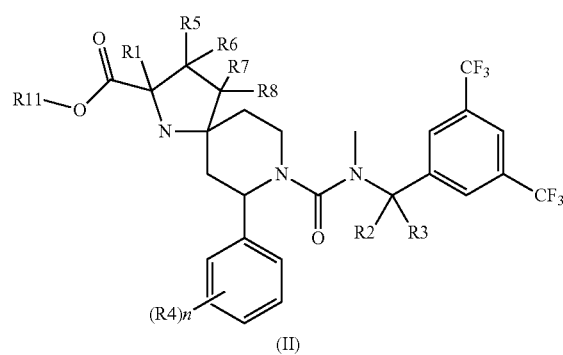

(II)

Step (i) typically comprises protection of the nitrogen with a suitable protecting group such as tertbutyloxycarbonyl (Boc), reacting a compound of formula (II) with di-tert-butyl dicarbonate in a suitable solvent such as dichloromethane or N,N-dimethylformamide at a suitable temperature ranging from 0° C. to reflux temperature optionally in the presence of a suitable base such as triethylamine, diisopropylethylamine.

Step (ii) typically comprises alkylation by reaction with a suitable base such as lithium bis(trimethylsilyl)amide in a suitable solvent such as THF at a suitable temperature ranging from −78° C. to room temperature for a time ranging from few minutes to hours, followed by in situ addition of $(C_{1-4}$ alkyene) X (VIII), P'O($C_{1-4}$)alkyl X (IX) or X($C_{1-4}$ alkyene) halogen(X), wherein X is a suitable leaving group such as a halogen, mesyl, tosyl, trifluoromethanesulfonyl, at a suitable temperature ranging from −78° C. to high temperature and P' is a suitable oxygen protective group such as trimethylsilyl, tertbutyldimethylsilyl, tertbutyldiphenylsilyl.

Step (iii) typically comprises a deprotection reaction, for example, when P represents Boc said deprotection reaction may typically comprise reacting a compound of formula (VII) with a mixture of dichloromethane and trifluoroacetic acid and when P' is trimethylsilyl, tertbutyldimethylsilyl, tertbutyldiphenylsilyl group, the removal of oxygen protective group may be carried out selectively using a fluorinated reagent such as tetrabutylammonium or cesium fluoride in a suitable solvent such as THF, acetonitrile or methanol at a suitable temperature such as room temperature.

Alternatively, the oxygen protective group may be removed not selectively using the same reaction conditions described before to remove nitrogen protective group when P is Boc.

Compounds of formula (II), wherein R, $R_2$, $R_3$, $R_4$, $R_5$, $R_6$, $R_7$ and $R_8$, are as defined in formula (I) and $R_1$ is hydrogen and $R_{11}$ is methyl or ethyl may be prepared by reaction of a compound of formula (XI),

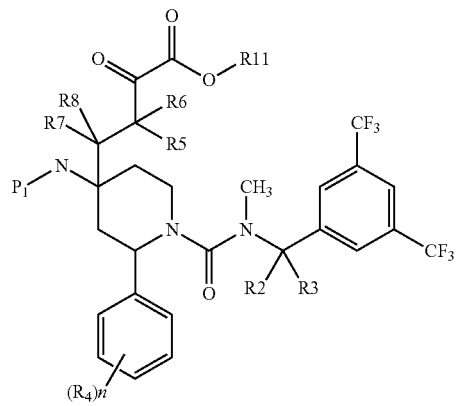

(XI)

wherein P1 is a suitable nitrogen protecting group such as (R or S) tertbutylsulfinyl or tertbutyloxycarbonyl (Boc) or benzyloxycarbonyl (Cbz), and $R_{11}$ is $C_{1-4}$ alkyl, which comprises deprotection of nitrogen protecting group P1, followed by an in situ intramolecular cyclisation of the resulting free amine and final reduction of the imine intermediate to form the compound (II).

For example, when P1 represents tertbutylsulfinyl or Boc, said deprotection reaction may typically comprise reacting a compound of formula (XI) with trifluoroacetic acid in a suitable solvent such as dichloromethane or hydrochloric acid in a suitable solvent such as methanol at room temperature. The deprotected intermediate may cyclize in situ in the acidic conditions and the resulting imine may be reduced with a suitable reducing agent such as triethylsilane in the same reaction conditions. Further suitable reductive agents which may be used include for example sodium or lithium borohydride. The reaction can be carried out in a suitable solvent, such as THF or methanol at a temperature ranging from 0° C. to room temperature.

Alternatively, a catalytic hydrogenation at a suitable hydrogen pressure such as 1 atm with a suitable catalyst such as Palladium on carbon in a suitable solvent such as methanol, ethanol, ethyl acetate may be carried out.

As described in the following Scheme 3, said cyclisation reaction allows the formation of a mixture of diastereoisomers whose separation into the single diastereoisomer may be carried out by conventional means such as chromatography or crystallisation.

Scheme 3

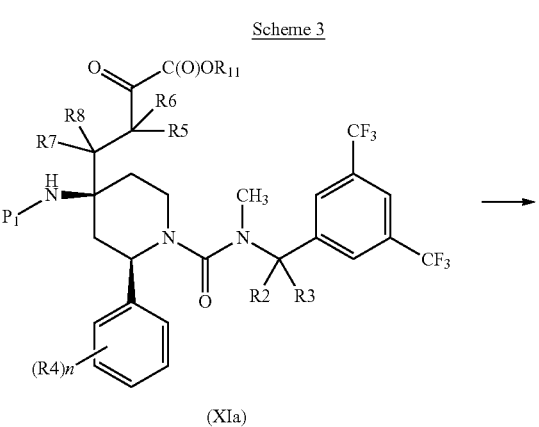

(XIa)

-continued

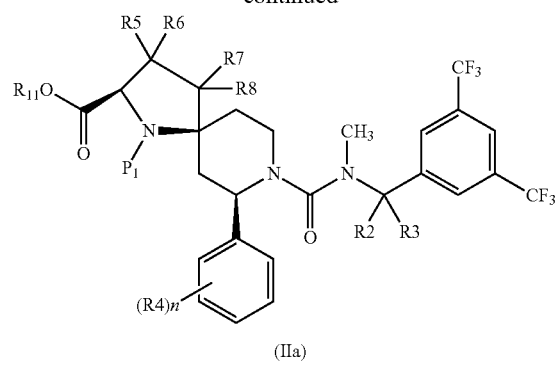

(IIa)

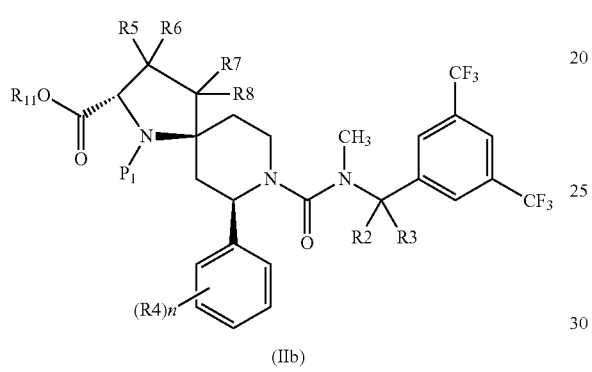

(IIb)

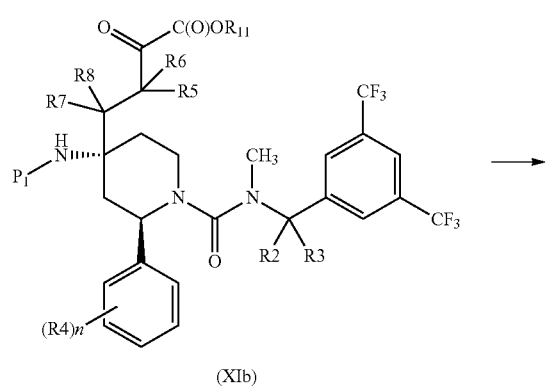

(XIb)

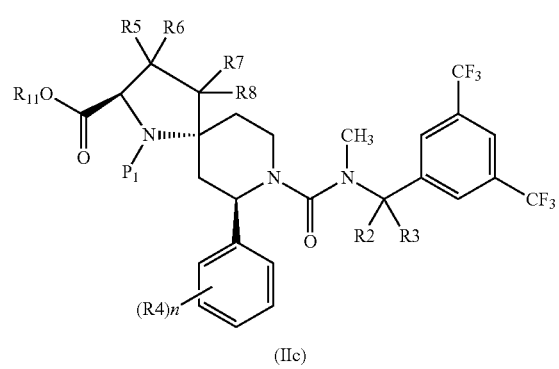

(IIc)

-continued

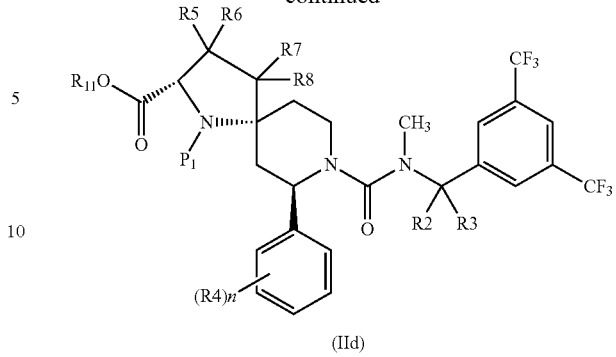

(IId)

In a further embodiment, compounds of formula (II), wherein $R_2$, $R_3$, $R_4$, $R_7$ and $R_8$ are as defined in formula (I) and R, $R_1$, $R_5$, $R_6$ and R are hydrogen may be prepared by cyclisation of a compound of formula (XII),

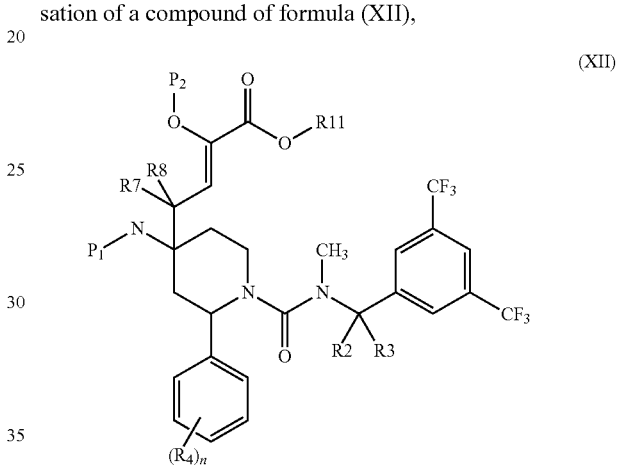

(XII)

wherein P2 is a suitable enol ether protecting group such as tertbutyldimethylsilyl and P1 a suitable nitrogen protecting group such as benzyloxycarbonyl (Cbz), in a suitable solvent such as methanol with cesium fluoride and a suitable catalyst such as Palladium on carbon under a hydrogen atmosphere, at a suitable pressure such as 1 atm, followed by removal of the nitrogen protecting group.

As described in the following Scheme 4, said cyclisation reaction allows the formation of a mixture of diastereoisomers whose separation into the single diastereoisomer may be carried out by conventional means such as chromatography or crystallisation.

Scheme 4

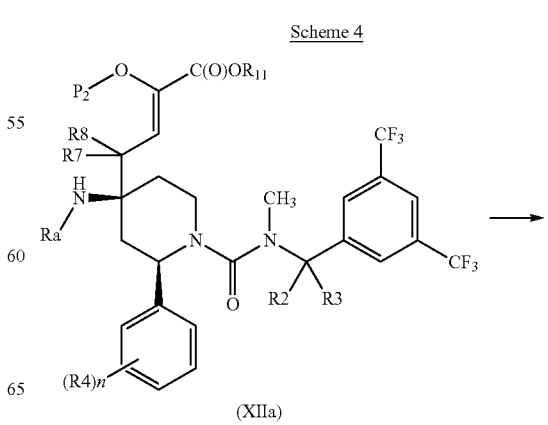

(XIIa)

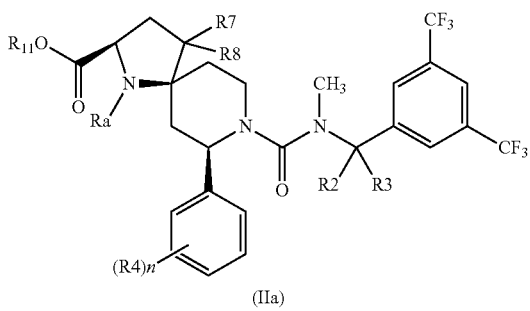

(IIa)

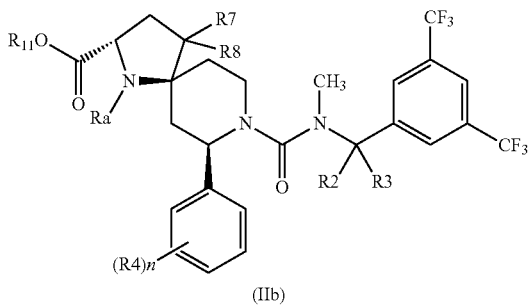

(IIb)

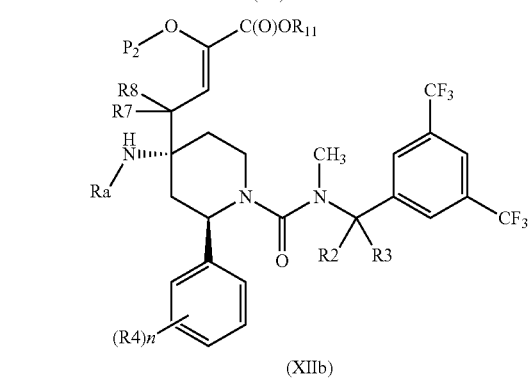

(XIIb)

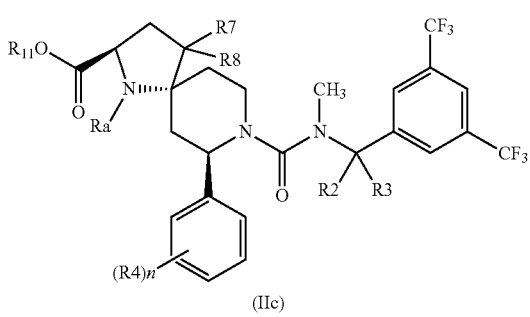

(IIc)

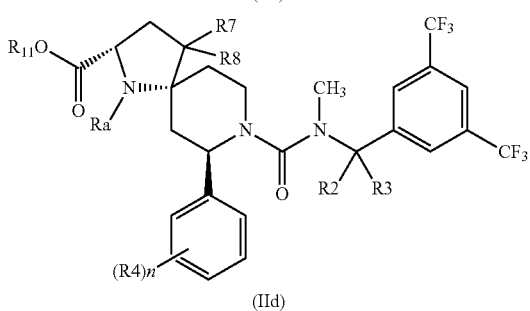

(IId)

In a further embodiment, compounds of formula (II) may be prepared by catalytic hydrogenation of a compound of formula (XIII),

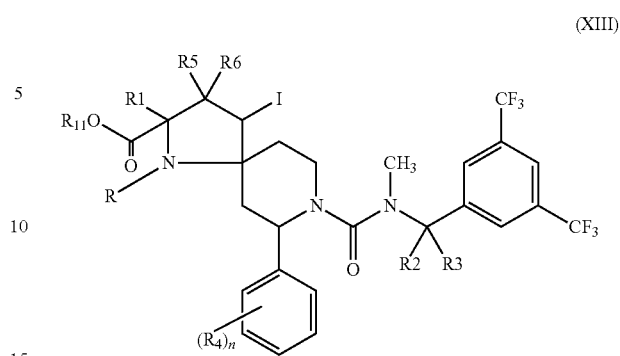

(XIII)

wherein $R_{11}$ is methyl or ethyl and R, $R_1$, $R_2$, $R_3$, $R_4$, $R_5$, $R_6$, are as defined in formula (I), with a suitable catalyst such as palladium on carbon in a suitable solvent such as methanol, ethanol, ethyl acetate at a suitable hydrogen pressure such as 1 atm.

Compounds of formula (III) may be prepared from a compound of formula (XIV)

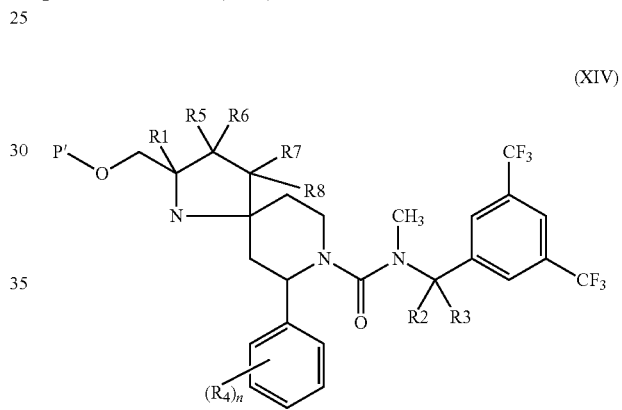

(XIV)

wherein R, $R_2$, $R_3$, $R_4$, $R_5$, $R_6$, $R_7$, $R_8$, $R_{10}$ are as defined in formula (I) and P' is a suitable alcohol protecting group, by reductive amination, followed by in situ cyclization. For example, said reductive amination may be carried out reacting compound (XIV) with a suitable aldehyde such as Glyoxal solution (40 wt. % in water) in a suitable solvent such as acetonitrile at a suitable temperature such as room temperature for a suitable time to form the intermediate imine. Following addition of a suitable reducing agent such as Sodium cyanoborohydride may give the intermediate aldehyde, which may cyclize in situ, after removal of the alcohol protecting group P', to give compound (III). The reductive amination may be optionally promoted by the addition of a catalytic amount of an acid such as glacial acetic acid.

Compounds of formula (IV), wherein R is hydrogen, $R_2$, $R_3$, $R_4$, $R_6$, $R_7$, $R_8$, and $R_{10}$ are as defined in formula (I) and $R_5$ is hydrogen, hydroxy, halogen, $C(O)NH_2$, $C(O)OR_{11}$ or ($C_{1-4}$ alkylene) $R_{10}$ wherein $R_{10}$ is hydrogen, hydroxyl, halogen, $C(O)NH_2$, $C(O)NH(C_1\text{-4 alkyl})$, $C(O)N(C_{1-4}\ \text{alkyl})_2$ or ($C_{1-4}$ alkylene) $C(O)OR_{11}$, wherein $R_{11}$ is methyl or ethyl, may be prepared in accordance with the following Scheme 5.

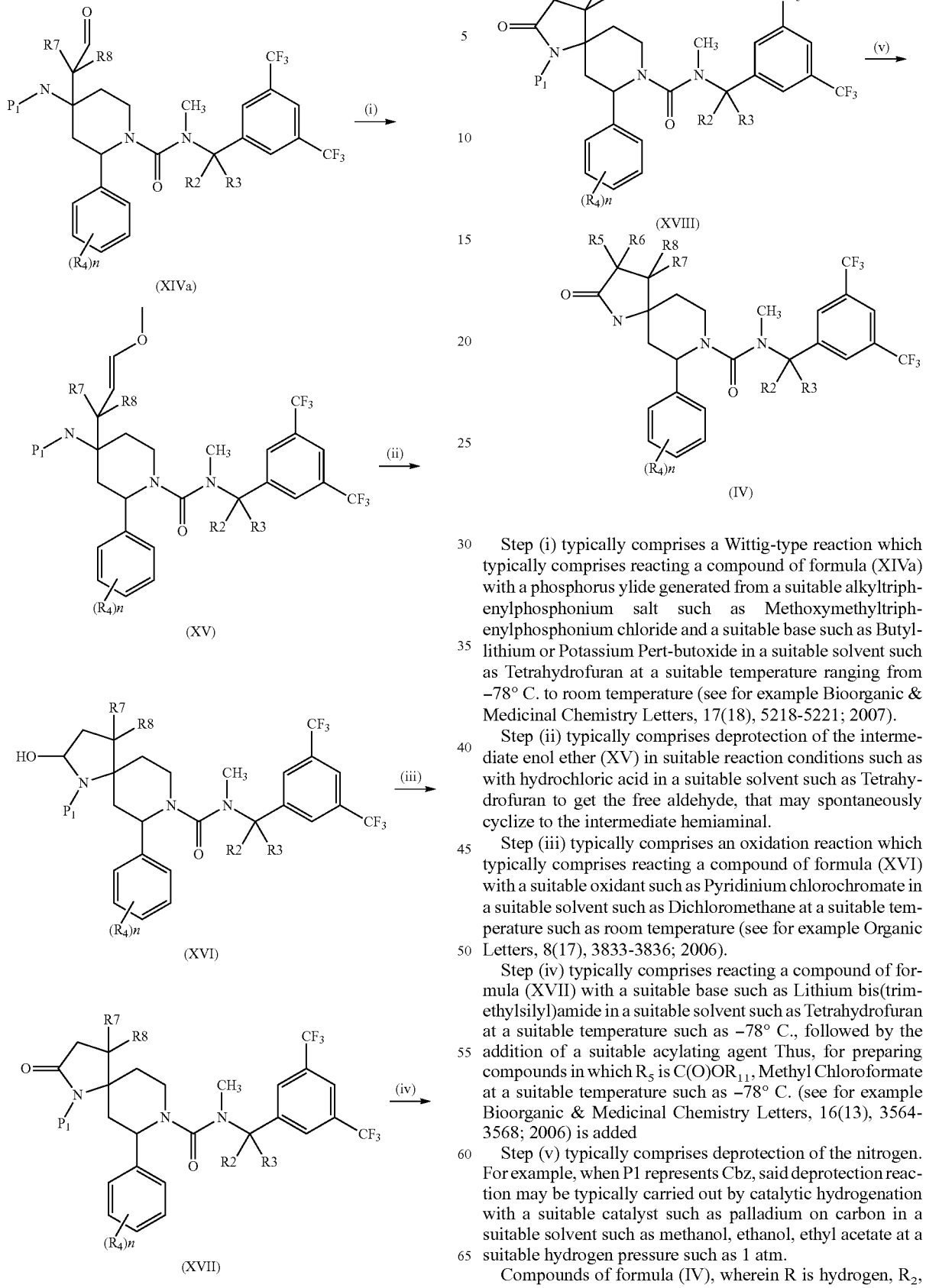

Step (i) typically comprises a Wittig-type reaction which typically comprises reacting a compound of formula (XIVa) with a phosphorus ylide generated from a suitable alkyltriphenylphosphonium salt such as Methoxymethyltriphenylphosphonium chloride and a suitable base such as Butyllithium or Potassium Pert-butoxide in a suitable solvent such as Tetrahydrofuran at a suitable temperature ranging from −78° C. to room temperature (see for example Bioorganic & Medicinal Chemistry Letters, 17(18), 5218-5221; 2007).

Step (ii) typically comprises deprotection of the intermediate enol ether (XV) in suitable reaction conditions such as with hydrochloric acid in a suitable solvent such as Tetrahydrofuran to get the free aldehyde, that may spontaneously cyclize to the intermediate hemiaminal.

Step (iii) typically comprises an oxidation reaction which typically comprises reacting a compound of formula (XVI) with a suitable oxidant such as Pyridinium chlorochromate in a suitable solvent such as Dichloromethane at a suitable temperature such as room temperature (see for example Organic Letters, 8(17), 3833-3836; 2006).

Step (iv) typically comprises reacting a compound of formula (XVII) with a suitable base such as Lithium bis(trimethylsilyl)amide in a suitable solvent such as Tetrahydrofuran at a suitable temperature such as −78° C., followed by the addition of a suitable acylating agent Thus, for preparing compounds in which $R_5$ is $C(O)OR_{11}$, Methyl Chloroformate at a suitable temperature such as −78° C. (see for example Bioorganic & Medicinal Chemistry Letters, 16(13), 3564-3568; 2006) is added Step (v) typically comprises deprotection of the nitrogen. For example, when P1 represents Cbz, said deprotection reaction may be typically carried out by catalytic hydrogenation with a suitable catalyst such as palladium on carbon in a suitable solvent such as methanol, ethanol, ethyl acetate at a suitable hydrogen pressure such as 1 atm.

Compounds of formula (IV), wherein R is hydrogen, $R_2$, $R_3$, $R_4$, $R_5$, $R_6$, $R_8$, and $R_{10}$ are as defined in formula (I) and $R_7$ is C(O)OR$_{11}$, wherein R$_{11}$ is methyl or ethyl, may be prepared in accordance with the following Scheme 6.

Scheme 6

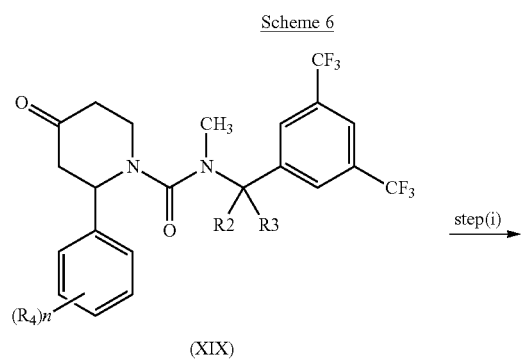

(XIX)

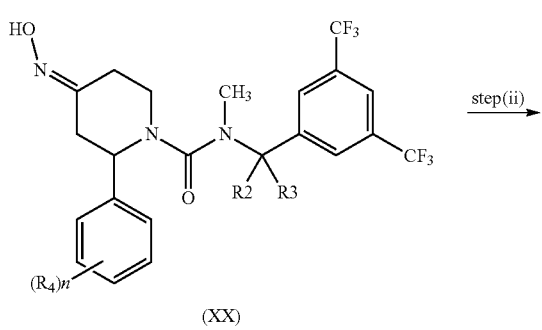

(XX)

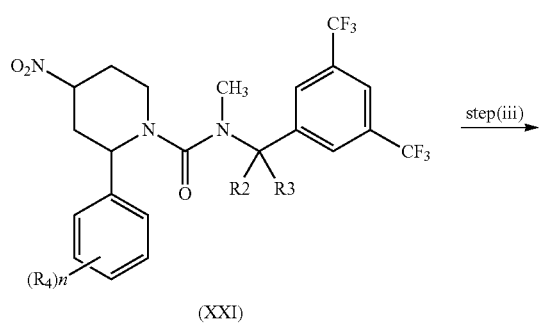

(XXI)

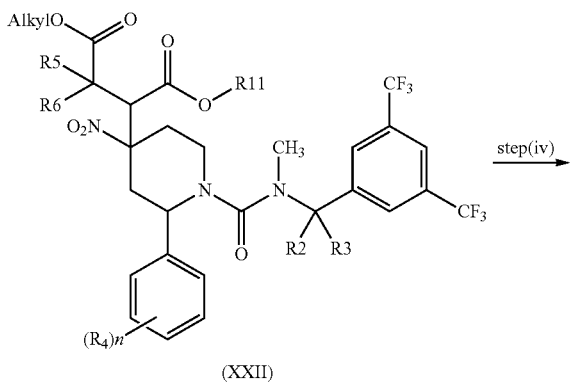

(XXII)

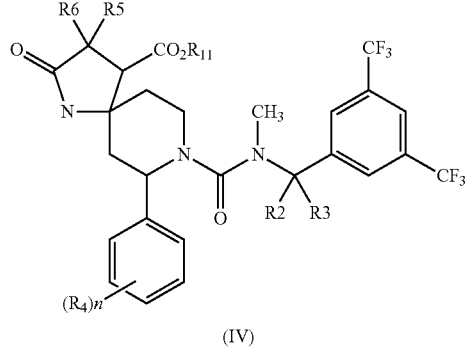

(IV)

Step (i) typically comprises reacting a compound of formula (XIX) with hydroxylamine hydrochloride and sodium bicarbonate in a suitable solvent such as ethanol at a suitable temperature such as 50° C.

Step (ii) typically comprises reacting a compound of formula (XX) with urea Na$_2$HPO$_4$ and mCPBA in a suitable solvent such as acetonitrile at a suitable temperature such as reflux temperature.

Step (iii) typically comprises reacting a compound of formula (XXI) with potassium fluoride and tetrabutylammonium iodide, followed by the addition of dimethyl maleate in a suitable solvent such as dimethyl Sulfoxide.

Step (iv) typically comprises reduction of the nitro group of a compound of formula (XXII), followed by in situ cyclization of the resulting free amine to get lactam (IV). Said reduction reaction may be carried out in a suitable solvent such as methanol in the presence of Raney® Nickel, Compounds (V) may be prepared by reacting a compound of formula (IV) with a suitable reductive agent such as Diisobutylaluminum hydride in the presence of a suitable Lewis acid such as Boron trifluoride diethyl etherate at a suitable temperature such as −78° C. to get the intermediate hemiaminal, which can be conveniently converted into compound (V) by reaction with Trimethylsilyl cyanide and Trimethylsilyl trifluoromethanesulfonate in a suitable solvent such as dichloromethane at a suitable temperature ranging from 0° C. to room temperature (see for example Journal of the American Chemical Society, 129(42), 12890-12895; 2007).

Compounds of formula (XIII) may be obtained in accordance with the following Scheme 7.

Scheme 7

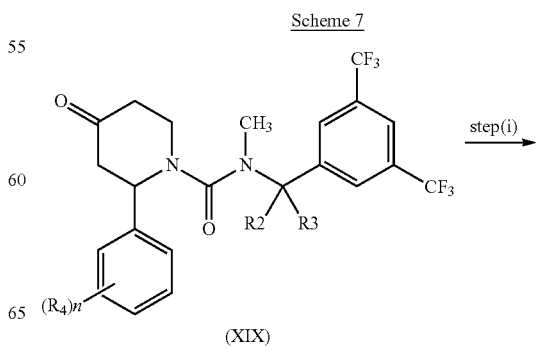

(XIX)

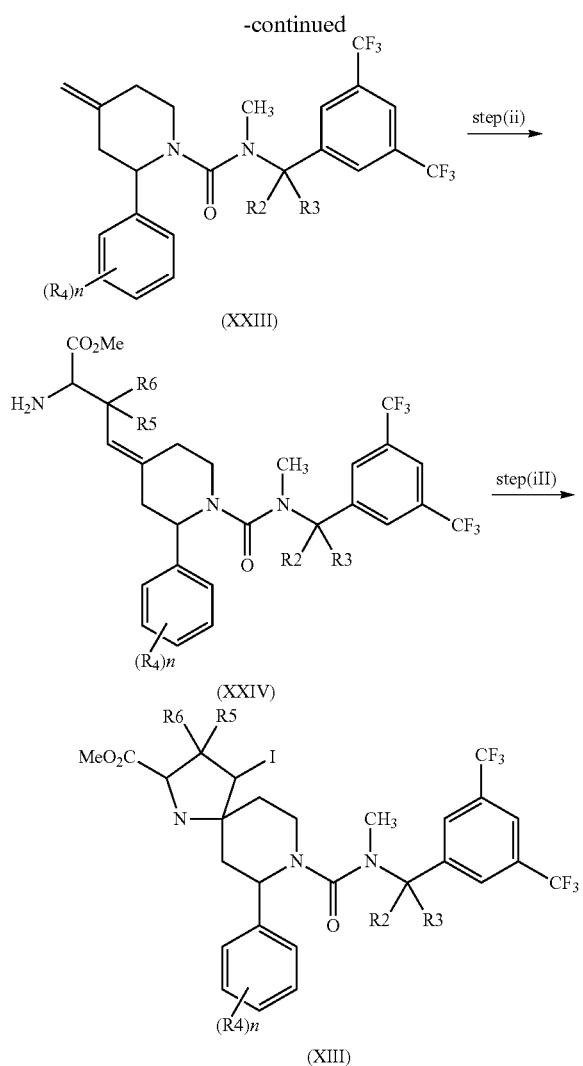

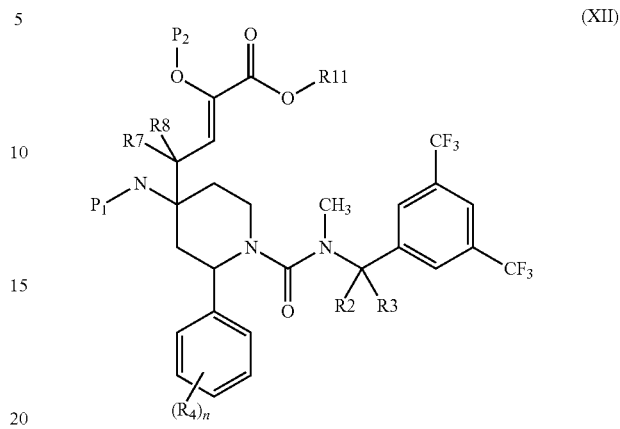

Compounds of formula (XI) may be prepared by reaction of a compound of formula (XII), wherein $R_2$, $R_3$, $R_4$, $R_7$ and $R_8$ are as defined in formula (I), $R_{11}$ is methyl or ethyl, P1 is a suitable nitrogen protecting group and P2 is a suitable enol ether protecting group such as a silyl enol ether (i.e. tertbutyldimethylsilyl, tertbutyldiphenylsilyl, trimethylsilyl) or an alkyl enol ether (i.e. ethyl, methyl), which comprises deprotection of enol ether protecting group P2 with a suitable reagent to form the compound (XI).

For example, when P2 represents a tertbutyldimethylsilyl enol ether, the removal of the protecting group may typically comprise reacting a compound of formula (XII) with cesium fluoride in a suitable solvent such as acetonitrile or methanol in the presence of a mild acid such as acetic acid at room temperature. Further suitable fluoride reagents may be used (see Greene, Wutz "Protective groups in organic synthesis") such as tetrabutylammonium fluoride in a suitable solvent such as THF at room temperature.

The compound of formula (XII) may be prepared by Horner-Wadsworth-Emmons olefination of compound of formula (XXIV), wherein $R_2$, $R_3$, $R_4$, $R_7$ and $R_8$ are as defined in formula (I) and P1 is a suitable nitrogen protected group,

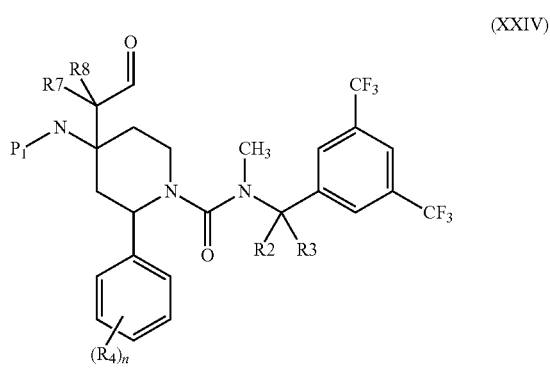

Step (i) typically comprises a Wittig reaction of ketone (XIX) with triphenylmethyl phosphonium bromide in the presence of a suitable base e.g sodium hydride or potassium tert-butoxide in a suitable solvents, such as tetrahydrofuran, in a temperature range from −15 C to 25° C.

Step (ii) typically comprises reacting olefin (XXIII) with allylglycine nitrogen-protected derivative in the presence of Hoveyda-Grubbs catalyst $2^{nd}$ generation i.e. (1,3-bis-(2,4,6-trimethylphenyl)-2-imidazolidinylidene)dichloro(o-isopropoxyphenylmethylene)ruthenium, in typically dichloromethane or 1,2-dichloroethane at reflux for several hours.

Step (iii) typically comprises cyclisation of homoallyl amine derivatives (XXIV) with molecular iodine in dipolar aprotic solvents such as acetonitrile, at room temperature and in the presence of a base e.g. sodium bicarbonate or carbonate.

The reaction of compound (XIV) may be also carried out with nitrogen N protected with a suitable N protecting group.

Compounds of formula (XIV) may be prepared by reaction of a compound of formula (I) wherein $R_9$ is $CH_2OH$ with a suitable oxygen protective agent such as trimethylsilyl chloride, terbutyldimethylsilylchloride or tertbutyldiphenylsilylchloride.

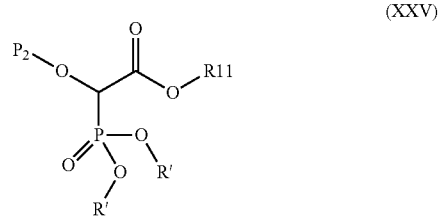

with a suitable phosphonate (XXV) (see *Tetrahedron Lett.* 1981, 22, 663-666; *J. Org. Chem.* 2006, 71, 9144-9152), wherein R' is a suitable $C_{1-4}$ alkyl group such as methyl and $R_{11}$ is methyl or ethyl, in the presence of a base to generate phosphonate carbanion. For example, when R' represents a methyl, $R_{11}$ represents a methyl or ethyl substituent and P2 represents a tertbutyldimethylsilyl ether or ethyl ether, said Horner-Wadsworth-Emmons reaction may typically comprise reacting a compound of formula (XXIV) with a suitable base such as 1,8-Diazabicyclo[5.4.0]undec-7-ene in a suitable solvent such as acetonitrile in the presence of a metal salt such as Lithium chloride at a suitable temperature such as 0° C., followed by the addition of the compound (XXIV) (see *J. Org. Chem.* 2006, 71, 9144-9152). Further suitable bases may be used such as sodium hydride, potassium hydride, potassium bis(trimethylsilyl)amide, lithium bis(trimethylsilyl)amide, potassium tert-butoxide, lithium diisopropylamide in a suitable solvent such as THF at a temperature ranging from −78° C. to room temperature (see *Tetrahedron Lett.* 1981, 22, 663-666; L. Kürti, B. Czakó "Strategic applications of named reactions in organic synthesis").

The compound of formula (XXIV) may be prepared by oxidative cleavage of a compound of formula (XXVI), wherein $R_2$, $R_3$, $R_4$, $R_7$ and $R_8$ are as defined in formula (I) and P1 is a suitable nitrogen protected group,

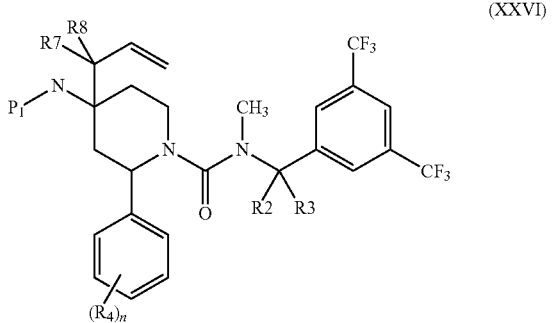

(XXVI)

which comprises treatment with ozone in a suitable solvent such as dichloromethane at a suitable temperature such as −78° C., followed by reduction of the intermediate ozonide to the aldehyde (XXIV) with a suitable reducing agent such as dimethyl sulfide at suitable temperature ranging from −78° C. to room temperature. Further reducing agents may be used such as triphenylphosphine in a suitable solvent such as dichloromethane at a temperature ranging from −78° C. to room temperature.

Alternatively, said oxidative cleavage may comprise reacting compound (XXVI) with osmium tetroxide in a suitable solvent such as 1,4-Dioxane at room temperature, followed by treatment with sodium periodate.

The compound of formula (XXVI) may be prepared by allylation of a compound of formula (XXV),

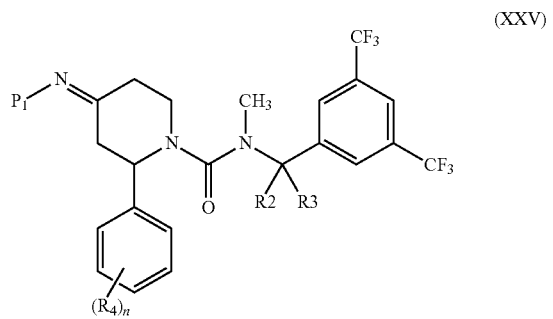

(XXV)

wherein P1 is a suitable nitrogen protecting group, which comprises addition of an allylic organometallic reagent derivative to the imine (XXV) to obtain a mixture of two diastereoisomers (XXVIa) and (XXVIb),

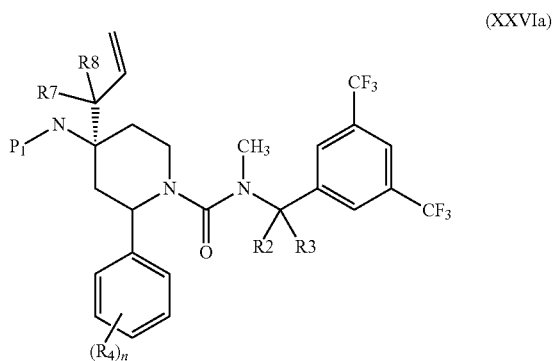

(XXVIa)

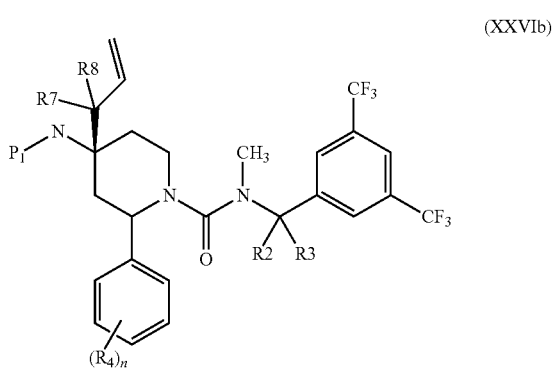

(XXVIb)

Said mixture of diastereoisomers may be separated into the single diastereoisomer by conventional means such as chromatography or crystallisation.

For example, when P1 represents a (R or S) tertbutylsulfinyl group, said allylation reaction may typically comprise reacting a compound of formula (XXV) with a suitable allylic organometallic reagent such as allyl zinc bromide, generated in situ from allylbromide and zinc, in a suitable solvent such as THF at a temperature ranging from −78° C. to room temperature. Examples of suitable allylic organometallic reagents include but are not limited to allyl magnesium reagents, allyl boron derivative reagents, allylsilanes, allylstannane derivatives and the reaction may be promoted by Lewis acids.

Alternatively, a compound of formula (XXV), wherein the protecting group is absent and P1 is hydrogen, may be reacted with a suitable allylic organometallic derivative reagent such as an allyl boron reagents (see *Chem. Commun.*, 2005, 5551-5553). Protection of the nitrogen with a suitable protecting group P1 such as tertbutyloxycarbonyl (Boc) or (Cbz) gives a compound (XXVI).

The compound of formula (XXV) may be prepared by reacting a compound of formula (XIX),

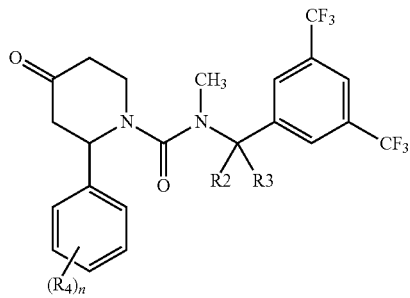

(XIX)

with a suitable amine such as (R)-(+)-2-Methyl-2-propanesulfinamide or (S)-(−)-2-Methyl-2-propanesulfinamide in a suitable solvent such as THF in the presence of Titanium(IV) ethoxide (see Synlett, (16), 2565-2568; 2006). Examples of suitable amines include but are not limited to, any other sulfinamides such as for example p-tolyl sulfinamide, ammonia, benzylamine, glycine.

Alternatively, a compound of formula (XXVI) may be prepared according to Scheme 8, wherein $R_7$ and $R_8$ are as defined in formula (I) and P1 is a suitable nitrogen protected group.

Scheme 8

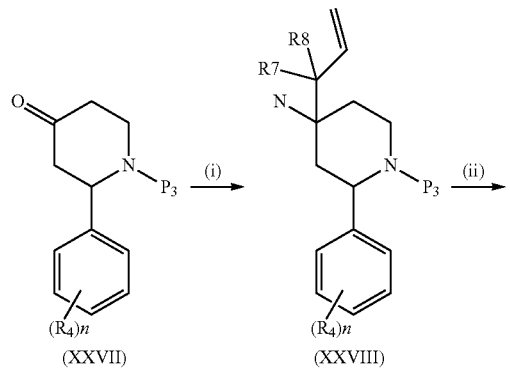

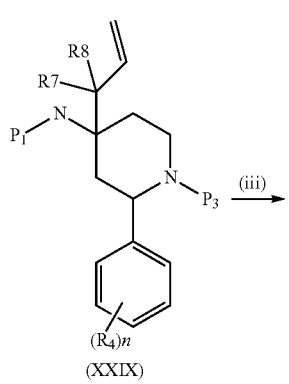

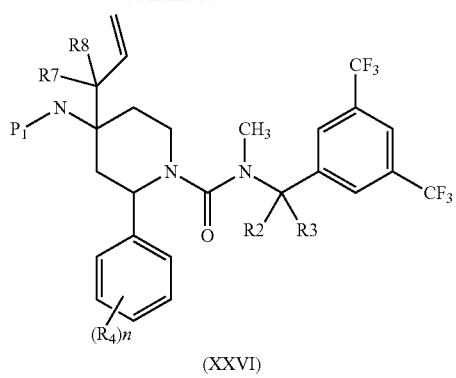

(XXVI)

Step (i) typically comprises in situ formation of an imine intermediate formed by treating a compound of formula (XXVII) protected with a suitable nitrogen protecting group such as tertbutyloxycarbonyl (Boc), with ammonia in a suitable solvent such as MeOH, followed by the addition of a suitable allylic organometallic reagent such as for example 4,4,5,5-tetramethyl-2-(2-propen-1-yl)-1,3,2-dioxaborolane to obtain compounds (XXVIII) wherein $R_7$ and $R_8$ are hydrogen.

Step (ii) typically comprises protection of a compound of formula (XXVIII) with a suitable nitrogen protecting group $P_1$. For example, when $P_1$ represents benzyloxycarbonyl (Cbz), said protection reaction may typically comprise reacting compound of formula XXVIII with Dibenzyl dicarbonate in a suitable solvent such as DCM at a suitable temperature such as 0° C.

Step (iii) typically comprises reacting a compound of formula (XXIX) with a suitable amine such as {[3,5-bis(trifluoromethyl)phenyl]methyl}methylamine or {(1R)-1-[3,5-bis(trifluoromethyl)phenyl]ethyl}methylamine in the presence of triphosgene and of a suitable base such as triethylamine in a suitable solvent such as ethyl acetate at a suitable temperature such as reflux temperature. For example, when compound of formula (XXIX) is a single enantiomer and the amine is a racemate such as {1-[3,5-bis(trifluoromethyl)phenyl]ethyl}methylamine, this reaction comprises formation of a mixture of diastereoisomers whose separation into the single diastereoisomer may be carried out by conventional means such as chromatography or crystallisation.

The allylation reaction describes in Step (i) produces a mixture of diastereoisomers whose separation into the single diastereoisomer may be carried out by conventional means such as chromatography or crystallisation, see Scheme 9

Scheme 9

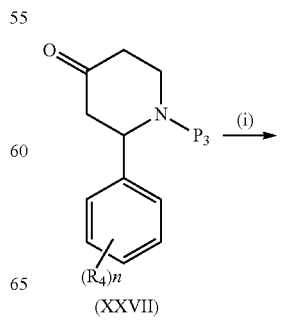

(XXVII)

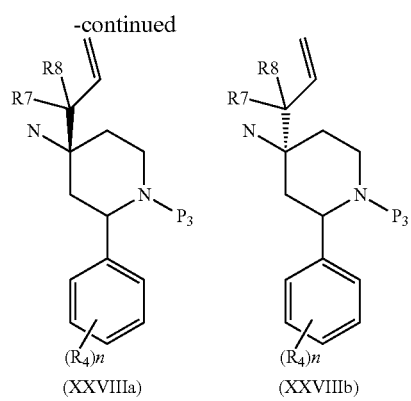

(XXVIIIa)  (XXVIIIb)

The preparation of compounds (XIX) are described in PCT publication WO0232867 published on 25 Apr. 2002.

The preparation of compounds (XXVI) are described in PCT publication WO 2007107818 published on 27 Sep. 2007).

The preparation of compounds (XXVII) are described in PCT publication WO 2008090117 published on 31 Jul. 2008.

When a specific enantiomer of a compound of general formula (I) is required, this may be obtained for example by resolution of a corresponding enantiomeric mixture of a compound of formula (I) using conventional methods.

Thus, for example, specific enantiomers of the compounds of formula (I) may be obtained from the corresponding enantiomeric mixture of a compound of formula (I) using chiral HPLC procedure.

Alternatively, enantiomers of a compound of general formula (I) may be synthesised from the appropriate optically active intermediates using any of the general processes described herein.

When it is desired to isolate a compound of formula (I) as a salt, for example a pharmaceutically acceptable salt, this may be achieved by reacting the compound of formula (I) in the form of the free base with an appropriate amount of a suitable acid and in a suitable solvent such as an alcohol (e.g. ethanol or methanol), an ester (e.g. ethyl acetate) or an ether (e.g. diethyl ether or tetrahydrofuran).

Pharmaceutically acceptable salts may also be prepared from other salts, including other pharmaceutically acceptable salts, of the compounds of formula (I) using conventional methods.

The compounds of formula (I) may readily be isolated in association with solvent molecules by crystallisation from or evaporation of an appropriate solvent to give the corresponding solvates.

Compounds of formula (I) and their pharmaceutically acceptable salts have affinity for and are specific antagonists of tachykinins, including substance P and other neurokinins.

Tachykinins are a family of peptides that share a common carboxyl-terminal sequence (Phe-X-Gly-Leu-Met-NH2). They are actively involved in the physiology of both lower and advanced life forms. In mammalian life forms, the main tachykinins are substance P(SP), Neurokinin A (NKA) and Neurokinin B (NKB) which act as neurotransmitters and neuromodulators. Mammalian tachykinins may contribute to the pathophysiology of a number of human diseases.

Three types of tachykinins receptors have been identified, namely NK1 (SP-preferring), NK2 (NKA-preferring) and NK3 (NKB-preferring) which are widely distributed throughout the central nervous (CNS) and peripheral nervous system.

Particularly, compounds of the invention are antagonists of the NK1 receptor.

Compounds of the invention are useful in the treatment of conditions mediated by tachykinins.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Compounds of formula (I) or pharmaceutically acceptable salts thereof may be of use in the treatment of the following disorders:

Depression and mood disorders including Major Depressive Episode, Manic Episode, Mixed Episode and Hypo manic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypo manic Episodes) (296.89), Cyclothymiacs Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00).

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Sleep disorders including primary sleep disorders such as Dyssomnias such as Primary Insomnia (307.42), Primary Hypersomnia (307.44), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50).

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9):

Compounds of the invention may be useful for Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

Compounds of the invention may be also useful as anti-inflammatory agents. In particular, they may be useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis, overactive bladder and urge incontinence; and eye and dental inflammation.

Compounds of the invention may be also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. Compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral, e.g. myocardial infarction or peritonitis; migraine; increased intercranial pressure; decreased intercranial pressure (e.g. altitude sickness); opioid analgesics, such as morphine; and gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia.

Compounds of the invention may be also useful in the treatment of gastrointestinal disorders such as irritable bowel syndrome, gastro-oesophageal reflux disease (GERD) such as erosive GERD and symptomatic GERD or non erosive GERD, acid indigestion, over-indulgence of food or drink, acid stomach, sour stomach, waterbrash/regurgitation, heartburn, such as episodic heartburn, nocturnal heartburn, and meal-induced heartburn, dyspepsia and functional dyspepsia (such as ulcer-like dyspepsia, dysmotility-like dyspepsia and unspecified dyspepsia) chronic constipation; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Within the context of the present invention, the term "pain" includes: chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with cluster and chronic daily headache; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; dysmenorrhea; neuralgia; fibromyalgia syndrome; complex regional pain syndrome (CRPS types I and II); neuropathic pain syndromes (including diabetic neuropathy; chemoterapeutically induced neuropathic pain; sciatica; non-specific lower back pain; multiple sclerosis pain; HIV-related neuropathy; post-herpetic neuralgia; trigeminal neuralgia); and pain resulting from physical trauma, amputation, cancer, toxins or chronic inflammatory conditions.

Compounds of the invention may be useful in cachexia including systemic cachexia, cachexia secondary to infection or malignancy and cachexia secondary to AIDS, renal insufficiency, cardiac insufficiency and pulmonary insufficiency.

Compounds of the invention may be also useful for treatment of patients suffering from anorexia-cachexia syndrome which is a debilitating condition characterizing the clinical journey of patients suffering from chronic diseases including cancer, chronic obstructive pulmonary disease, tuberculosis, chronic heart failure, and end-stage renal insufficiency.

All of the various forms and sub-forms of the disorders mentioned herein are contemplated as part of the present invention.

Compounds of the invention are particularly useful in the treatment or prevention of depression, anxiety, sleep disorders or emesis.

Compounds of the invention are particularly useful in the treatment or prevention of sleep disorders.

The invention therefore provides a compound of formula (I) or a pharmaceutically acceptable salt thereof for use in therapy.

Thus, the invention also provides a compound of formula (I) or a pharmaceutically acceptable salt thereof, for use as a therapeutic substance in the treatment or prophylaxis of the above disorders.

The invention further provides a compound of formula (I) or a pharmaceutically acceptable salt thereof, for use in the treatment of depression, anxiety, sleep disorders or emesis.

The invention further provides a method of treatment or prophylaxis of conditions mediated by tachykinins, in mammals including humans, which comprises administering to the sufferer a therapeutically effective amount of a compound of formula (I) or a pharmaceutically acceptable salt thereof.

The invention further provides a method of treatment or prophylaxis of conditions for which antagonism of NK1 receptor is beneficial, in mammals including humans, which comprises administering to the sufferer a therapeutically effective amount of a compound of formula (I) or a pharmaceutically acceptable salt thereof.

The invention further provides a method of treatment or prophylaxis of the above disorders, in mammals including humans, which comprises administering to the sufferer a therapeutically effective amount of a compound of formula (I) or a pharmaceutically acceptable salt thereof.

The invention further provides a method of treatment or prophylaxis of depression, anxiety, sleep disorders or emesis in mammals including humans, which comprises administering to the suffer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of conditions mediated by tachykinins.

In another aspect, the invention provides the use of a compound of formula (I) or a pharmaceutically acceptable salt thereof in the manufacture of a medicament for use in the treatment of conditions for which antagonism of NK1 receptor is beneficial.

In another aspect, the invention provides the use of a compound of formula (I) or a pharmaceutically acceptable salt thereof in the manufacture of a medicament for use in the treatment of the above disorders.

In another aspect, the invention provides the use of a compound of formula (I) or a pharmaceutically acceptable salt thereof in the manufacture of a medicament for use in the treatment of depression, anxiety, sleep disorders or emesis.

When used in therapy, the compounds of formula (I) are usually formulated in a standard pharmaceutical composition. Such compositions can be prepared using standard procedures.

The present invention further provides a pharmaceutical composition which comprises a compound of formula (I) or a pharmaceutically acceptable salt thereof and a pharmaceutically acceptable carrier.

The present invention further provides a pharmaceutical composition for use in the treatment of the above disorders which comprises a compound of formula (I) or a pharmaceutically acceptable salt thereof and a pharmaceutically acceptable carrier.

Compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

Compounds of the invention may be used in combination with antidepressants to treat or prevent depression and mood disorders.

Compounds of the invention may be used in combination with an opioid analgesic to treat and prevent pain.

Compounds of the invention may be used in combination with the following agents to treat or prevent bipolar disease: i) mood stabilisers; ii) antipsychotics; and iii) antidepressants.

Compounds of the invention may be used in combination with the following agents to treat or prevent anxiety disorders: i) anxiolytics; and ii) antidepressants.

Compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

Compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

Compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

Compounds of the invention may be used in combination with the following agents to treat or prevent sleep disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

Compounds of the invention may be used in combination with the following agents to treat anorexia: i) appetite stimulants for example cyproheptidine; ii) antidepressants; iii) antipsychotics; iv) zinc; and v) premenstrual agents for example pyridoxine and progesterones.

Compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstrual agents.

Compounds of the invention may be used in combination with the following agents to treat or prevent autism: i) antipsychotics; ii) antidepressants; iii) anxiolytics; and iv) stimulants for example methylphenidate, amphetamine formulations and pemoline.

Compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

Compounds of the invention may be used in combination with the following agents to treat personality disorders: i) antipsychotics; ii) antidepressants; iii) mood stabilisers; and iv) anxiolytics.

Compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

Compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

Opioid analgesics include alfentanil, buprenorphine, butorphanol, carfentanil, codeine, diacetylmorphine, dihydrocodeine, fentanyl, hydrocodone, hydromorphone, levorphanol, lofentanil, meperidine, methadone, morphine, nalbuphine, oxycodone, oxymorphone, pentazocine, propoxyphenem, remifentanil and sufentanil.

Compounds of the invention may be used in combination with Na channel blockers to treat epilepsy, depression and mood disorders, psycothic disorders or pain.

Within the context of the combination with Na channel blockers, the term "epilepsy" is intended to include Seizure disorders and epilepsy syndromes. The various types of the Epilepsy and seizures mentioned hereinbelow are contemplated as part of the present invention: partial onset seizures (replacing temporal lobe epilepsy, neocortical epilepsy and Rasumssen's), generalized onset seizures, the seizures of the Lennox Gastaut syndrome (tonic, atonic, myoclonic, atypical absence and generalized tonic-clonic), absence seizure syndromes and juvenile myoclonic epilepsy.

Combination of compounds of the invention with a Na channel blocker may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Within the context of the combination with Na channel blockers the term "psychotic disorder" includes:
i) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the combination with Na channel blockers, the term "pain" includes: chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with cluster and chronic daily headache; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; dysmenorrhea; neuralgia; fibromyalgia syndrome; complex regional pain syndrome (CRPS types I and II); neuropathic pain syndromes (including diabetic neuropathy; chemotherapeutically induced neuropathic pain; sciatica; non-specific lower back pain; multiple sclerosis pain; HIV-related neuropathy; post-herpetic neuralgia; trigeminal neuralgia); and pain resulting from physical trauma, amputation, cancer, toxins or chronic inflammatory conditions.

Within the context of the combination with Na channel blockers the term "depression and mood disorder" includes Depression and mood disorders including Major Depressive Episode, Manic Episode, Mixed Episode and Hypo manic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypo manic Episodes) (296.89), Cyclothymiacs Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

In one embodiment, the "depression and mood disorder" which may be treated by administration of a combination of compounds of the invention with Na channel blockers is a bipolar disorder.

In one embodiment, the combination as herein above defined comprises a Na channel blocker selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof.

In a further embodiment, the combination as herein above defined comprises a Na channel blocker selected from the group consisting of fosphenyloin (Cerebyx™, Prodilantin™, Pro-Epanutin™ or Cereneu™), oxcarbazepine (Trileptal™, Oxrate™ or Wockhardt™) phenyloin, carbamazepine (Carbatrol, Equetro™), lidocaine (ALGRX-3268), Safinamide (NW-1015), Ralfinamide (NW-1029), lacosamide ((2R)-2-(acetylamino)-3-methoxy-N-(phenylmethyl)propanamide), and rufinamide (RUF-331).

In a further embodiment, the combination as herein above defined comprises a Na channel blocker selected from the group consisting of:
3,5-diamino-6-(2,3-dichlorophenyl)-1,2,4-triazine;
R(+2,4-diamino-5-(2,3-dichlorophenyl)-6-fluoromethylpyrimidine;
(2R,5R)-2-(4-{[(2-fluorophenyl)methyl]oxy}phenyl)-1,7-diazaspiro[4.4]nonan-6-one;
(2R,5R)-2-(4-{[(2-fluorophenyl)methyl]oxy}phenyl)-7-methyl-1,7-diazaspiro[4.4]nonan-6-one;
(5R)-5-(4-{[(2-fluorophenyl)methyl]oxy}phenyl)-L-prolinamide
or pharmaceutically acceptable salts or solvates thereof.

In an additional further embodiment, the combination as herein above defined comprises a Na channel blocker which is 3,5-diamino-6-(2,3-dichlorophenyl)-1,2,4-triazine or a pharmaceutically acceptable salt or solvate thereof.

Compound 3,5-diamino-6-(2,3-dichlorophenyl)-1,2,4-triazine and pharmaceutically acceptable salts and solvates thereof are described in EP granted Patent EP0021121B and in U.S. Pat. No. 4,602,017. Compound 3,5-diamino-6-(2,3-dichlorophenyl)-1,2,4-triazine and pharmaceutically acceptable salts and solvates thereof may be prepared by any method described in EP0021121B and U.S. Pat. No. 4,602,017.

In another embodiment, the combination as herein above defined comprises a Na Channel blocker which is R(−)-2,4-diamino-5-(2,3-dichlorophenyl)-6-fluoromethylpyrimidine or a pharmaceutically acceptable salt or solvate thereof.

Compound R(−)-2,4-diamino-5-(2,3-dichlorophenyl)-6-fluoromethylpyrimidine and pharmaceutically acceptable salts and solvates thereof are described in PCT publication No. WO 97/9317, published 13 Mar. 1997. Compound R(−)-2,4-diamino-5-(2,3-dichlorophenyl)-6-fluoromethylpyrimidine and pharmaceutically acceptable salts and solvates thereof may be prepared by any method described in WO 97/9317.

In an additional further embodiment, the combination as herein above defined comprises a Na channel blocker which is (5R)-5-(4-{[(2-fluorophenyl)methyl]oxy}phenyl)-L-prolinamide or a pharmaceutically acceptable salt or solvate thereof.

Compound (5R)-5-(4-{[(2-fluorophenyl)methyl]oxy}phenyl)-L-prolinamide and pharmaceutically acceptable salts and solvates thereof are described in PCT publication No. WO2007/042239. Compound (5R)-5-(4-{[(2-fluorophenyl)methyl]oxy}phenyl)-L-prolinamide or pharmaceutically acceptable salts and solvates thereof may be prepared by any method described in WO2007/042239.

In an additional further embodiment, the combination as herein above defined comprises a Na channel blocker which is (2R,5R)-2-(4-{[(2-fluorophenyl)methyl]oxy}phenyl)-7-methyl-1,7-diazaspiro[4.4]nonan-6-one or a pharmaceutically acceptable salt or solvate thereof. Compound (2R,5R)-2-(4-{[(2-fluorophenyl)methyl]oxy}phenyl)-7-methyl-1,7-diazaspiro[4.4]nonan-6-one and pharmaceutically acceptable salts and solvates thereof are described in PCT publication No. WO2007/042240. Compound (2R,5R)-2-(4-{[(2-fluorophenyl)methyl]oxy}phenyl)-7-methyl-1,7-diazaspiro[4.4]nonan-6-one and pharmaceutically acceptable salts and solvates thereof may be prepared by any method described in WO2007/042240.

In one embodiment, the combination of a compound of the invention with a Na channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethyl pyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and (2R,5S,7R)-$N^8$-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide or a pharmaceutically acceptable salt or solvate thereof.

The invention thus provides, in a further aspect, a combination comprising a compound of the invention together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of the invention is used in combination with a second therapeutic agent active against the same disease state the dose of each compound may differ from that when the compound is used alone. Appropriate doses will be readily appreciated by those skilled in the art.

Thus, in one embodiment, a combination of a compound of the invention with a Na channel blocker is provided, wherein at least one of them is at a sub therapeutic dose.

A subtherapeutic dose is intended to mean a dose of a drug below that required to produce significant clinical benefit for the patient when administered alone.

In one embodiment, the combination of a compound of the invention with a Na Channel blocker, comprises a Na Channel blocker, at subtherapeutic dose, which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-

5-(4-{[(2-fluorophenyl)methyl]oxy}phenyl)-L-prolinamide, or a pharmaceutically acceptable salt or solvate thereof; and a compound of the invention.

In another embodiment, the combination of a compound of the invention with a Na Channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and a compound of the invention at a sub therapeutic dose.

In a further embodiment, the combination of a compound of the invention with a Na channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and a compound of formula (I) or a pharmaceutically acceptable salt or solvate thereof; such compound of formula (I) and Na Channel blocker compound being both administered at a sub therapeutic dose.

In one embodiment, the combination of a compound of the invention with a Na Channel blocker, comprises a Na Channel blocker, at subtherapeutic dose, which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt or solvate thereof; and (2R,5S,7R)-4-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide or a pharmaceutically acceptable salt or solvate thereof.

In another embodiment, the combination of a compound of the invention with a Na Channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(+2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt or solvate thereof; and (2R,5S,7R)-$N^9$-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide or a pharmaceutically acceptable salt or solvate thereof, at a sub therapeutic dose.

In a further embodiment, the combination of a compound of the invention with a Na Channel blocker, comprises a Na Channel blocker which is selected from the group consisting of: fosphenyloin (Cerebyx™, Prodilantin™, Pro-Epanutin™ or Cereneu™); oxcarbazepine (Trileptal™, Oxrate™ or Wockhardt™); phenyloin; carbamazepine (Carbatrol, Equetro™); lidocaine (ALGRX-3268); Safinamide (NW-1015); Ralfinamide (NW-1029); lacosamide ((2R)-2-(acetylamino)-3-methoxy-N-(phenylmethyl)propanamide); rufinamide (RUF-331); 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt or solvate thereof; and (2R,5S,7R)-$N^8$-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide or a pharmaceutically acceptable salt thereof; such compound (2R,5S,7R)-$N^8$-{(1R)-1-[3,5-bis(trifluoromethyl)phenyl]ethyl}-7-(4-fluoro-2-methylphenyl)-$N^B$-methyl-1,8-diazaspiro[4.5]decane-2,8-dicarboxamide and a Na Channel blocker compound being both administered at a sub therapeutic dose.

Thus, the invention also provides a combination of a compound of the invention with a Na channel blocker compound, for use in therapy.

Thus, the invention also provides a combination of (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide or a pharmaceutically acceptable salt thereof with a Na channel blocker compound which is selected from the group consisting of: 3,5-diamino-6-(2,3-dichlorophenyl)-1,2,4-triazine, or a pharmaceutically acceptable salt or solvate thereof; R(+2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt or solvate thereof; for use as a therapeutic substance in the treatment or prophylaxis of epilepsy, depression and mood disorders, psycothic disorders or pain.

In one embodiment, the invention provides a combination of a compound of the invention with a Na channel blocker compound, for use as a therapeutic substance in the treatment or prophylaxis of epilepsy, depression and mood disorders, psychotic disorders or pain.

In an embodiment, the invention provides a combination of (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide or a pharmaceutically acceptable salt thereof with a Na channel blocker compound, which is selected from the group consisting of: 3,5-diamino-6-(2,3-dichlorophenyl)-1,2,4-triazine, or a pharmaceutically acceptable salt or solvate thereof; R(+2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide, or a pharmaceutically acceptable salt thereof; for use as a therapeutic substance in the treatment or prophylaxis of epilepsy, depression and mood disorders, psycothic disorders or pain.

The invention further provides a method of treatment or prophylaxis of epilepsy, depression and mood disorders, psychotic disorders or pain, in mammals including humans, which comprises administering to the sufferer a therapeutically effective amount of a combination of a compound of the invention with a Na channel blocker compound.

The invention further provides a method of treatment or prophylaxis of epilepsy, depression and mood disorders, psychotic disorders or pain, in mammals including humans, which comprises administering to the sufferer a therapeutically effective amount of a combination of (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide
or a pharmaceutically acceptable salt thereof with a Na channel blocker compound, which is selected from the group consisting of: 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt thereof.

In another aspect, the invention provides the use of a combination of a compound of the invention with a Na channel blocker compound in the manufacture of a medicament for use in the treatment of epilepsy, depression and mood disorders, psychotic disorders or pain.

In another aspect, the invention provides the use of a combination of (2R,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide or a pharmaceutically acceptable salt thereof with a Na channel blocker compound, which is selected from the group consisting of: 3,5-diamino-6-(2,3-dichlorophenyl)-1,2,4-triazine, or a pharmaceutically acceptable salt or solvate thereof; R(−)-2,4-diamino-5-(2,3-dichlorophenyl)-6-fluoromethylpyrimidine, or a pharmaceutically acceptable salt or solvate thereof; (2R,5R)-2-(4-{[(2-fluorophenyl)methyl]oxy}phenyl)-1,7-diazaspiro[4.4]nonan-6-one, or a pharmaceutically acceptable salt or solvate thereof; (2R,5R)-2-(4-{[(2-fluorophenyl)methyl]oxy}phenyl)-7-methyl-1,7-diazaspiro[4.4]nonan-6-one, or a pharmaceutically acceptable salt or solvate thereof, and (5R)-5-(4-{[(2-fluorophenyl)methyl]oxy}phenyl)-L-prolinamide or a pharmaceutically acceptable salt thereof, in the manufacture of a medicament for use in the treatment of epilepsy, depression and mood disorders, psychotic disorders or pain.

When used in therapy, combinations of a compound of the invention with a Na channel blocker compound are usually formulated in a standard pharmaceutical composition. Such compositions can be prepared using standard procedures.

The present invention further provides a pharmaceutical composition which comprises a combination of a compound of the invention with a Na channel blocker compound and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or a pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration.

The compound can be sterilised by exposure to ethylene oxide before suspension in a sterile vehicle. Advantageously, a surfactant or wetting agent is included in the composition to facilitate uniform distribution of the compound.

Compositions suitable for transdermal administration include ointments, gels and patches.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

Experimental

The following Intermediates and Examples illustrate the preparation of compounds of the invention.

In the procedures that follow, after each starting material, reference to a description is typically provided. This is provided merely for assistance to the skilled chemist. The starting material may not necessarily have been prepared from the batch referred to.

The yields were calculated assuming that products were 100% pure if not stated otherwise.

Compounds are named using ACD/Name PRO 6.02 chemical naming software (Advanced Chemistry Development Inc., Toronto, Ontario, M5H2L3, Canada).

Proton Magnetic Resonance (NMR) spectra were recorded either on Varian instruments at 300, 400, 500 or 600 MHz, or on a Bruker instrument at 300 MHz and 400 MHz. Chemical shifts are reported in ppm ($\delta$) using the residual solvent line as internal standard. Splitting patterns are designed as s, singlet; d, doublet; t, triplet; q, quartet; m, multiplet; b, broad. The NMR spectra were recorded at a temperature ranging from 25 to 90° C. When more than one conformer or isomer was detected the chemical shifts for the most abundant one are reported.

Total ion current (TIC) and DAD UV chromatographic traces together with MS and UV spectra associated with the peaks were taken on a UPLC/MS Acquity™ system equipped with 2996 PDA detector and coupled to a Waters Micromass ZQ™ mass spectrometer operating in positive or negative electrospray ionisation mode [LC/MS-ES (+ or −): analyses performed using an Acquity™ UPLC BEH C18 column (50× 2.1 mm, 1.7 µm particle size). Mobile phase: A—water+0.1% $HCO_2H$/B—$CH_3CN$+0.06% $HCO_2H$. Gradient: t=0 min 3% B, t=0.05 min 6% B, t=0.57 min 70% B, t=1.06 min 99% B lasting for 0.389 min, t=1.45 min 3% B, stop time 1.5 min. Column T=40° C. Flow rate=1.0 mL/min. Mass range: ES (+): 100-1000 amu. ES (−): 100-800 amu. UV detection range: 210-350 nm. The usage of this methodology is indicated by "UPLC" in the analytic characterization of the described compounds.

HPLC analysis indicated by R(HPLC): x min, was performed on an Agilent 1100 series instrument using a Luna 3 u C18(2) 100 A (50×2.0 mm) column (mobile phase: 100% [water+0.05% TFA] to 95% [acetonitrile+0.05% TFA] in 8 min, flux=1 ml/min, detection wavelength 220 nm. The usage of this methodology is indicated by "HPLC" in the analytic characterization of the described compounds.

Direct infusion Mass spectra (MS) were run on a Agilent MSD 1100 Mass Spectrometer, operating in ES (+) and ES (−) ionization mode [ES (+): Mass range: 100-1000 amu. Infusion solvent: water+0.1% $HCO_2H$/$CH_3CN$ 50/50. ES (−): Mass range: 100-1000 amu. Infusion solvent: water+ 0.05% $NH_4OH$/$CH_3CN$ 50/50] (the usage of this methodology is indicated by "MS" in the analytic characterization of the described compounds) or on an Agilent LC/MSD 1100 Mass Spectrometer coupled with HPLC instrument Agilent 1100 Series, operating in positive or negative electrospray ionization mode and in both acidic and basic gradient conditions [Acidic gradient LC/MS-ES (+ or −): analyses performed on a Supelcosil ABZ+Plus column (33×4.6 mm, 3 µm). Mobile phase: A—water+0.1% $HCO_2H$/B—$CH_3CN$. Gradient (standard method): t=0 min 0% (B), from 0% (B) to 95% (B) in 5 min lasting for 1.5 min, from 95% (B) to 0% (B) in 0.1 min, stop time 8.5 min. Column T=r.t. Flow rate=1 mL/min. Gradient (fast method): t=0 min 0% (B), from 0% (B) to 95% (B) in 3 min lasting for 1 min, from 95% (B) to 0% (B) in 0.1 min, stop time 4.5 min. Column T=r.t. Flow rate=2 mL/min. Basic gradient LC/MS-ES (+ or −): analyses performed on a XTerra MS C18 column (30×4.6 mm, 2.5 µm). Mobile phase: A—5 mM aq. $NH_4HCO_3$+ammonia (pH 10)/ B—$CH_3CN$. Gradient: t=0 min 0% (B), from 0% (B) to 50% (B) in 0.4 min, from 50% (B) to 95% (B) in 3.6 min lasting for 1 min, from 95% (B) to 0% (B) in 0.1 min, stop time 5.8 min. Column T=r.t. Flow rate=1.5 mL/min]. Mass range ES (+ or −): 100-1000 amu. UV detection range: 220-350 nm (the usage of this methodology is indicated by "LC/MS acidic or basic gradient conditions" in the analytic characterization of the described compounds)

For reactions involving microwave irradiation, a Personal Chemistry Emrys™ Optimizer was used.

Flash silica gel chromatography was carried out on silica gel 230-400 mesh (supplied by Merck AG Darmstadt, Germany) or over Varian Mega Be-Si pre-packed cartridges or over pre-packed Biotage silica cartridges or over pre-packed RediSep silica cartridges.

SPE-SCX cartridges are ion exchange solid phase extraction columns by supplied by Varian. The eluent used with SPE-SCX cartridges is methanol followed by 2N ammonia solution in methanol.

In a number of preparations purification was performed using either Biotage manual flash chromatography (Flash+) or automatic flash chromatography on SPX (Biotage) system using Biotage Silica cartridges, or automatic flash chromatography on Companion CombiFlash (ISCO) using RediSep Silica cartridges.

SPE-Si cartridges are silica solid phase extraction columns supplied by Varian.

Diastereoisomer 1 or Diastereoisomer 2 means a compound of the invention or an intermediate thereof as a single diastereoisomer whose absolute configuration at one stereocentre was not determined and this stereocentre is marked as "U"

The following table lists the abbreviations used:

| | |
|---|---|
| BOC-Anhydride | Di-tert-butyl dicarbonate |
| Cy | Cyclohexane |
| THF | Tetrahydrofuran |
| EtOAc | Ethyl acetate |
| CH3CN | Acetonitrile |
| DCM | Dichloromethane |
| DBU | 1,8-Diazabicyclo[5.4.0]undec-7-ene |
| Et2O | Diethyl ether |
| HCl | Hydrochloric acid |
| H2 | Hydrogen |
| LiCl | Lithium chloride |
| LiOH•H2O | Lithium hydroxide monohydrate |
| LiHMDS | Lithium bis(trimethylsilyl)amide |
| mCPBA | 3-Chloroperbenzoic acid |
| MeOH | Methanol |
| $Na_2SO_4$ | Sodium sulfate |
| $Na_2S_2O_3$ | Sodium thiosulfate |
| $NaHCO_3$ | Sodium bicarbonate |
| Na2HPO4 | Sodium phosphate dibasic |
| NH4Cl | Ammonium chloride |
| Pd/C | Palladium on carbon |
| Si | Silica |
| TEA | Triethylamine |
| THF | Tetrahydrofuran |
| TFA | Trifluoroacetic acid |
| DMSO | Dimethyl sulfoxide |
| $NH_3$ | Ammonia |
| min | minute |
| hr | hour |
| rt | Room temperature |
| P | pressure |
| Rt | Retention time |
| ax | axial |
| eq | equatorial |
| BOC-Anhydride | Di-tert-butyl dicarbonate |
| Cy | Cyclohexane |
| THF | Tetrahydrofuran |
| EtOAc | Ethyl acetate |
| CH3CN | Acetonitrile |
| DCM | Dichloromethane |
| DBU | 1,8-Diazabicyclo[5.4.0]undec-7-ene |
| Et2O | Diethyl ether |
| HCl | Hydrochloric acid |
| H2 | Hydrogen |
| LiCl | Lithium chloride |
| CD | Circular dicroism |
| HPLC | High Performance Liquid Chromatography |
| UPLC | Ultra Performance Liquid Chromatography |
| DAD | Diode Array Detector |

Intermediate 1

(2R)-N-{(1R)-1-[3,5-bis(trifluoromethyl)phenyl]
ethyl}-{[1,1-dimethylethyl)sulfinyl]imino}-2-(4-
fluoro-2-methylphenyl)-N-methyl-1-piperidinecar-
boxamide

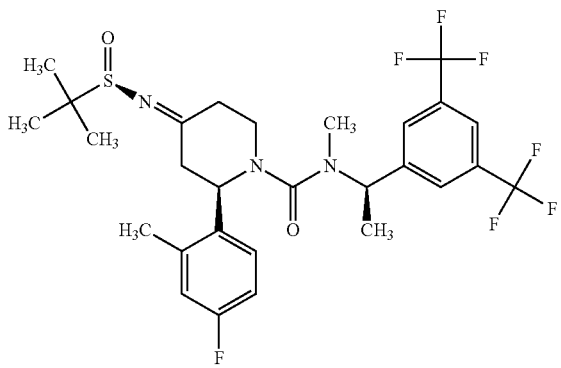 [SMILES: Cc1cc(F)ccc1[C@H]1CC(=N[S@](=O)C(C)(C)C)CCN1C(=O)N(C)[C@H](C)c1cc(C(F)(F)F)cc(C(F)(F)F)c1]

To a solution of (2R)-N-{(1R)-1-[3,5-bis(trifluoromethyl)phenyl]ethyl}-2-(4-fluoro-2-methylphenyl)-N-methyl-4-oxo-1-piperidinecarboxamide (WO0232867) (4 g, 7.93 mmol) and Titanium(IV) ethoxide (8 mL) in THF (10 mL) was added at 25° C., under Nitrogen, (R)-(+)-2-Methyl-2-propanesulfinamide (1.15 g, 9.52 mmol, Aldrich) and the reaction mixture was heated to 100° C. It was stirred at this temperature for 3 hrs, then it was diluted with DCM and brine (2 mL) was added. A white precipitate was formed and it was filtered-off. The resulting solution was dried ($Na_2SO_4$) and evaporated to dryness. The crude was purified by silica cartridge (25 g) (from 1:0 to 0:1 Cyclohexane/EtOAc) to give the title compound (2.2 g, 3.62 mmol, 45% yield) as a yellow gum. A further purification of the crude fractions containing the desired compound by flash chromatography on Companion CombiFlash (from 1:0 to 0:1 Cyclohexane/EtOAc) gave further title compound (848 mg, 1.40 mmol, 17.6% yield). 1H NMR (500 MHz, DMSO-d6) δ ppm 7.68-8.07 (m, 3H) 6.70-7.43 (m, 3H) 4.80-5.35 (m, 2H) 3.10-3.79 (m, 2H) 2.42-2.95 (m, 7H) 2.19-2.30 (m, 3H) 1.46-1.62 (m, 3H) 1.01-1.22 (m, 9H); mixture of E+Z isomers Intermediates 2 and 3

(2R,4R)-N-{(1R)-1-[3,5-bis(trifluoromethyl)phenyl]
ethyl}-4-{[(1,1-dimethylethyl)sulfinyl]amino}-2-(4-
fluoro-2-methylphenyl)-N-methyl-4-(2-propen-1-yl)-
1-piperidinecarboxamide (2) and (2R,4S)-N-{(1R)-1-[3,5-bis(trifluoromethyl)phenyl]
ethyl}-4-{[(1,1-dimethylethyl)sulfinyl]amino}-2-(4-
fluoro-2-methylphenyl)-N-methyl-4-(2-propen-1-yl)-
1-piperidinecarboxamide (3)

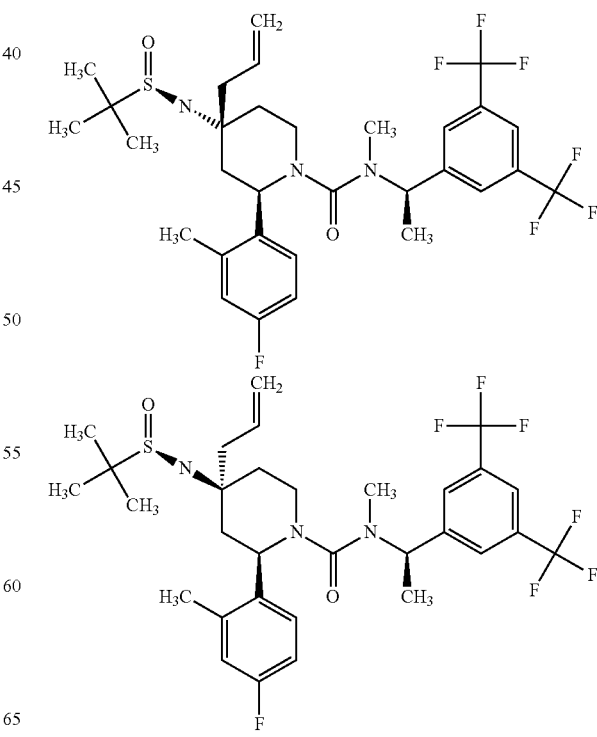

To a suspension of (2R)-N-{(1R)-1-[3,5-bis(trifluoromethyl)phenyl]ethyl}-4-{[(1,1-dimethylethyl)sulfinyl]imino}-2-(4-fluoro-2-methylphenyl)-N-methyl-1-piperidinecarboxamide (Intermediate 1, 50 mg, 0.082 mmol) and Zinc powder (16.14 mg, 0.247 mmol, Aldrich) in THF (1.5 mL) was added at 25° C. allyl bromide (0.021 mL, 0.247 mmol, Aldrich) and the reaction mixture was stirred at this temperature for 16 hrs. Brine and EtOAc were added and the resulting mixture was filtrated over Celite® and the two phases were separated. The aqueous phase was extracted with EtOAc (3×) and the combined organic phases were dried over $Na_2SO_4$ and evaporated to dryness. The crude was purified by flash chromatography on silica with SP1 (Biotage) system (from 1:0 to 0:1 Cyclohexane/EtOAc; 25M Si cartridge) to give two different products:

($1^{st}$ eluted) (Intermediate 2) (2R,4R)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-propen-1-yl)-1-piperidinecarboxamide (17.3 mg, 0.026 mmol, 32% yield) as a white solid. 1H NMR (500 MHz, DMSO-d6) δ ppm 7.98 (s, 1H) 7.67 (s, 2H) 7.09-7.18 (m, 1H) 6.88 (dd, 1H) 6.73 (t, 1H) 5.84-6.01 (m, 1H) 5.27-5.39 (m, 1H) 4.98-5.09 (m, 2H) 4.94 (s, 1H) 4.48 (d, 1H) 3.16 (d, 1H) 3.03 (t, 1H) 2.66 (s, 3H) 2.35 (s, 3H) 2.26-2.43 (m, 2H) 2.00 (d, 1H) 1.85 (t, 1H) 1.77 (d, 1H) 1.45 (d, 3H) 1.34-1.59 (m, 1H) 1.14-1.24 (m, 9H). 27(R), 10(R), 6(R), C(15) NH(9) trans: the relative stereochemistry trans was confirmed by dipolar correlation between $CH(6)_{ax}$ to $CH_2(2)_{ax}$ and NH(9); The atom numbering shown in the following structure is included for the purpose of correlation with the NMR data only.

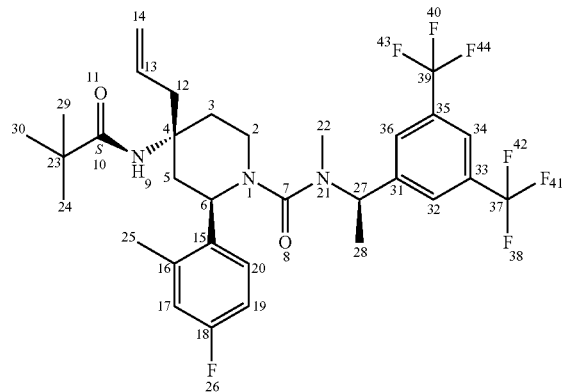

($2^{nd}$ eluted) (Intermediate 3) (2R,4S)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-propen-1-yl)-1-piperidinecarboxamide (11.2 mg, 0.017 mmol, 21% yield) as a colourless oil. 1H NMR (500 MHz, DMSO-d6) δ ppm 7.99 (s, 1H) 7.68 (s, 2H) 7.11-7.20 (m, 1H) 6.91 (dd, 1H) 6.77 (t, 1H) 5.82-5.98 (m, 1H) 5.25-5.33 (m, 1H) 5.09-5.24 (m, 2H) 4.90 (s, 1H) 4.34-4.42 (m, 1H) 3.26-3.39 (m, 1H) 2.93-3.05 (m, 1H) 2.70 (s, 3H) 2.59 (d, 2H) 2.30 (s, 3H) 2.00 (t, 1H) 1.77 (d, 1H) 1.70 (d, 2H) 1.48 (d, 3H) 1.09 (s, 9H). 27(R), 10(R), 6(R), C(15) NH(9) cis: the relative stereochemistry cis was confirmed by dipolar correlation between $CH(6)_{ax}$ to $CH_2(2)_{ax}$ and $CH_2(12)$; The atom numbering shown in the following structure is included for the purpose of correlation with the NMR data only.

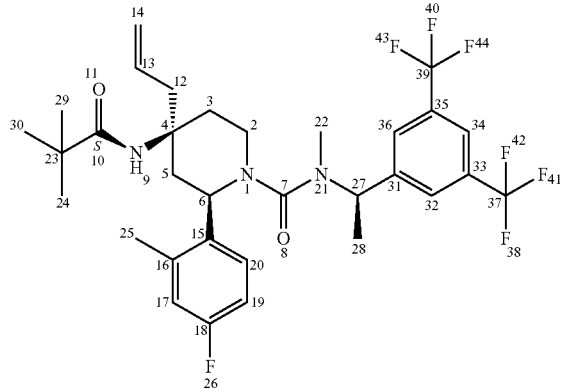

Intermediate 4

(2R,4R)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-oxoethyl)-1-piperidinecarboxamide

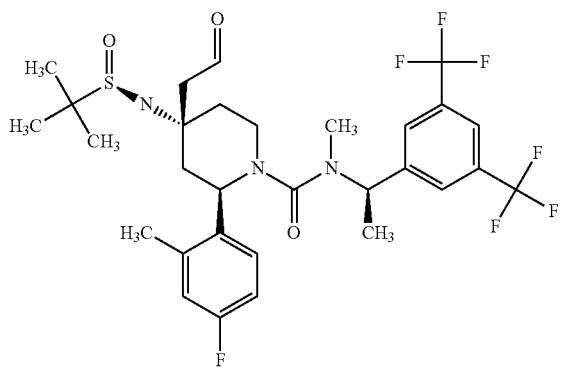 [SMILES: Cc1cc(F)ccc1[C@H]1C[C@](CC=O)(N[S@](=O)C(C)(C)C)CCN1C(=O)N(C)[C@H](C)c1cc(C(F)(F)F)cc(C(F)(F)F)c1]

The starting material used in this step was prepared using the same procedure described before and it was used in two reactions in parallel that were combined together for the final purification. A solution of (2R,4R)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-propen-1-yl)-1-piperidinecarboxamide (Intermediate 2, 500 mg, 0.77 mmol) in DCM (50 mL) was cooled to −78° C. and ozone was bubbled through the stirred reaction mixture for 10 mins. The reaction was stirred under a nitrogen atmosphere and Dimethyl sulfide (10 mL, 135 mmol) was added at −78° C. The resulting mixture was stirred for 16 hrs to quench residual ozonide.

In the meantime the same reaction was performed on the second part of material. A solution of (2R,4R)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-propen-1-yl)-1-piperidinecarboxamide (Intermediate 2, 480 mg, 0.739 mmol) in DCM (48 mL) was cooled to −78° C. and ozone was bubbled through the stirred reaction mixture for 10 mins. The reaction was stirred under a nitrogen atmosphere and Dimethyl sulfide (10 mL, 135 mmol) was added at −78° C. The resulting mixture was stirred for 16 hrs to quench residual ozonide.

The two reactions mixtures were combined together and the solvent was evaporated to dryness. The crude was purified by flash chromatography on silica with SP1 (Biotage) system (from 1:0 to 0:1 Cyclohexane/EtOAc; 40M Si cartridge) to give the title compound (587 mg, 0.90 mmol, 60% yield) as a yellow oil (the yield was calculated considering the sum of the two amounts of starting material used). 1H NMR (400 MHz, DMSO-$d_6$) δ ppm 9.68-9.83 (s, 1H) 7.91-8.05 (m, 1H) 7.55-7.75 (m, 2H) 7.09-7.23 (m, 1H) 6.83-6.95 (m, 1H) 6.65-6.80 (m, 1H) 5.26-5.43 (m, 1H) 5.17-5.26 (m, 1H) 4.45-4.55 (m, 1H) 3.10-3.25 (m, 1H) 2.96-3.10 (m, 1H) 2.56-2.81 (m, 5H) 2.27-2.41 (m, 3H) 2.14-2.25 (m, 1H) 1.89-2.05 (m, 2H) 1.56-1.72 (m, 1H) 1.47 (d, 3H) 1.12-1.29 (m, 9H). UPLC: Rt 0.92 mins, m/z 652 [M+H]$^+$.

Intermediate 5

Methyl 4-[(2R,4R)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-{[(1,1-dimethylethyl)(dimethyl)silyl]oxy}-2-butenoate

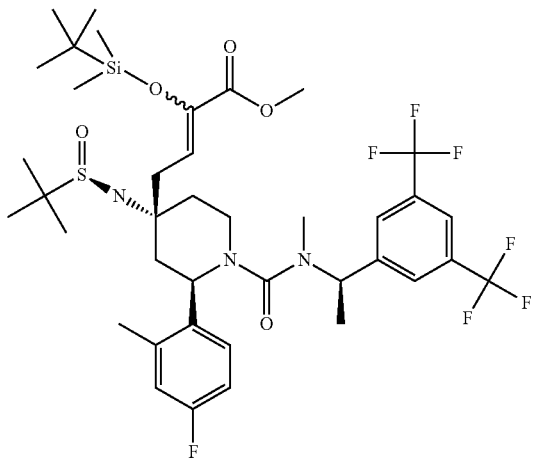 [SMILES: COC(=O)C(=CC[C@@]1(N[S@](=O)C(C)(C)C)CCN(C(=O)N(C)[C@H](C)c2cc(C(F)(F)F)cc(C(F)(F)F)c2)[C@@H](c2ccc(F)cc2C)C1)O[Si](C)(C)C(C)(C)C]

1,8-Diazabicyclo[5.4.0]undec-7-ene (0.185 mL, 1.24 mmol, Aldrich) was added dropwise to a suspension of Lithium chloride (55.6 mg, 1.31 mmol, Aldrich) and Methyl [bis(methyloxy)phosphoryl]{[(1,1-dimethylethyl)(dimethyl)silyl]oxy}acetate (*Tetrahedron Lett.* 1981, 22, 663-666) (409 mg, 1.31 mmol) in dry Acetonitrile (20 mL) and the mixture was maintained at 0° C. for 1 h. A solution of (2R,4R)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-oxoethyl)-1-piperidinecarboxamide (Intermediate 4, 585 mg, 0.898 mmol) in Acetonitrile (5 mL) was added dropwise at 0° C. The mixture was stirred for 7 hours while the temperature was allowed to increase to 25° C. Saturated aqueous NaHCO$_3$ and EtOAc were added to the reaction mixture and the two phases were separated. The combined organic phases were dried (Na$_2$SO$_4$), and evaporated to dryness. The crude was purified by flash chromatography on silica with SP1 (Biotage) system (from 1:0 to 0:1 Cyclohexane/EtOAc) to give the title compound (542 mg, 0.65 mmol, 72% yield) as a white solid.

1H NMR (400 MHz, DMSO-$d_6$) δ ppm 7.89-8.07 (m, 1H) 7.56-7.76 (m, 2H) 7.03-7.19 (m, 1H) 6.82-6.96 (m, 1H) 6.57-6.80 (m, 1H) 5.59-5.80 (m, 1H) 5.23-5.40 (m, 1H) 4.98-5.18 (m, 1H) 4.38-4.59 (m, 1H) 3.57-3.71 (m, 3H) 3.12-3.22 (m, 1H) 2.98-3.11 (m, 1H) 2.74-2.87 (m, 1H) 2.59-2.74 (m, 4H) 2.28-2.41 (m, 3H) 1.94-2.12 (m, 1H) 1.72-1.94 (m, 2H) 1.54-1.73 (m, 1H) 1.40-1.54 (m, 3H) 1.11-1.29 (m, 9H) 0.80-0.94 (m, 9H) 0.03-0.13 (m, 6H). UPLC: Rt 1.19 mins, m/z=838 [M+H]$^+$ and 860 [M+Na]$^+$.

Intermediate 6

Methyl 4-[(2R,4R)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-oxobutanoate

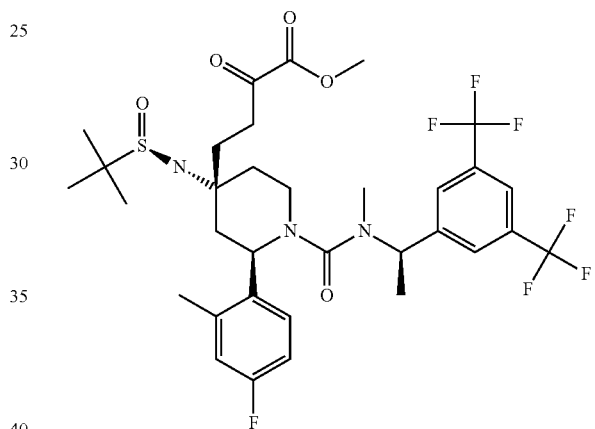

To a solution of Methyl 4-[(2R,4R)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-{[(1,1-dimethylethyl)(dimethyl)silyl]oxy}-2-butenoate (intermediate 5, 100 mg, 0.119 mmol) and Acetic acid (0.014 mL, 0.239 mmol) in Acetonitrile (2 mL) was added Cesium Fluoride (58.0 mg, 0.382 mmol, Aldrich) and the reaction mixture was stirred at 25° C. for 5 hrs. NaHCO$_3$ saturated solution was added very carefully and the mixture was extracted with EtOAc (3×). The combined organic phases were dried (Na$_2$SO$_4$) and evaporated to dryness. The crude was purified by flash chromatography on silica with SP1 (Biotage) system (from 1:0 to 0:1 Cyclohexane/EtOAc) to give the title compound (64.4 mg, 0.089 mmol, 75% yield) as a white foam. 1H NMR (400 MHz, DMSO-$d_6$) δ ppm 7.97 (s, 1H) 7.58-7.72 (m, 2H) 7.08-7.22 (m, 1H) 6.88 (d, 1H) 6.70 (t, 1H) 5.25-5.38 (m, 1H) 5.03 (s, 1H) 4.35-4.50 (m, 1H) 3.72 (s, 3H) 2.86-3.22 (m, 4H) 2.65 (s, 3H) 2.36 (s, 3H) 1.44 (d, 3H) 1.32-2.12 (m, 6H) 1.19 (s, 9H). The sample consists of two species ratio ~70:30 (see signals of OMe at 3.71 ppm, 3.66 ppm). UPLC: 2 peaks Rt 0.87 and 0.93 mins with the expected mass m/z=724 [M+H]$^+$.

Intermediates 7 and 8

Methyl(5R,7R)-8-{[{(1R)-1-[3,5 bis(trifluoromethyl)phenyl]ethyl}(methyl)amino]carbonyl}-7-(4-fluoro-2-methylphenyl)-1,8-diazaspiro[4.5]decane-2-carboxylate(7) (diastereoisomer 1) and Methyl(5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (8) (diastereoisomer 2)

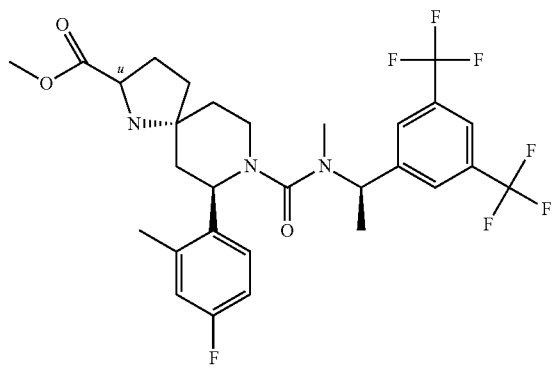

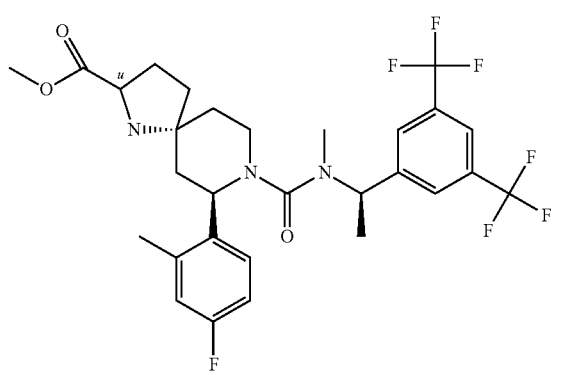

To a solution of Methyl 4-[(2R,4R)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-oxobutanoate (Intermediate 6, 62 mg, 0.086 mmol) in DCM (1 mL) was added TFA (4 mL, 51.9 mmol) and the reaction mixture was stirred at 25° C. for 6 hrs. Triethylsilane (1 mL, 6.26 mmol, Aldrich) was added to the reaction mixture and it was stirred for 1 hr. The reaction mixture was left still overnight and the day after it was poured very carefully in a NaHCO₃ saturated solution to be neutralised and DCM was added. The two phases were separated, the aqueous layer was extracted with DCM (3×) and the combined organic phases were dried and evaporated to dryness. The crude was purified by flash chromatography on silica with SP1 (Biotage) system (from 1:0 to 0:1 Cyclohexane/EtOAc) to give the two diastereoisomers:

(1$^{st}$ eluted) (Intermediate 7) (diastereoisomer 1) Methyl (5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (10.6 mg, 0.017 mmol, 20% yield) as a yellowish gum.

1H NMR (400 MHz, DMSO-d₆) δ ppm 7.90-8.09 (m, 1H) 7.61-7.75 (m, 2H) 7.10-7.22 (m, 1H) 6.67-6.95 (m, 2H) 5.21-5.40 (m, 1H) 4.29-4.46 (m, 1H) 3.75-3.94 (m, 1H) 3.55-3.68 (m, 3H) 3.13-3.26 (m, 1H) 2.96-3.12 (m, 1H) 2.64-2.81 (m, 3H) 2.26-2.38 (m, 3H) 2.00-2.16 (m, 1H) 1.68-1.91 (m, 2H) 1.35-1.67 (m, 8H) (2$^{nd}$ eluted) (Intermediate 8) (diastereoisomer 2) Methyl (5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (20.8 mg, 0.034 mmol, 40% yield) as a colourless gum. 1H NMR (400 MHz, DMSO-d₆) δδ ppm 7.96-8.02 (m, 1H) 7.65-7.73 (m, 2H) 7.11-7.19 (m, 1H) 6.85-6.94 (m, 1H) 6.69-6.80 (m, 1H) 5.27-5.39 (m, 1H) 4.36-4.46 (m, 1H) 3.77-3.87 (m, 1H) 3.59-3.66 (m, 3H) 3.13-3.22 (m, 1H) 2.94-3.05 (m, 1H) 2.68-2.77 (m, 3H) 2.29-2.38 (m, 3H) 1.38-2.14 (m, 11H).

Intermediate 9

(2R,4S)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-oxoethyl)-1-piperidinecarboxamide

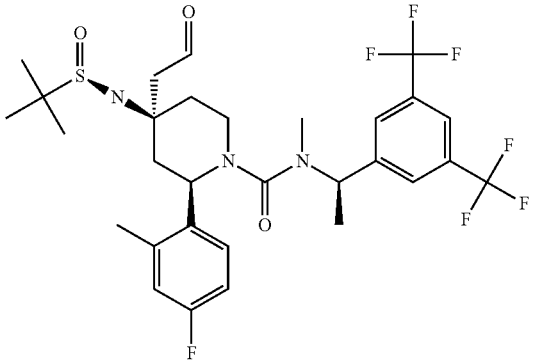 [SMILES: Cc1cc(F)ccc1[C@H]1C[C@@](CC=O)(N[S@](=O)C(C)(C)C)CCN1C(=O)N(C)[C@H](C)c1cc(C(F)(F)F)cc(C(F)(F)F)c1]

The starting material used in this step was prepared with the same procedure described before. A solution of (2R,4S)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-propen-1-yl)-1-piperidinecarboxamide (Intermediate 3, 800 mg, 1.23 mmol) in DCM (80 mL) was cooled to −78° C. and ozone was bubbled through the stirred reaction mixture for 10 mins. The reaction was stirred under a nitrogen atmosphere and Dimethyl sulfide (10 mL, 135 mmol) was added at −78° C. The resulting mixture was stirred for 16 hrs to quench residual ozonide. The mixture was evaporated to dryness and the residue was purified by flash chromatography on silica with SP1 (Biotage) system (from 1:0 to 0:1 Cyclohexane/EtOAc; 40M cartridge) to give the title compound (380 mg, 0.58 mmol, 47% yield) as a yellowish solid. 1H NMR (400 MHz, DMSO-d₆) δ ppm 9.70-9.82 (m, 1H) 7.92-8.06 (m, 1H) 7.62-7.76 (m, 2H) 7.11-7.23 (m, 1H) 6.88-6.97 (m, 1H) 6.73-6.83 (m, 1H) 5.17-5.38 (m, 2H) 4.32-4.47 (m, 1H) 2.59-3.48 (m, 7H) 2.24-2.39 (m, 3H) 1.55-2.19 (m, 4H) 1.41-1.53 (m, 3H) 0.98-1.29 (m, 9H). UPLC: Rt 0.91 mins, m/z=652 [M+H]⁺ and 674 [M+Na]⁺.

Intermediate 10

Methyl 4-[(2R,4S)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-{[(1,1-dimethylethyl)(dimethyl)silyl]oxy}-2-butenoate

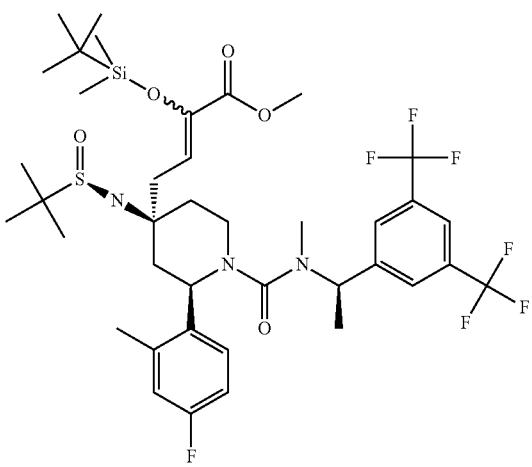 [SMILES: COC(=O)C(=CC[C@]1(N[S@](=O)C(C)(C)C)CCN(C(=O)N(C)[C@H](C)c2cc(C(F)(F)F)cc(C(F)(F)F)c2)[C@@H](c2ccc(F)cc2C)C1)O[Si](C)(C)C(C)(C)C]

1,8-Diazabicyclo[5.4.0]undec-7-ene (0.12 mL, 0.80 mmol, Aldrich) was added dropwise to a suspension of Lithium chloride (35.9 mg, 0.847 mmol, Aldrich) and Methyl [bis(methyloxy)phosphoryl]{[(1,1-dimethylethyl)(dimethyl)silyl]oxy}acetate (*Tetrahedron Lett.* 1981, 22, 663-666) (265 mg, 0.847 mmol) in dry Acetonitrile (16 mL) and the mixture was maintained at 0° C. for 1 h. A solution of (2R,4S)-N-{(1R)-1-[3,5-bis(trifluoromethyl)phenyl]ethyl}-4-{[(1,1-dimethylethyl)sulfinyl]amino}-2-(4-fluoro-2-methylphenyl)-N-methyl-4-(2-oxoethyl)-1-piperidinecarboxamide (Intermediate 9, 378 mg, 0.58 mmol) in Acetonitrile (5 mL) was added dropwise at 0° C. The mixture was stirred for 7 hours while the temperature was allowed to increase to 25° C. Saturated aqueous NaHCO$_3$ and EtOAc were added to the reaction mixture and the two phases were separated. The combined organic phases were dried (Na$_2$SO$_4$) and evaporated to dryness. The crude was purified by flash chromatography on silica with SP1 (Biotage) system (from 1:0 to 0:1 Cyclohexane/EtOAc) to give the title compound (186 mg, 0.22 mmol, 38% yield) as a white foam. 1H NMR (500 MHz, DMSO-d$_6$) δ ppm 7.98 (m, 1H) 7.68 (s, 2H) 7.12-7.20 (m, 1H) 6.92 (d, 1H) 6.79 (t, 1H) 5.66 (t, 1H) 5.26-5.35 (m, 1H) 5.00 (s, 1H) 4.33 (d, 1H) 3.71 (s, 3H) 2.70 (s, 3H) 2.60-3.4 (m, 4H) 2.27 (s, 3H) 1.48 (d, 3H) 1.35-2.10 (m, 4H) 1.05-1.13 (m, 9H) 0.84-0.98 (m, 9H) 0.06 (s, 6H). The sample consists of two species ratio ~3:1 most probably E and Z isomers (see the signals of OMe at 3.71 ppm). UPLC: 2 close peaks Rt 0.86 and 0.89 mins, m/z=838 [M+H]$^+$.

Intermediate 11

Methyl 4-[(2R,4S)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-oxobutanoate

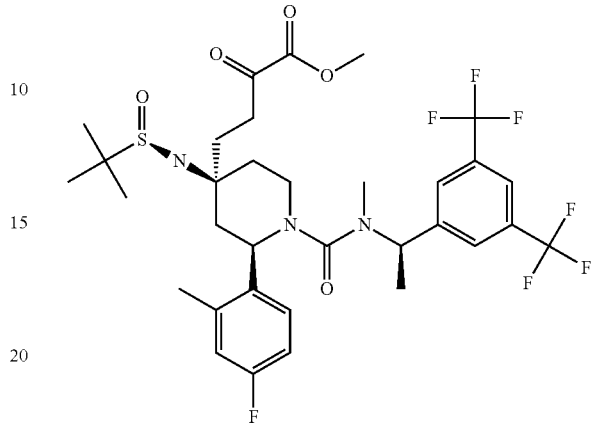

To a solution of Methyl 4-[(2R,4S)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-{[(1,1-dimethylethyl)(dimethyl)silyl]oxy}-2-butenoate (Intermediate 10, 184 mg, 0.220 mmol) and Acetic acid (0.025 mL, 0.439 mmol) in Acetonitrile (4 mL) was added Cesium Fluoride (107 mg, 0.703 mmol, Aldrich) and the reaction mixture was stirred at 25° C. for 5 hrs. NaHCO$_3$ saturated solution was added very carefully and the mixture was extracted with EtOAc (3×). The combined organic phases were dried (Na$_2$SO$_4$) and evaporated to dryness. The crude was purified by flash chromatography on silica with SP1 (Biotage) system (from 1:0 to 0:1 Cyclohexane/EtOAc) to give the title compound (108 mg, 0.149 mmol, 68% yield) as a colourless oil. 1H NMR (400 MHz, DMSO-d$_6$) δ ppm 7.92-8.03 (m, 1H) 7.62-7.75 (m, 2H) 6.68-7.30 (m, 3H) 5.20-5.37 (m, 1H) 4.94-5.07 (m, 1H) 4.30-4.46 (m, 1H) 3.67-3.81 (m, 3H) 2.86-3.07 (m, 2H) 1.58-2.77 (m, 14H) 1.45-1.53 (m, 3H) 1.03-1.12 (m, 9H). Mixture of two species (see the signals of OMe at 3.77 ppm, 3.70 ppm). UPLC: 2 peaks Rt 0.87 and 0.93 mins, m/z=724 [M+H]$^+$.

Intermediates 12 (Method A) and 13

Methyl (2R,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (12) and Methyl (2S,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (13)

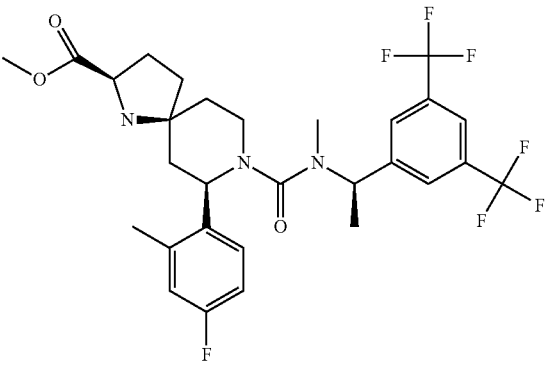

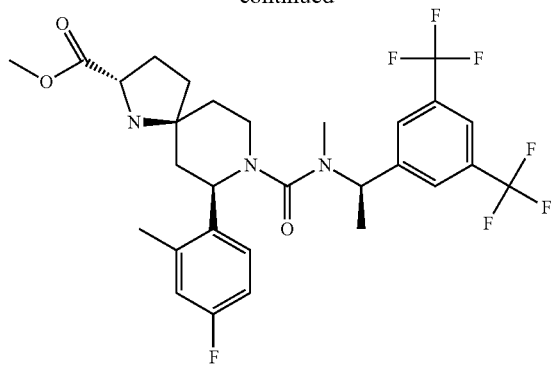

To a solution of Methyl 4-[(2R,4S)-1-{[{(1R)-1-[3,5-bis(trifluoromethyl)phenyl]ethyl}(methyl)amino]carbonyl}-4-{[(1,1-dimethylethyl)sulfinyl]amino}-2-(4-fluoro-2-methylphenyl)-4-piperidinyl]-2-oxobutanoate (Intermediate 11, 106 mg, 0.146 mmol) in DCM (2 mL) was added TFA (2 mL, 104 mmol) and the reaction mixture was stirred at 25° C. for 5.5 hrs. Triethylsilane (1 mL, 6.26 mmol) was added to the reaction mixture and it was stirred for 1 hr, then it was left still overnight. The reaction mixture was poured very carefully in a NaHCO₃ saturated solution and DCM was added. The two phases were separated, the aqueous layer was extracted with DCM (3×) and the combined organic phases were dried and evaporated to dryness. The crude was purified by silica cartridge (2 g) (from 1:0 to 0:1 Cyclohexane/EtOAc) to give the two diastereoisomers:

(1st eluted) (Intermediate 12 Method A) (diastereoisomer 1) Methyl (2R,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (22.8 mg, 0.038 mmol, 26% yield) as a colourless oil. 1H NMR (400 MHz, DMSO-d₆) δ ppm 7.92-8.10 (m, 1H) 7.65-7.74 (m, 2H) 7.09-7.19 (m, 1H) 6.88-6.95 (m, 1H) 6.72-6.82 (m, 1H) 5.24-5.38 (m, 1H) 4.09-4.19 (m, 1H) 3.70-3.80 (m, 1H) 3.57-3.66 (m, 3H) 2.65-3.46 (m, 5H) 2.25-2.39 (m, 3H) 2.04-2.21 (m, 1H) 1.34-1.96 (m, 10H).

(2nd eluted) (Intermediate 13) (diastereoisomer 2) Methyl (2S,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (27 mg, 0.045 mmol, 31% yield) as a colourless oil.

1H NMR (400 MHz, DMSO-d₆) δ ppm 7.97-8.03 (m, 1H) 7.66-7.73 (m, 2H) 7.12-7.20 (m, 1H) 6.88-6.94 (m, 1H) 6.74-6.83 (m, 1H) 5.26-5.36 (m, 1H) 4.09-4.17 (m, 1H) 3.71-3.79 (m, 1H) 3.51-3.65 (m, 3H) 2.63-3.41 (m, 5H) 2.27-2.35 (m, 3H) 2.04-2.18 (m, 1H) 1.81-1.95 (m, 1H) 1.38-1.79 (m, 9H)

Intermediate 12 (Method B)

Methyl (2R,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (12)

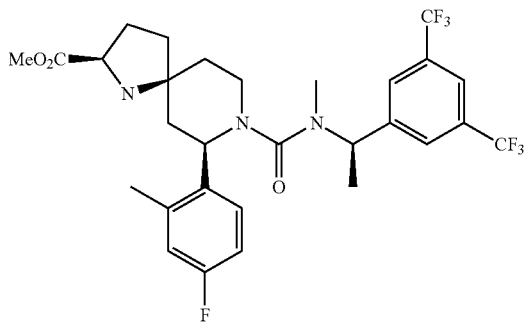 [SMILES: COC(=O)[C@H]1CC[C@@]2(CCN(C(=O)N(C)[C@H](C)c3cc(C(F)(F)F)cc(C(F)(F)F)c3)[C@@H](c3ccc(F)cc3C)C2)N1]

To a solution of methyl (2R,7R)-8-{[{(1R)-1-[3,5-bis(trifluoromethyl)phenyl]ethyl}(methyl)amino]carbonyl}-7-(4-fluoro-2-methylphenyl)-4-iodo-1,8-diazaspiro[4.5]decane-2-carboxylate (860 mg, 1.179 mmol) in methanol (20 ml), triethylamine (0.822 ml, 5.89 mmol) was added followed by palladium on carbon 10% (172 mg, 0.162 mmol). Resulting mixture was hydrogenated at atmospheric pressure of H2 at room temperature overnight.

Reaction mixture was filtered over sterimat, washed with MeOH and evaporated to dryness. Residue was treated with aqueous sat. NaHCO₃ (20 ml) and DCM (50 ml). Phases were separated and the aqueous one back-extracted with DCM (2×50 ml). Organics were combined, dried over Mg₂SO₄ and evaporated to dryness to give crude material (970 mg) as orange oil. This crude material was purified by SiO₂ flash chromatography eluting with cyclohexane/AcOEt from 6/4 to 1/1 to give, after evaporation of the solvent, title compound as white foaming solid, (515 mg, 0.853 mmol, 72.4% yield).

UPLC: Rt=0.68 min, m/z=604 [M+H]⁺.

¹H NMR (400 MHz, acetone) δ ppm 7.93 (s, 1H), 7.79 (s, 2H), 7.24-7.34 (m, 1H), 6.71-6.91 (m, 2H), 5.43-5.57 (m, 1H), 4.29 (d, 1H), 3.74-3.86 (m, 1H), 3.66 (s, 3H), 3.37-3.49 (m, 1H), 2.84 (s, 3H), 2.80-2.91 (m, 1H), 2.41 (s, 3H), 1.54 (d, 3H), 1.48-2.36 (m, 8H)

Intermediate 14

1,1-dimethylethyl(2R)-2-(4-fluoro-2-methylphenyl)-4-oxo-1-piperidinecarboxylate

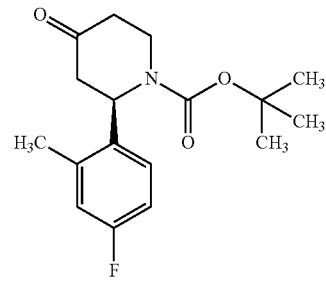 [SMILES: Cc1cc(F)ccc1[C@H]1CC(=O)CCN1C(=O)OC(C)(C)C]

To a solution of (2S)-hydroxy(phenyl)ethanoic acid—(2R)-2-(4-fluoro-2-methylphenyl)-4-piperidinone (1:1) (WO 2008090117 published on 31 Jul. 2008) (50 g, 139 mmol) in dry Dichloromethane (DCM) (550 ml) TEA (29.1 ml, 209 mmol) was added and then BOC-Anhydride (38.8 ml, 167 mmol). The reaction mixture was stirred overnight at r.t. The reaction was diluted with NaHCO3 sat. sol. (400 ml) and two phases were separated. The organic layer was dried (Na2SO4), filtered and evaporated in vacuo. The residue was purified by a small pad of silica panel eluting with Cy to 7:3 Cy/EtOAc to afford the title compound (37.6 g, 122 mmol, 88% yield). 1H NMR (400 MHz, CHLOROFORM-d) δ ppm 7.08-7.18 (m, 1H) 6.80-6.92 (m, 2H) 5.62 (br. s., 1H) 4.16-4.32 (m, 1H) 3.09-3.30 (m, 1H) 2.79 (d, 2H) 2.39-2.62 (m, 2H) 2.33 (s, 3H) 1.33-1.51 (m, 9H); UPLC: Rt=0.77 mins, m/z=251 [M−56+H]⁺.

Intermediate 15 and 16

1,1-dimethylethyl (2R,4R)-4-amino-2-(4-fluoro-2-methylphenyl)-4-(2-propen-1-yl)-1-piperidinecarboxylate (Intermediate 15) and 1,1-dimethylethyl (2R,4S)-4-amino-2-(4-fluoro-2-methylphenyl)-4-(2-propen-1-yl)-1-piperidinecarboxylate (Intermediate 16)

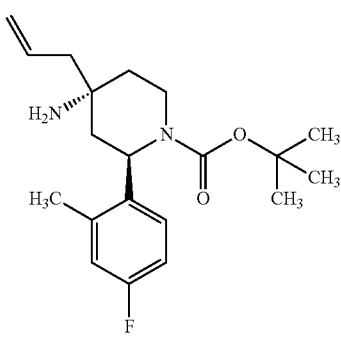

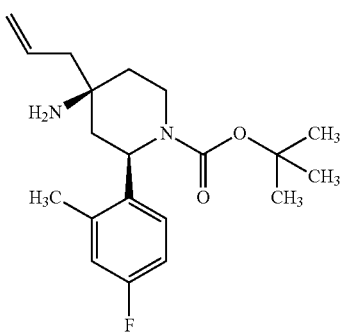

1,1-dimethylethyl (2R)-2-(4-fluoro-2-methylphenyl)-4-oxo-1-piperidinecarboxylate (Intermediate 14, 37.6 g, 122 mmol) was dissolved in 7M AMMONIA in MeOH (175 ml, 1223 mmol) and stirred at rt for 15 mins. 4,4,5,5-tetramethyl-2-(2-propen-1-yl)-1,3,2-dioxaborolane (26.7 g, 159 mmol) was added and reaction was stirred at it overnight. The reaction mixture was evaporated in vacuo to obtain a yellow oil that was dissolved in 100 ml of EtOAc and washed with 2×50 ml of NaHCO3 sat. sol. and then with 50 ml of Brine. Organic layer was dried and evaporated in vacuo to afford 48 g of crude. 800 mg of this material were purified on Biotage NH-column (40M) eluting with 8:2 Cy/EtOAc to afford:

($1^{st}$ eluted) 1,1-dimethylethyl (2R,4R)-4-amino-2-(4-fluoro-2-methylphenyl)-4-(2-propen-1-yl)-1-piperidinecarboxylate (Intermediate 15, 402 mg, 1.154 mmol; 0.94% yield). 1H NMR (500 MHz, acetone) δ ppm 7.23 (dd, 1H) 6.86-6.95 (m, 2H) 5.84-5.97 (m, 1H) 5.11 (dd, 1H) 5.07 (dd, 1H) 5.02 (d, 1H) 3.96-4.07 (m, 1H) 3.38-3.48 (m, 1H) 2.37 (s, 3H) 2.11-2.23 (m, 2H) 1.77-1.85 (m, 1H) 1.67-1.77 (m, 1H) 1.60-1.67 (m, 1H) 1.49-1.58 (m, 1H) 1.36 (br. s., 2H) 1.18 (s, 9H). Dipolar correlations: H-12 to H-13, -14, -3, -3', -5, -5'; H-2 (3.41 ppm) to H-20, -2 (4.02 ppm), -12, -3 (1.75 ppm), -5 (1.70 ppm); H-20 to H-6 (weak), -2 (3.41 ppm), Me-24, -5, -5', Boc; Me-24 to H-6 (strong), -17, -5, -5', Boc. Dipolar correlations are meaningful only if the piperidine ring adopts a non-chair conformation, e.g. twistboat. In addition, the aromatic moiety is rotational hindered, i.e. Me-24 and H-20 give different dipolar correlations. The atom numbering shown in the following structure is included for the purpose of correlation with the NMR data only.

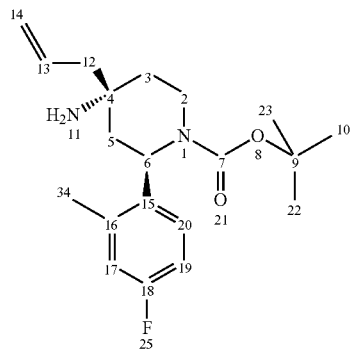

($2^{nd}$ eluted) 1,1-dimethylethyl (2R,4S)-4-amino-2-(4-fluoro-2-methylphenyl)-4-(2-propen-1-yl)-1-piperidinecarboxylate (Intermediate 16, 270 mg, 0.775 mmol, 0.63% yield). 1H NMR (500 MHz, acetone) δ ppm 7.29 (dd, 1H) 6.86-6.94 (m, 2H) 5.94-6.06 (m, 1H) 5.11-5.18 (m, 2H) 4.99 (dd, 1H) 4.02-4.12 (m, 1H) 3.53-3.65 (m, 1H) 2.36 (s, 3H) 2.19-2.29 (m, 2H) 1.86 (dd, 1H) 1.64-1.78 (m, 2H) 1.54-1.64 (m, 1H) 1.21 (s, 9H); Dipolar correlations: H-12 to H-3, -3', -5, -5', -13, -14; H-6 to Me-24, H-12 (strong), -5, -5'; H-20 to H-2 (3.58 ppm, strong), -6 (weak), -5, Boc. Dipolar correlations are meaningful only if the piperidine ring adopts a non-chair conformation, e.g. twistboat. In addition, the aromatic moiety is rotational hindered (see other isomer Isomer 2). The atom numbering shown in the following structure is included for the purpose of correlation with the NMR data only.

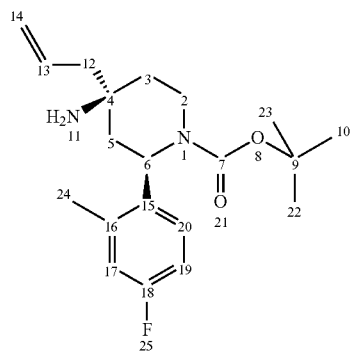

The residual crude was purified on biotage Si-column (75 L) eluting with 98:2 DCM/MeOH to obtain:

($1^{st}$ eluted) 1,1-dimethylethyl (2R,4R)-4-amino-2-(4-fluoro-2-methylphenyl)-4-(2-propen-1-yl)-1-piperidinecarboxylate (Intermediate 15, 24 g, 68.9 mmol; 56.3% yield). UPLC: Rt=0.57 mins, m/z=349 [M+H]$^+$; 293 [M−56+H]$^+$.

($2^{nd}$ eluted) 1,1-dimethylethyl (2R,4S)-4-amino-2-(4-fluoro-2-methylphenyl)-4-(2-propen-1-yl)-1-piperidinecarboxylate (Intermediate 3, 18 g, 51.7 mmol, 42.2% yield). UPLC: Rt=0.58 mins, m/z=349 [M+H]$^+$; 293 [M−56+H]$^+$.

Intermediate 17

1,1-dimethylethyl (2R,4S)-2-(4-fluoro-2-methylphenyl)-4-({[(phenylmethyl)oxy]carbonyl}amino)-4-(2-propen-1-yl)-1-piperidinecarboxylate

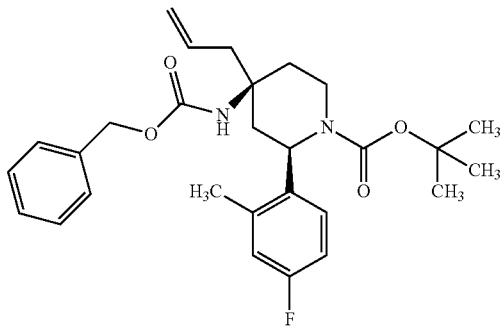 [SMILES: C=CC[C@]1(NC(=O)OCc2ccccc2)CCN(C(=O)OC(C)(C)C)[C@@H](c2ccc(F)cc2C)C1]

To a solution of 1,1-dimethylethyl (2R,4S)-4-amino-2-(4-fluoro-2-methylphenyl)-4-(2-propen-1-yl)-1-piperidinecarboxylate (Intermediate 16, 25 g, 71.7 mmol) in dry DCM (400 ml), at 0° C., a solution of Dibenzyl dicarbonate (25 g, 87 mmol) in DCM (100 ml) was added and the reaction mixture was stirred for 2 hours at the same temperature. The solvent was evaporated and the residue was purified by flash chromatography (Biotage system) on silica gel using a column 65+M and from cyclohexane to 8:2 cyclohexane/ethyl acetate as eluent affording the title compound (29 g, 60.1 mmol, 84% yield) as a white foam. 1H NMR (400 MHz, DMSO-d6) δ ppm 7.18-7.40 (m, 5H) 7.05-7.13 (m, 1H) 6.93-7.01 (m, 2H) 6.85-6.93 (m, 1H) 5.66-5.81 (m, 1H) 4.99-5.19 (m, 2H) 4.89-4.98 (m, 1H) 4.74-4.84 (m, 1H) 4.46-4.65 (m, 1H) 3.87-3.98 (m, 1H) 3.44-3.59 (m, 1H) 2.20-2.57 (m, 6H) 1.86-1.97 (m, 1H) 1.71-1.83 (m, 1H) 1.51-1.66 (m, 1H) 1.16 (s, 9H); UPLC: Rt=0.97 mins, m/z=483 [M+H]$^+$; 427 [M−56+H]$^+$.

Intermediate 18 phenylmethyl [(2R,4S)-2-(4-fluoro-2-methylphenyl)-4-(2-propen-1-yl)-4-piperidinyl]carbamate

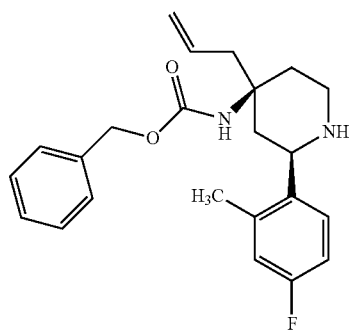 [SMILES: C=CC[C@]1(NC(=O)OCc2ccccc2)CCN[C@@H](c2ccc(F)cc2C)C1]

To a solution of 1,1-dimethylethyl (2R,4S)-2-(4-fluoro-2-methylphenyl)-4-({[(phenylmethyl)oxy]carbonyl}amino)-4-(2-propen-1-yl)-1-piperidinecarboxylate (Intermediate 17 29 g, 60.1 mmol) in dry Dichloromethane (DCM) (500 ml), at 0° C., TFA (125 ml, 1622 mmol) was slowly added in 30 mins and the reaction mixture was stirred for 2 hours at the same temperature. The reaction was diluted with DCM (300 ml) and a saturated solution of NaHCO3 was added until pH=8. Two phases were separated and the aqueous layer was extracted with DCM (200 ml). Combined organic layers were dried (Na2SO4), filtered and evaporated affording the title compound (23.0 g, 60.1 mmol, quantitative yield) as a colourless oil. 1H NMR (400 MHz, DMSO-d6) δ ppm 7.46-7.56 (m, 1H) 7.25-7.41 (m, 5H) 7.07 (br. s., 1H) 6.92-7.03 (m, 2H) 5.67-5.83 (m, 1H) 5.03-5.19 (m, 2H) 4.97 (s, 2H) 3.96 (d, 1H) 2.82-3.03 (m, 2H) 2.76 (d, 2H) 2.29 (s, 3H) 1.99 (d, 2H) 1.54-1.68 (m, 1H) 1.36 (t, 1H); UPLC: Rt=0.62 mins, m/z=383 [M+H]$^+$.

Intermediate 19 phenylmethyl [(2R,4S)-1-{[{[3,5-bis(trifluoromethyl)phenyl]methyl}(methyl)amino]carbonyl}-2-(4-fluoro-2-methylphenyl)-4-(2-propen-1-yl)-4-piperidinyl]carbamate

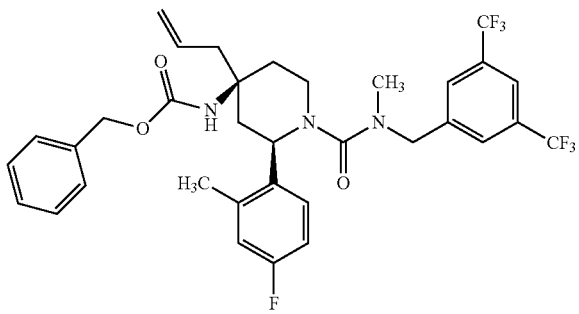 [SMILES: C=CC[C@]1(NC(=O)OCc2ccccc2)CCN(C(=O)N(C)Cc2cc(C(F)(F)F)cc(C(F)(F)F)c2)[C@@H](c2ccc(F)cc2C)C1]

To a solution of triphosgene (0.714 g, 2.405 mmol) at 0° C. in dry ethyl acetate (5.5 ml) was slowly added a solution of phenylmethyl [(2R,4S)-2-(4-fluoro-2-methylphenyl)-4-(2-propen-1-yl)-4-piperidinyl]carbamate (Intermediate 18, 2 g, 5.23 mmol) and TEA (1.8 ml) in dry ethyl Acetate (10 ml) and the mixture was stirred for 5 minutes at the same temperature. Then a solution of {[3,5-bis(trifluoromethyl)phenyl]methyl}methylamine (WO 2007107818, 27 Sep. 2007) (1.479 g, 5.75 mmol) and TEA (1.63 ml) in dry Ethyl acetate (10 ml) was added in 5 minutes at 0° C. The resulting suspension was refluxed for 5 hours. After cooling, NaHCO3 sat. aq. solution and ethyl acetate were added to the reaction mixture and two phases were separated. The aqueous phase was extracted with ethyl acetate (3×) and the combined organic phases were dried (Na2SO4), filtered and evaporated to dryness. The residue was purified by flash chromatography with Biotage SP1 (from 1:0 to 7:3 Cyclohexane/EtOAc; 40 M) to give two batches of the title compound: 1$^{st}$ batch (1.6 g, 2.40 mmol, 46.0% yield); 1H NMR (500 MHz, DMSO-d6) δ ppm 7.94 (s, 1H) 7.61 (s, 2H) 7.27-7.38 (m, 5H) 7.24 (dd, 1H) 7.18 (br. s., 1H) 6.91 (dd, 1H) 6.76-6.83 (m, 1H) 5.68-5.81 (m, 1H) 5.06-5.18 (m, 2H) 4.88-5.00 (m, 2H) 4.60 (d, 1H) 4.36-4.44 (m, 1H) 4.36 (d, 1H) 3.36-3.47 (m, 1H) 2.94-3.06 (m, 1H) 2.88 (s, 3H) 2.63-2.72 (m, 2H) 2.31 (s, 3H) 1.84-2.05 (m, 3H) 1.64 (t, 1H); UPLC: Rt=1.02 mins; m/z=666 [MH]+. The 2$^{nd}$ batch was purified again by flash chromatography via Biotage SP1 (from 1:0 to 7:3 Cyclohexane/EtOAc; 40 M) to give further two batches of the title compound (0.8 g and 0.15 g).

Intermediate 20 phenylmethyl [(2R,4S)-1-{[{[3,5-bis(trifluoromethyl)phenyl]methyl}(methyl)amino]carbonyl}-2-(4-fluoro-2-methylphenyl)-4-(2-oxoethyl)-4-piperidinyl]carbamate

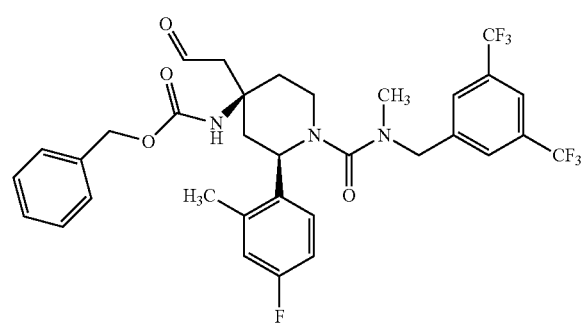 [SMILES: Cc1cc(F)ccc1[C@H]1C[C@@](CC=O)(NC(=O)OCc2ccccc2)CCN1C(=O)N(C)Cc1cc(C(F)(F)F)cc(C(F)(F)F)c1]

A solution of phenylmethyl [(2R,4S)-1-{[{[3,5-bis(trifluoromethyl)phenyl]methyl}(methyl)amino]carbonyl}-2-(4-fluoro-2-methylphenyl)-4-(2-propen-1-yl)-4-piperidinyl] carbamate (Intermediate 19, 600 mg, 0.901 mmol) in Dichloromethane (DCM) (50 ml) was cooled to −78° C. and ozone was bubbled through the stirred reaction mixture for 10 mins; the reaction became blue. Then it was stirred under a nitrogen atmosphere and dimethyl sulfide (11.73 ml, 159 mmol) was added at −78° C. The resulting mixture was stirred for 16 hrs to quench residual ozonide. This reaction mixture was combined to an analogous reaction mixture prepared using similar procedure a solution of phenylmethyl [(2R,4S)-1-{[{[3,5-bis(trifluoromethyl)phenyl]methyl}(methyl)amino]carbonyl}-2-(4-fluoro-2-methylphenyl)-4-(2-propen-1-yl)-4-piperidinyl]carbamate (Intermediate 19, 500 mg, 0.751 mmol) in Dichloromethane (DCM) (50 ml) was cooled to −78° C. and ozone was bubbled through the stirred reaction mixture for 10 mins. The solution became blue. The reaction was stirred under a nitrogen atmosphere and dimethyl sulfide (10 ml, 135 mmol) was added at −78° C. The resulting mixture was stirred for 24 hrs to quench residual ozonide.

The two combined reaction mixture were evaporated to dryness and the crude was purified by flash-chromatography with SP1 (from 1:0, plateaux at 8:2, plateaux at 7:3, plateaux at 1:1 to 0:1 Cyclohexane/EtOAc) to give the title compound (868 mg, 1.3 mmol, 79% yield considering the total amount of starting material used in the two reactions) as a white foam. 1H NMR (400 MHz, DMSO-$d_6$) δ ppm 9.72 (t, 1H) 7.85-8.00 (m, 1H) 7.62 (s, 2H) 7.45-7.61 (m, 1H) 7.18-7.44 (m, 6H) 6.92 (dd, 2.69 Hz, 1H) 6.80 (td, 2.63 Hz, 1H) 4.88-5.04 (m, 2H) 4.62 (d, 1H) 4.30-4.46 (m, 2H) 3.34-3.54 (m, 1H) 2.90-3.10 (m, 3H) 2.90 (s, 3H) 2.32 (s, 3H) 2.03-2.25 (m, 2H) 1.90-2.04 (m, 1H) 1.73 (t, 1H); HPLC: Rt=7.78 mins; MS: m/z=668 [MH]+ and 690 [M+Na]+.

Intermediate 21 methyl (2E,Z)-4-[(2R,4S)-1-{[{[3,5-bis(trifluoromethyl)phenyl]methyl}(methyl)amino]carbonyl}-2-(4-fluoro-2-methylphenyl)-4-({[(phenylmethyl)oxy]carbonyl}amino)-4-piperidinyl]-2-{[(1,1-dimethylethyl)(dimethyl)silyl]oxy}-2-butenoate

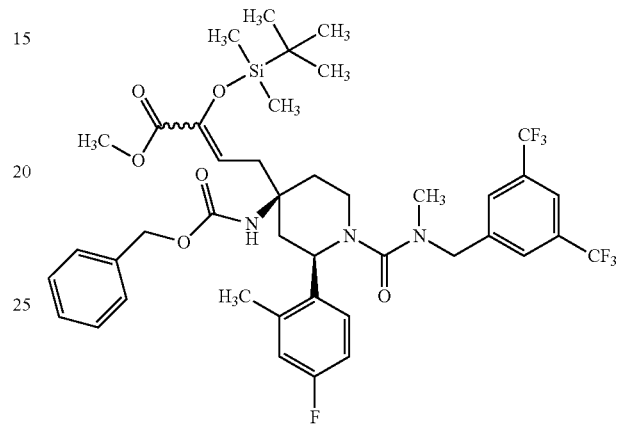

DBU (0.359 ml, 2.400 mmol) was added dropwise to a suspension of LiCl (110 mg, 2.59 mmol) and methyl [bis(methyloxy)phosphoryl]{[(1,1-dimethylethyl)(dimethyl)silyl]oxy}acetate (Tetrahedron Lett. 1981, 22, 663-666; J. Org. Chem. 2006, 71, 9144-9152, 810 mg, 2.59 mmol) in dry Acetonitrile (15 ml) and the mixture was maintained at 0° C. for 1 hr. A solution of phenylmethyl [(2R,4S)-1-{[{[3,5-bis(trifluoromethyl)phenyl]methyl}(methyl)amino]carbonyl}-2-(4-fluoro-2-methylphenyl)-4-(2-oxoethyl)-4-piperidinyl]carbamate (Intermediate 20, 866 mg, 1.297 mmol) in Acetonitrile (5 mL) was added dropwise at 0° C. and the reaction mixture was stirred for 1 hr, while the temperature was allowed to increase to 25° C. Further solution of LiCl (220 mg, 5.18 mmol), methyl [bis(methyloxy)phosphoryl]{[(1,1-dimethylethyl)(dimethyl)silyl]oxy}acetate (Tetrahedron Lett. 1981, 22, 663-666; J. Org. Chem. 2006, 71, 9144-9152, 1.6 g, 5.18 mmol) and DBU (0.718 ml, 4.8 mmol) in dry Acetonitrile (10 ml), maintained at 0° C. for 10 mins, was added at 25° C. to the reaction mixture and it was stirred overnight. Further solution of LiCl (110 mg, 2.59 mmol), methyl [bis(methyloxy)phosphoryl]{[(1,1-dimethylethyl)(dimethyl)silyl]oxy}acetate (Tetrahedron Lett. 1981, 22, 663-666; J. Org. Chem. 2006, 71, 9144-9152, 810 mg, 2.59 mmol) and DBU (0.359 ml, 2.40 mmol) in dry Acetonitrile (5 ml), maintained at 0° C. for 10 mins, was added to the reaction mixture cooled to 0° C. and it was stirred for 2 hours while the temperature was allowed to increase to 25° C. NaHCO3 saturated aqueous solution and EtOAc were added and the two phases were separated. The aqueous phase was extracted with EtOAc (2×) and the combined organic phases were dried and evaporated to dryness. The crude was purified by flash-chromatography (SP1; from 1:0 to 7:3 Cyclohexane/EtOAc) to give the title compound (889 mg, 1.041 mmol, 80% yield) as a white solid. 1H NMR (400 MHz, DMSO-$d_6$) δ ppm 6.54-8.14 (m, 12H) 5.38-6.07 (m, 1H) 3.72 (s, 3H) 2.71-5.11 (m, 7H) 2.51 (s, 3H) 2.28 (s, 3H) 0.99-2.13 (m, 6H) 0.91 (s, 9H)

0.09 (s, 6H). The sample consists of two species ratio ~3:1 most probably E and Z isomers (E/Z not assigned). UPLC: Rt=1.19 mins; m/z=854[M+H]+.

Intermediate 22 and 23 methyl (2R,5S,7R)-8-{[{[3,5-bis(trifluoromethyl)phenyl]methyl}(methyl)amino]carbonyl}-7-(4-fluoro-2-methylphenyl)-1,8-diazaspiro[4.5]decane-2-carboxylate (Intermediate 22) and methyl (2S,5S,7R)-8-{[{[3,5-bis(trifluoromethyl)phenyl]methyl}(methyl)amino]carbonyl}-7-(4-fluoro-2-methylphenyl)-1,8-diazaspiro[4.5]decane-2-carboxylate (Intermediate 23)

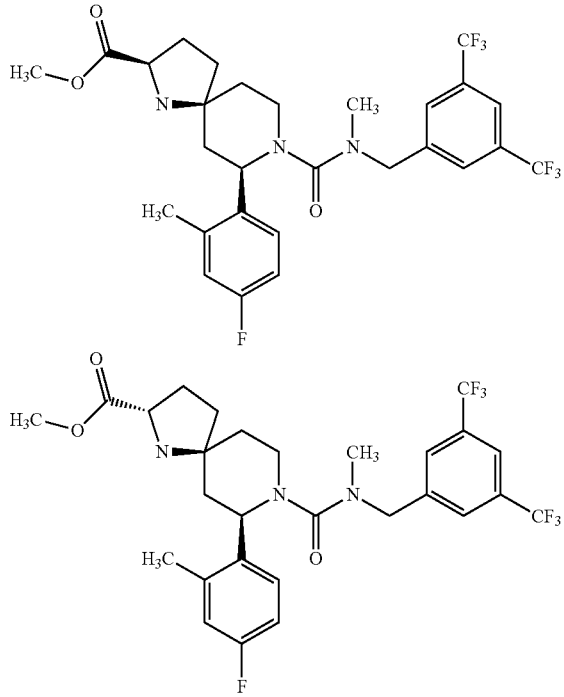

To a solution of Methyl (2E,Z)-4-[(2R,4S)-1-{[{[3,5-bis(trifluoromethyl)phenyl]methyl}(methyl)amino]carbonyl}-2-(4-fluoro-2-methylphenyl)-4-({[(phenylmethyl)oxy]carbonyl}amino)-4-piperidinyl]-2-{[(1,1-dimethylethyl)(dimethyl)silyl]oxy}-2-butenoate (Intermediate 21, 885 mg, 1.036 mmol) in Methanol (16 ml) was added cesium fluoride (504 mg, 3.32 mmol) and the resulting solution was left still for 1 hr. Then 10% palladium on Carbon (90 mg, 0.846 mmol) was added to the solution and the resulting mixture was stirred under Hydrogen atmosphere (P=1 atm) for 1 hr. The catalyst was filtered-off and the resulting solution was evaporated to dryness. The residue was partioned between EtOAc and water (to remove salts) and the two phases were separated. The aq. phase was extracted with EtOAc (2×) and the combined organic phases were dried and evaporated to dryness. The crude was purified by SP1 (from 1:0, plateaux at 1:9, plateaux at 0:1 Cyclohexane/EtOAc) to give:

(1st eluted) methyl (2R,5S,7R)-8-{[{[3,5-bis(trifluoromethyl)phenyl]methyl}(methyl)amino]carbonyl}-7-(4-fluoro-2-methylphenyl)-1,8-diazaspiro[4.5]decane-2-carboxylate (Intermediate 22, 69 mg, 0.117 mmol, 11.29% yield) as a white solid. 1H NMR (400 MHz, acetone) δ ppm 7.89 (s, 1H) 7.68 (s, 2H) 7.29-7.38 (m, 1H) 6.74-6.90 (m, 2H) 4.75 (d, 1H) 4.49 (d, 1H) 4.29 (dd, 1H) 3.79 (dd, 1H) 3.67 (s, 3H) 3.44-3.55 (m, 1H) 3.05 (s, 3H) 2.77-2.97 (m, 1H) 2.41 (s, 3H) 2.14-2.33 (m, 1H) 1.86-2.02 (m, 3H) 1.63-1.83 (m, 3H) 1.47-1.62 (m, 1H); the relative stereochemistry of the C(8) has been determined by dipolar correlation between CH(8) and CH2(7)eq at 1.71 ppm. The atom numbering shown in the following structure is included for the purpose of correlation with the NMR data only.

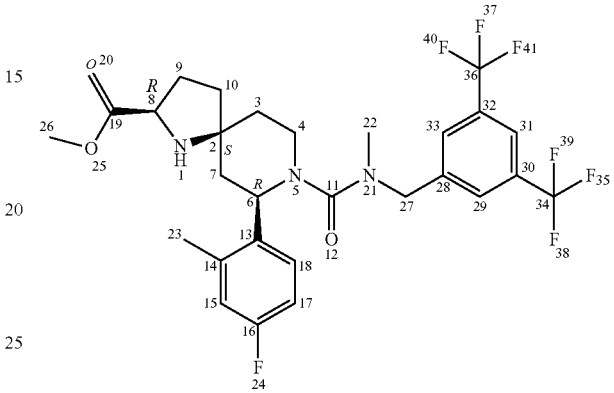

HPLC: Rt=6.56 mins; MS: m/z=590 [M+H]+.

(2nd eluted) methyl (2S,5S,7R)-8-{[{[3,5-bis(trifluoromethyl)phenyl]methyl}(methyl)amino]carbonyl}-7-(4-fluoro-2-methylphenyl)-1,8-diazaspiro[4.5]decane-2-carboxylate (Intermediate 23, 385 mg, 0.653 mmol, 63.0% yield) as a white solid. 1H NMR (400 MHz, acetone) δ ppm 7.89 (s, 1H) 7.68 (s, 2H) 7.28-7.41 (m, 1H) 6.73-6.90 (m, 2H) 4.75 (d, 1H) 4.49 (d, 1H) 4.31 (dd, 1H) 3.81 (dd, 1H) 3.63 (s, 3H) 3.40-3.54 (m, 1H) 3.05 (s, 3H) 2.77-2.95 (m, 1H) 2.41 (s, 3H) 2.12-2.33 (m, 1H) 1.79-2.11 (m, 4H) 1.59-1.79 (m, 3H); Due to overlap diagnostic signals (CH2(7) and CH2(3)eq) the relative stereochemistry of C(8) has been assigned after determination of the relative stereochemistry of the other diastereoisomer (Intermediate 22). The atom numbering shown in the following structure is included for the purpose of correlation with the NMR data only.

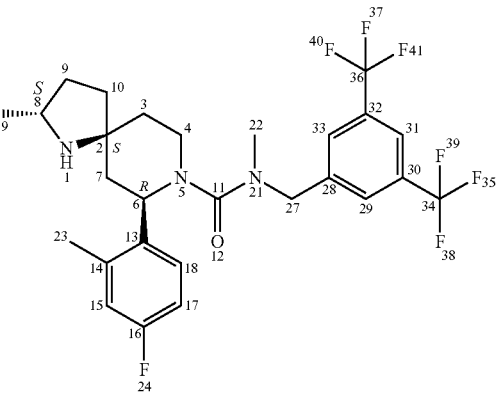

HPLC: Rt=6.63 mins; MS: m/z=590 [M+H]+.

Intermediate 24 (Method A)

phenylmethyl [(2R,4S)-1-{[{(1R)-1-[3,5-bis(trifluoromethyl)phenyl]ethyl}(methyl)amino]carbonyl}-2-(4-fluoro-2-methylphenyl)-4-(2-propen-1-yl)-4-piperidinyl]carbamate

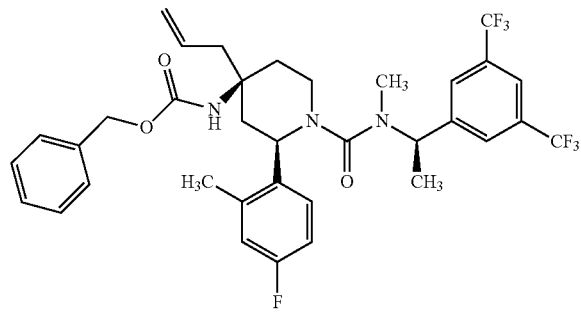 [SMILES: C=CC[C@]1(NC(=O)OCc2ccccc2)CCN(C(=O)N(C)[C@H](C)c2cc(C(F)(F)F)cc(C(F)(F)F)c2)[C@@H](c2ccc(F)cc2C)C1]

To a solution of triphosgene (0.35 g, 1.179 mmol) at 0° C. in dry ethyl Acetate (2.5 ml) was slowly added a solution of phenylmethyl [(2R,4S)-2-(4-fluoro-2-methylphenyl)-4-(2-propen-1-yl)-4-piperidinyl]carbamate (Intermediate 18, 0.98 g, 2.56 mmol) and TEA (0.9 ml) in dry Ethyl Acetate (5 ml) and the mixture was stirred for 5 minutes at the same temperature. Then a solution of {(1R)-1-[3,5-bis(trifluoromethyl)phenyl]ethyl}methylamine (Organic Letters, 5(7), 1007-1010; 2003, 0.764 g, 2.82 mmol) and TEA (0.78 ml) in dry Ethyl acetate (5 ml) was added in 5 minutes at 0° C. The resulting suspension was refluxed for 5 hours.

After cooling the mixture was diluted with ethyl acetate (100 ml) and washed with NaHCO3 sat. sol. (2×50 ml). The organic layer was dried (Na2SO4), filtered and evaporated and the residue was purified by flash chromatography (Biotage system) on silica gel using a column 25+M and from cyclohexane to 7:3 cyclohexane/ethyl acetate as eluent affording the title compound (1.1 g, 1.618 mmol, 63.2% yield) as a white foam. 1H NMR (400 MHz, DMSO-$d_6$) δ ppm 7.98 (s, 1H) 7.69 (s, 2H) 7.24-7.40 (m, 5H) 7.12-7.25 (m, 2H) 6.85-6.96 (m, 1H) 6.71-6.82 (m, 1H) 5.66-5.83 (m, 1H) 5.18-5.30 (m, 1H) 5.04-5.18 (m, 2H) 4.84-5.00 (m, 2H) 4.38-4.51 (m, 1H) 3.34-3.45 (m, 1H) 3.00-3.14 (m, 1H) 2.59-2.74 (m, 5H) 2.30 (s, 3H) 1.83-2.01 (m, 3H) 1.57-1.78 (m, 1H) 1.49 (d, 3H); UPLC: Rt=1.05 mins; m/z=680 [M+H]+.

Intermediate 24 (Method B) and 25 phenylmethyl [(2R,4S)-1-{[{(1R)-1-[3,5-bis(trifluoromethyl)phenyl]ethyl}(methyl)amino]carbonyl}-2-(4-fluoro-2-methylphenyl)-4-(2-propen-1-yl)-4-piperidinyl]carbamate (Intermediate 24, Method B) and phenylmethyl [(2R,4S)-1-{[{(1S)-1-[3,5-bis(trifluoromethyl)phenyl]ethyl}(methyl)amino]carbonyl}-2-(4-fluoro-2-methylphenyl)-4-(2-propen-1-yl)-4-piperidinyl]carbamate (Intermediate 25)

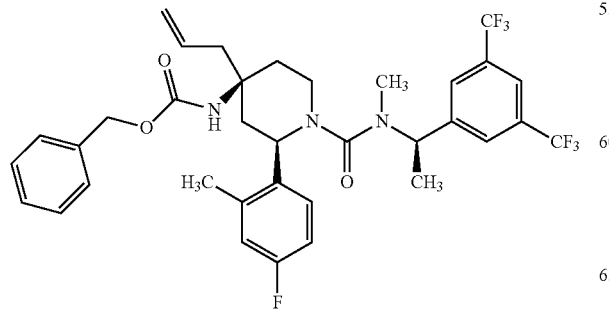

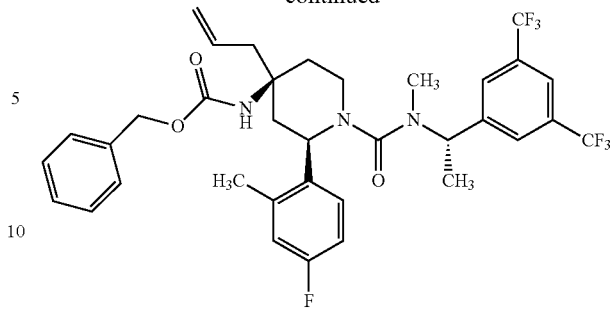

To a solution of triphosgene (1.713 g, 5.77 mmol) in dry Ethyl acetate (20 ml) at 0° C. was slowly added (formation of gas observed) a solution of phenylmethyl [(2R,4S)-2-(4-fluoro-2-methylphenyl)-4-(2-propen-1-yl)-4-piperidinyl]carbamate (Intermediate 18, 4.8 g, 12.55 mmol) and TEA (4.32 ml) in dry Ethyl acetate (20 ml) and the resulting mixture was stirred for 5 mins at 0° C. Then a solution of {1-[3,5-bis(trifluoromethyl)phenyl]ethyl}methylamine (3.74 g, 13.80 mmol) and TEA (3.9 ml) in dry Ethyl acetate (20 ml) was added at 0° C. and the reaction mixture was stirred for 5 mins at this temperature, then it was refluxed for 6 hrs. The reaction mixture was diluted with EtOAc and NaHCO3 sat. solution was added. The two phases were separated and the aq. phase was extracted with EtOAc (2×). The combined organic phases were dried (Na2SO4) and evaporated to dryness. The crude was purified by flash-chromatography (SP1; from 1:0, plateaux at 9:1, plateaux at 8:2, to 0:1 Cyclohexane/EtOAc) to give:

(1$^{st}$ eluted) phenylmethyl [(2R,4S)-1-{[{(1R)-1-[3,5-bis(trifluoromethyl)phenyl]ethyl}(methyl)amino]carbonyl}-2-(4-fluoro-2-methylphenyl)-4-(2-propen-1-yl)-4-piperidinyl]carbamate (Intermediate 24, Method B, 3.2 g, 4.71 mmol, 37.5% yield) as a white solid. 1H NMR (400 MHz, DMSO-$d_6$) δ ppm 7.98 (s, 1H) 7.69 (s, 2H) 7.13-7.41 (m, 7H) 6.85-6.97 (m, 1H) 6.67-6.83 (m, 1H) 5.65-5.81 (m, 1H) 5.24 (q, 1H) 5.05-5.17 (m, 2H) 4.85-5.01 (m, 2H) 4.33-4.54 (m, 1H) 3.36-3.49 (m, 1H) 2.95-3.17 (m, 1H) 2.66 (s, 3H) 2.53-2.77 (m, 2H) 2.30 (s, 3H) 1.76-2.02 (m, 3H) 1.72 (t, 1H) 1.49 (d, 3H); determination of stereochemistry of C(33) was determined by NMR comparison with Intermediate 24 prepared following Method A: the two spectra were concordant. The atom numbering shown in the following structure is included for the purpose of correlation with the NMR data only.

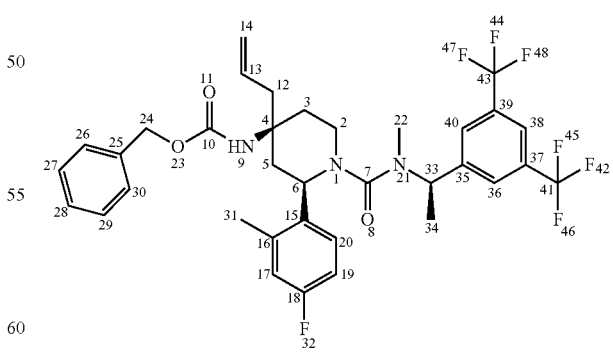

UPLC: Rt=1.04 mins, m/z=680 [M+H]+.

(2$^{nd}$ eluted) phenylmethyl [(2R,4S)-1-{[{(1S)-1-[3,5-bis(trifluoromethyl)phenyl]ethyl}methyl)amino]carbonyl}-2-(4-fluoro-2-methylphenyl)-4-(2-propen-1-yl)-4-piperidinyl]carbamate (Intermediate 25, 3.39 g, 4.99 mmol, 39.7% yield)

as a white solid. 1H NMR (500 MHz, DMSO-d6) δ ppm 7.92 (s, 1H) 7.57 (s, 2H) 7.06-7.44 (m, 7H) 6.89 (dd, 1H) 6.74-6.81 (m, 1H) 5.67-5.83 (m, 1H) 5.31 (d, 1H) 5.06-5.18 (m, 2H) 4.88-5.03 (m, 2H) 4.38 (d, 1H) 3.33-3.44 (m, 1H) 2.90-3.03 (m, 1H) 2.79 (s, 3H) 2.58-2.77 (m, 2H) 2.30 (s, 3H) 1.55-2.09 (m, 4H) 1.49 (d, 3H); determination of stereochemistry of C(33) was determined by NMR comparison with the epimer Intermediate 24 prepared following Method B. The atom numbering shown in the following structure is included for the purpose of correlation with the NMR data only.

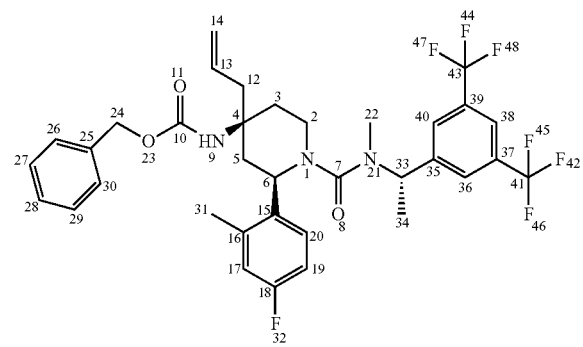 [SMILES: C=CC[C@]1(NC(=O)OCc2ccccc2)CCN(C(=O)N(C)[C@@H](C)c2cc(C(F)(F)F)cc(C(F)(F)F)c2)[C@@H](c2ccc(F)cc2C)C1]

UPLC: Rt=1.04-1.05 mins, m/z=680 [M+H]+.

Evaporation of mixed fractions gave 591 mg of a crude that was not further purified.

Intermediate 26 phenylmethyl [(2R,4S)-1-{[{(1S)-1-[3,5-bis(trifluoromethyl)phenyl]ethyl}(methyl) amino]carbonyl}-2-(4-fluoro-2-methylphenyl)-4-(2-oxoethyl)-4-piperidinyl]carbamate

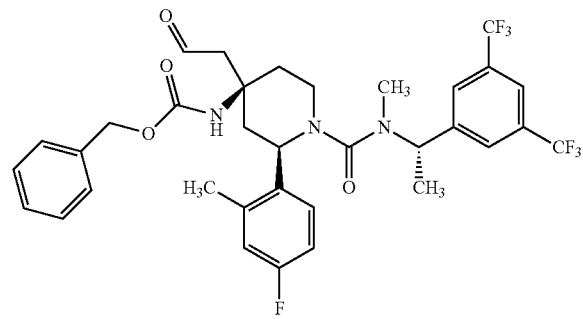 [SMILES: Cc1cc(F)ccc1[C@H]1C[C@@](CC=O)(NC(=O)OCc2ccccc2)CCN1C(=O)N(C)[C@@H](C)c1cc(C(F)(F)F)cc(C(F)(F)F)c1]

A solution of phenylmethyl [(2R,4S)-1-{[{(1S)-1-[3,5-bis(trifluoromethyl)phenyl]ethyl}(methyl)amino]carbonyl}-2-(4-fluoro-2-methylphenyl)-4-(2-propen-1-yl)-4-piperidinyl]carbamate (Intermediate 25, 1.21 g, 1.780 mmol) in Dichloromethane (DCM) (80 ml) was cooled to −78° C. and ozone was bubbled through the stirred reaction mixture for 10 mins; the reaction became blue. The reaction was stirred under a nitrogen atmosphere and dimethyl sulfide (10 ml, 1.78 mmol) was added at −78° C. The resulting mixture was stirred for 2 days to quench residual ozonide. The solvent was evaporated to dryness and the crude was purified by flash-chromatography (SP1; from 1:0, plateaux at 6:4, to 0:1 Cyclohexane/EtOAc) to give the title compound (848 mg, 1.244 mmol) as a yellowish foam. 1H NMR (400 MHz, DMSO-d6) δ ppm 9.66-9.77 (m, 1H) 7.94 (s, 1H) 7.48-7.63 (m, 3H) 7.26-7.39 (m, 5H) 7.17-7.26 (m, 1H) 6.86-6.95 (m, 1H) 6.71-6.84 (m, 1H) 5.25-5.38 (m, 1H) 4.89-5.02 (m, 2H) 4.35-4.45 (m, 1H) 3.36-3.46 (m, 1H) 2.91-3.09 (m, 3H) 2.80 (s, 3H) 2.31 (s, 3H) 2.03-2.24 (m, 2H) 1.87-2.02 (m, 1H) 1.60-1.75 (m, 1H) 1.49 (d, 3H); HPLC: Rt=7.19 mins; MS: m/z=682 [M+H]+ and 704 [M+Na]+.

Intermediate 27 methyl (2Z,2E)-4-[(2R,4S)-1-{[{(1S)-1-[3,5-bis(trifluoromethyl)phenyl]ethyl}(methyl)amino]carbonyl}-2-(4-fluoro-2-methylphenyl)-4-({[(phenylmethyl)oxy]carbonyl}amino)-4-piperidinyl]-2-{[(1,1-dimethylethyl)(dimethyl)silyl]oxy}-2-butenoate

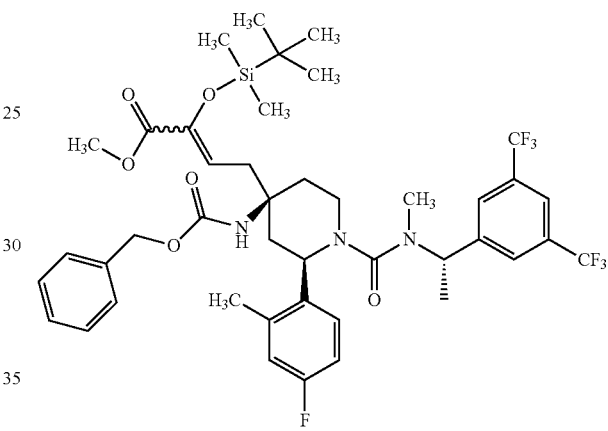

DBU (0.341 ml, 2.28 mmol) was added dropwise to a suspension of LiCl (104 mg, 2.465 mmol) and methyl [bis(methyloxy)phosphoryl]{[(1,1-dimethylethyl)(dimethyl)silyl]oxy}acetate (Tetrahedron Lett. 1981, 22, 663-666; J. Org. Chem. 2006, 71, 9144-9152, 770 mg, 2.465 mmol) in dry Acetonitrile (15 ml) and the mixture was maintained at 0° C. for 1 hr. A solution of phenylmethyl [(2R,4S)-1-{[{(1S)-1-[3,5-bis(trifluoromethyl)phenyl]ethyl}(methyl)amino]carbonyl}-2-(4-fluoro-2-methylphenyl)-4-(2-oxoethyl)-4-piperidinyl]carbamate (Intermediate 26, 840 mg, 1.232 mmol) in Acetonitrile (5 ml) was added dropwise at 0° C. and the reaction mixture was stirred for 1 hr, while the temperature was allowed to increase to 25° C. Further solution of methyl [bis(methyloxy)phosphoryl]{[(1,1-dimethylethyl)(dimethyl)silyl]oxy}acetate (Tetrahedron Lett. 1981, 22, 663-666; J. Org. Chem. 2006, 71, 9144-9152, 770 mg, 2.465 mmol), LiCl (104 mg, 2.465 mmol) and DBU (0.341 ml, 2.280 mmol) in dry Acetonitrile (5 ml), maintained at 0° C. for 10 mins, was added at 0° C. to the reaction mixture and it was stirred overnight, while the temperature was allowed to increase to 25° C. Saturated NaHCO3 aqueous solution and EtOAc were added and the two phases were separated. The aqueous phase was extracted with EtOAc (2×) and the combined organic phases were dried and evaporated to dryness. The crude was purified by flash-chromatography (SP1; from 1:0 to 8:2 and then plateaux at 8:2 Cyclohexane/EtOAc) to give the title compound (734 mg, 0.846 mmol, 68.6% yield) as a white solid. 1H NMR (400 MHz, DMSO-d6) δ ppm 7.93 (s, 1H) 7.56 (s, 2H) 7.16-7.46 (m, 7H) 6.91 (dd, 1H) 6.72-6.82

(m, 1H) 5.48 (t, 1H) 5.25-5.36 (m, 1H) 4.86-5.04 (m, 2H) 4.34 (d, 1H) 3.72 (s, 3H) 2.74-3.49 (m, 4H) 2.80 (s, 3H) 2.26 (s, 3H) 1.54-2.10 (m, 4H) 1.48 (d, 3H) 0.90 (s, 9H) 0.08 (s, 6H); UPLC: Rt=1.22 mins, m/z=868 [M+H]+.

Intermediate 28 and 29 methyl (2R,5S,7R)-8-{[{(1S)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 28) and methyl (2S,5S,7R)-8-{[{(1S)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 29)

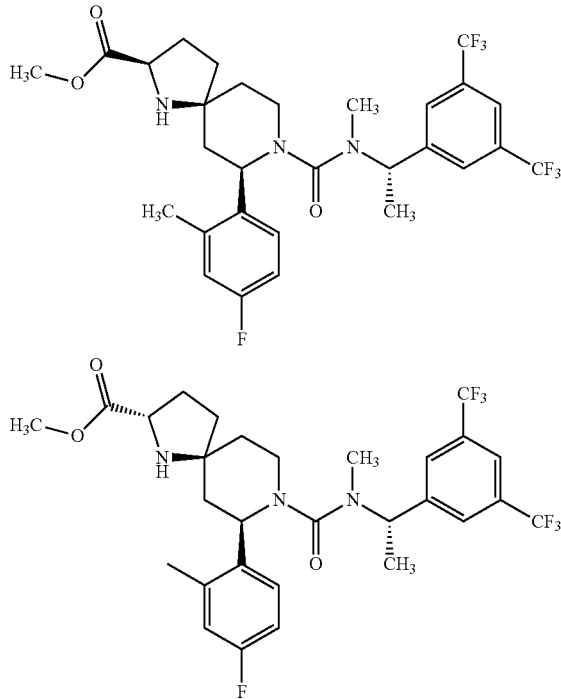

To a solution of methyl (2Z,2E)-4-[(2R,4S)-1-{[{(1S)-1-[3,5-bis(trifluoromethyl)phenyl]ethyl}(methyl)amino]carbonyl}-2-(4-fluoro-2-methylphenyl)-4-({[(phenylmethyl)oxy]carbonyl}amino)-4-piperidinyl]-2-{[(1,1-dimethylethyl)(dimethyl)silyl]oxy}-2-butenoate (Intermediate 27, 734 mg, 0.846 mmol) in Methanol (16 ml) was added cesium fluoride (411 mg, 2.71 mmol) and then palladium on carbon (10%) (73.4 mg, 0.690 mmol) and the resulting mixture was stirred under Hydrogen atmosphere (P=1 atm) for 1 hr. The catalyst was filtered-off and the resulting solution was evaporated to dryness. The residue was partioned between EtOAc and water (to remove salts) and the two phases were separated. The aq. phase was extracted with EtOAc (2×) and the combined organic phases were dried and evaporated to dryness. The crude was purified by SP1 (from 1:0, plateaux at 1:1 Cyclohexane/EtOAc to elute Intermediate 28, to 0:1 and plateaux at 0:1 Cyclohexane/EtOAc to elute Intermediate 29) to give:

(1st eluted) methyl (2R,5S,7R)-8-{[{(1S)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 28, 95 mg, 0.157 mmol, 18.61% yield) as a white gum. 1H NMR (400 MHz, acetone) δ ppm 7.87 (s, 1H) 7.66 (s, 2H) 7.23-7.34 (m, 1H) 6.70-6.89 (m, 2H) 5.56 (q, 1H) 4.26 (dd, 1H) 3.71-3.87 (m, 1H) 3.67 (s, 3H) 3.36-3.53 (m, 1H) 2.94 (s, 3H) 2.74-2.91 (m, 1H) 2.41 (s, 3H) 2.10-2.31 (m, 1H) 1.66-2.03 (m, 6H) 1.60 (d, 3H) 1.52 (t, 1H); The relative stereochemistry of the CH(8) was determined by dipolar correlations between CH(8) and CH2(7)eq (1.76 ppm) and CH2(7)ax (1.52 ppm). The atom numbering shown in the following structure is included for the purpose of correlation with the NMR data only.

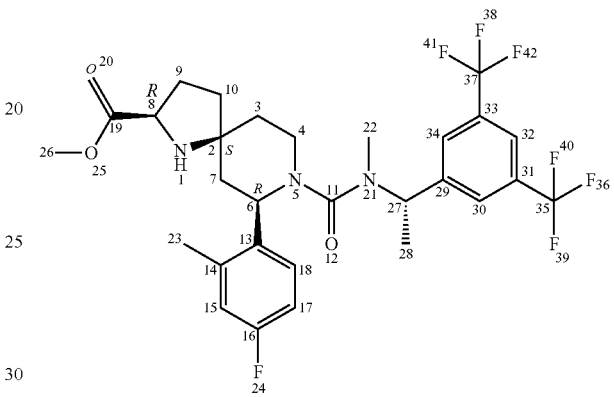

HPLC: Rt=5.2 mins; MS: m/z=604 [M+H]+ and 626 [M+Na]+.

(2nd eluted) methyl (2S,5S,7R)-8-{[{(1S)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 29, 324 mg, 0.537 mmol, 63.5% yield) as a white solid. 1H NMR (400 MHz, acetone) δ ppm 7.87 (s, 1H) 7.66 (s, 2H) 7.25-7.34 (m, 1H) 6.70-6.89 (m, 2H) 5.49-5.61 (m, 1H) 4.29 (d, 1H) 3.73-3.84 (m, 1H) 3.63 (s, 3H) 3.37-3.51 (m, 1H) 2.93 (s, 3H) 2.75-2.90 (m, 1H) 2.41 (s, 3H) 2.13-2.30 (m, 1H) 1.59 (d, 3H) 1.53-2.05 (m, 7H). Due to overlapping of the diagnostic signals (CH(7)eq and CH(3)eq) the relative stereochemistry of the CH(8) was assigned after confirmation of the other diastereoisomer (Intermediate 28). The atom numbering shown in the following structure is included for the purpose of correlation with the NMR data only.

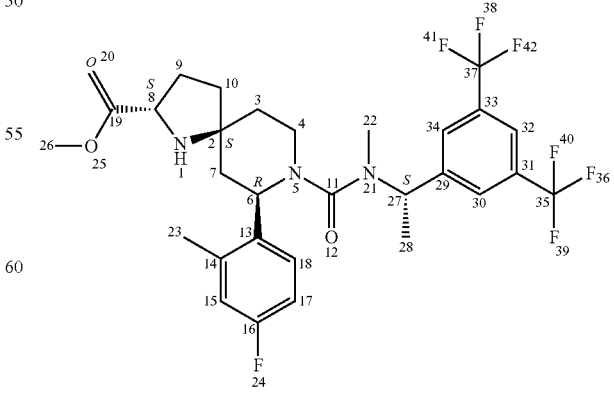

HPLC: Rt=5.20 mins; MS: m/z=604 [M+H]+ and 626 [M+Na]+.

Intermediate 30 phenylmethyl [(2R,4S)-1-{[{(1R)-1-[3,5-bis(trifluoromethyl)phenyl]ethyl}(methyl) amino]carbonyl}-2-(4-fluoro-2-methylphenyl)-4-(2-oxoethyl)-4-piperidinyl]carbamate

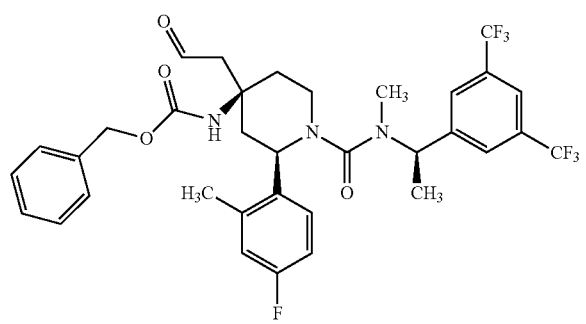 [SMILES: Cc1cc(F)ccc1[C@H]1C[C@@](CC=O)(NC(=O)OCc2ccccc2)CCN1C(=O)N(C)[C@H](C)c1cc(C(F)(F)F)cc(C(F)(F)F)c1]

In a solution of phenylmethyl [(2R,4S)-1-{[{(1R)-1-[3,5-bis(trifluoromethyl)phenyl]ethyl}(methyl)amino]carbonyl}-2-(4-fluoro-2-methylphenyl)-4-(2-propen-1-yl)-4-piperidinyl]carbamate (Intermediate 24, 1.2 g, 1.766 mmol) in dry Dichloromethane (DCM) (40 ml), at −78° C., ozone was bubbled until the mixture became cyan (7 minutes). Nitrogen was then bubbled for 30 minutes at the same temperature and the mixture became colourless. Dimethyl sulfide (20 ml, 270 mmol) was then added and the mixture was stirred overnight while the temperature was allowed to increase to r.t.

Volatiles were evaporated and the residue was purified by flash chromatography (SP4 system, 40+M cartridge, eluting from 100% cyclohexane to 50%:50% cyclohexane/ethyl acetate). Relevant fractions were collected and the solvent removed in vacuo affording the title compound (960 mg, 1.408 mmol, 80% yield) as a white solid. UPLC: Rt=0.96 mins (large peak), m/z=682 [M+H]+.

Intermediate 31 phenylmethyl {(2R,4S)-1-{[{(1R)-1-[3,5-bis(trifluoromethyl)phenyl]ethyl}(methyl)amino]carbonyl}-2-(4-fluoro-2-methylphenyl)-4-[(2E/2Z)-3-(methyloxy)-2-propen-1-yl]-4-piperidinyl}carbamate

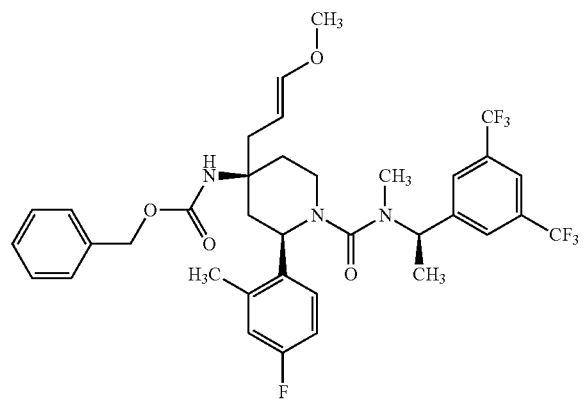

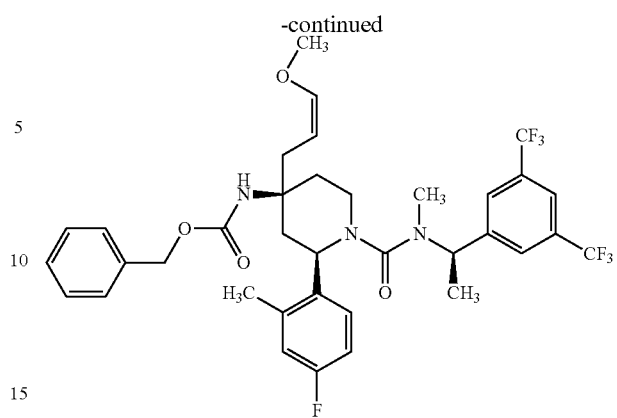

Methoxymethyltriphenylphosphonium chloride (405 mg, 1.181 mmol) was suspended in 5 ml of dry THF under N2 atmosphere. To this mixture, chilled at −30° C. potassium tert-butoxide (133 mg, 1.181 mmol) was added portionwise: intense red colour was observed. The solution was stirred at this temperature 15 mins.

In another flask phenylmethyl [(2R,4S)-1-{[{(1R)-1-[3,5-bis(trifluoromethyl)phenyl]ethyl}(methyl)amino]carbonyl}-2-(4-fluoro-2-methylphenyl)-4-(2-oxoethyl)-4-piperidinyl]carbamate (Intermediate 30, 230 mg, 0.337 mmol) was dissolved in 6 ml of THF and cooled to −20° C.

3 ml of Ylide solution were added dropwise to the solution of phenylmethyl [(2R,4S)-1-{[{(1R)-1-[3,5-bis(trifluoromethyl)phenyl]ethyl}(methyl)amino]carbonyl}-2-(4-fluoro-2-methylphenyl)-4-(2-oxoethyl)-4-piperidinyl]carbamate (Intermediate 30) and the temperature was allowed to rise to rt. It was left stirring for 1 hr. The reaction was cooled again to −20° C. and further ylide solution (2 ml) were added dropwise to the reaction mixture and it was left at rt for 4 hrs. Et2O was added to the reaction mixture and the organic phase was washed with NH4Cl aq and brine. The two phases were separated and the organic layer was dried over Na2SO4. The solid was filtered out and the solvent was removed in vacuo. The residue was purified via flash chromatography (flash master personal, 20 g cartridge eluting from 100% Cy to 70%:30% Cy:EtOAc). Relevant fractions were collected and the solvent removed obtaining the title compound (145 mg, 0.102 mmol, 30.3% yield) as a white foam; UPLC: 2 peaks Rt=1.02 and 1.04 mins, m/z=710 [M+H]+ and 732 [M+Na]+: mixture of geometric isomers (E/Z).

Intermediate 32 phenylmethyl (5S,7R)-8-{[{(1R)-1-[3,5-bis(trifluoromethyl)phenyl]ethyl}(methyl) amino]carbonyl}-7-(4-fluoro-2-methylphenyl)-2-hydroxy-1,8-diazaspiro[4.5]decane-1-carboxylate

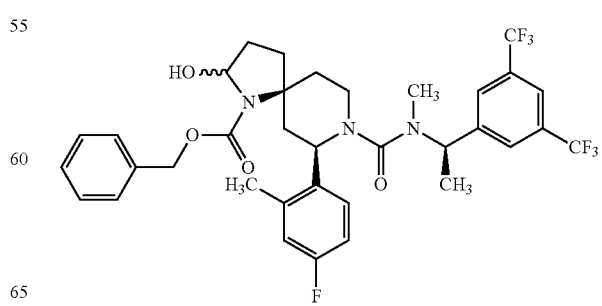

To a solution of Phenylmethyl {(2R,4S)-1-{[{(1R)-1-[3,5-bis(trifluoromethyl)phenyl]ethyl}(methyl)amino]carbonyl}-2-(4-fluoro-2-methylphenyl)-4-[(2E/2Z)-3-(methyloxy)-2-propen-1-yl]-4-piperidinyl}carbamate (Intermediate 31, 140 mg, 0.099 mmol) in Tetrahydrofuran (THF) (4 ml), at 0° C., 2N HCl (0.148 ml, 0.296 mmol) was added and the reaction was left stirring overnight at rt. To the solution were added NaHCO3 saturated solution and Et2O, the two phases were separated and the organic one was dried over Na2SO4. The solid was filtered out, the solvent was removed in vacuo obtaining the title compound (110 mg); UPLC: Rt=0.96 mins, m/z=696 [M+H]+.

Intermediate 33 phenylmethyl (5S,7R)-8-{[{(1R)-1-[3,5-bis(trifluoromethyl)phenyl]ethyl}(methyl) amino]carbonyl}-7-(4-fluoro-2-methylphenyl)-2-oxo-1,8-diazaspiro[4.5]decane-1-carboxylate

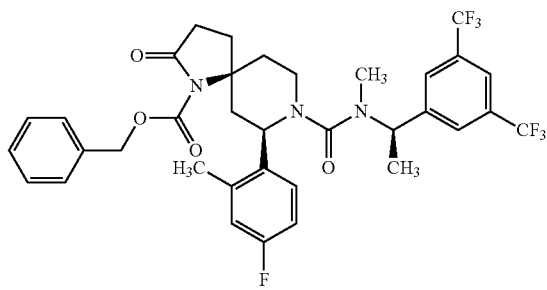 [SMILES: Cc1cc(F)ccc1[C@H]1C[C@]2(CCC(=O)N2C(=O)OCc2ccccc2)CCN1C(=O)N(C)[C@H](C)c1cc(C(F)(F)F)cc(C(F)(F)F)c1]

To a suspension of Pyridinium chlorochromate (PCC) (66.5 mg, 0.307 mmol) in DCM (2 ml) was added a solution of phenylmethyl (5S,7R)-8-{[{(1R)-1-[3,5-bis(trifluoromethyl)phenyl]ethyl}(methyl)amino]carbonyl}-7-(4-fluoro-2-methylphenyl)-2-hydroxy-1,8-diazaspiro[4.5]decane-1-carboxylate (Intermediate 32, 107 mg) in DCM (2 ml) and the reaction mixture was left stirring at it for 1 hr. Further pyridinium chlorochromate (PCC) (66.5 mg, 0.307 mmol) was added and the reaction mixture was left stirring overnight. To the mixture were added H2O and further DCM. The two phases were separated and the organic one was washed two times with water and filtered through a phase separator tube. The crude obtained after evaporation was purified by Flash Chromatography (20 g cartridge; eluting from 2:1 to 1:1 Cy:EtOAc). Relevant fractions were collected and the solvent removed in vacuo obtaining the title compound (86 mg) as a white solid; UPLC: Rt=0.95 mins, m/z=694 [M+H]+.

Intermediate 34

3-methyl 1-(phenylmethyl) (5S,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-1,3-dicarboxylate

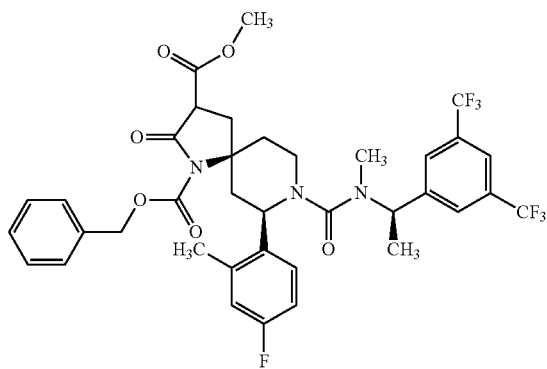

To a solution of phenylmethyl (5S,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-1-carboxylate (Intermediate 33, 85 mg) in Tetrahydrofuran (THF) (2 ml), at −78° C., LiHMDS (0.257 ml, 0.257 mmol) was added and left stirring at this temperature for 1 hr. methyl chloroformate (0.019 ml, 0.245 mmol) was added at the same temperature and the reaction was left at this temperature for 2 hrs. To the solution was added NH4Cl saturated solution, followed by DCM and water. The two phases were separated and the aqueous one was extracted with DCM. The combined organic layers were filtered through a phase separator tube and the solvent was removed in vacuo obtaining the title compound (83 mg) as a white foam. This batch was used in the next step without further purification. 1H NMR (500 MHz, DMSO-d6) δ ppm 8.01 (s, 1H) 7.67 (s, 2H) 7.24-7.48 (m, 5H) 6.85-7.00 (m, 2H) 6.70-6.84 (m, 1H) 5.09-5.29 (m, 3H) 4.34 (d, 1H) 3.99 (t, 1H) 3.70 (s, 3H) 2.65 (s, 3H) 2.58-3.44 (m, 2H) 2.34 (s, 3H) 1.54-2.45 (m, 6H) 1.47 (d, 3H); Mixture of two diastereoisomers ratio ~50:50 (for example visible on the signal of CH(6) see annotation in the spectrum). The atom numbering shown in the following structure is included for the purpose of correlation with the NMR data only.

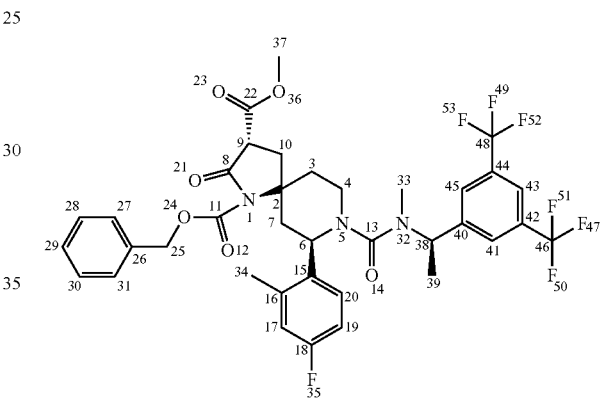

UPLC: Rt=0.96 mins, m/z=752 [M+H]+; HPLC: Rt=7.23 mins.

Intermediate 35 methyl (5S,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-3-carboxylate

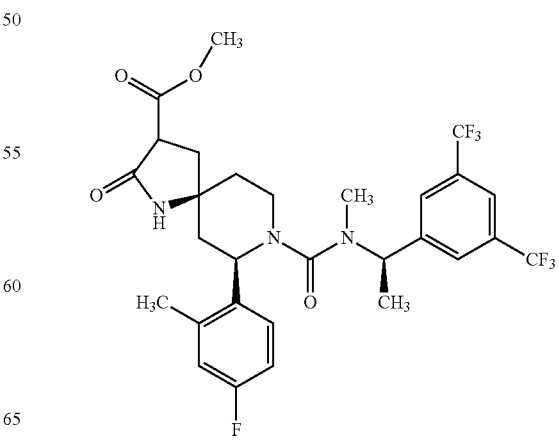

3-methyl 1-(phenylmethyl) (5S,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-1,3-dicarboxylate (Intermediate 34, 78 mg) was dissolved in Methanol (3 ml), Pd/C (8.83 mg, 8.30 μmol) was added and the suspension was left stirring at rt, under a H2 atmosphere (1 atm), for 1 hr. The Pd was filtered out and the solvent was removed obtaining the title compound (60 mg); UPLC: Rt=0.82 mins, m/z=618 [M+H]+.

Intermediate 36 methyl (5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-3-carboxylate

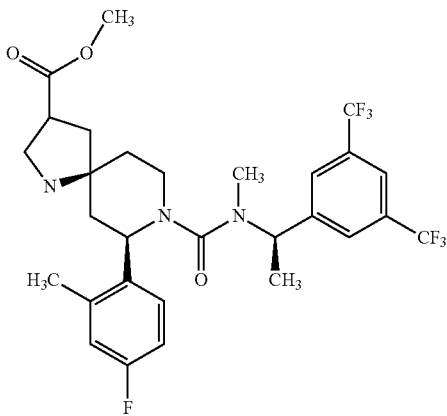

A solution of Trimethyloxonium tetrafloroborate (10.35 mg, 0.070 mmol) and methyl (5S,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-3-carboxylate (Intermediate 35, 36 mg) in Dichloromethane (DCM) (2 ml) was stirred at rt for 2 hrs. The mixture was washed with NaHCO3 saturated solution and the aqueous layer was extracted with DCM. The organic layers were combined, filtered through a phase separator tube and concentrated obtaining the intermediate methyl (5S,7R)-8-{[{(1R)-1-[3,5-bis(trifluoromethyl)phenyl]ethyl}(methyl)amino]carbonyl}-7-(4-fluoro-2-methylphenyl)-2-(methyloxy)-1,8-diazaspiro[4.5]dec-1-ene-3-carboxylate:

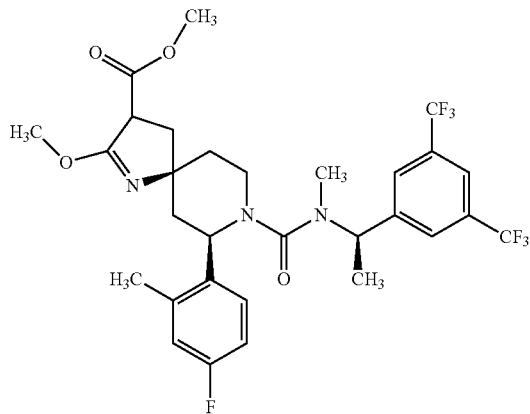

UPLC: Rt=0.92 mins, m/z=632 [M+H]+.
This intermediate was dissolved in Methanol (2 ml) and to the solution, cooled to 0° C., sodium cyanoborohydride (10.99 mg, 0.175 mmol) was added. A solution of 1.25M HCl in MeOH was added maintaining the pH around 3-4 and the reaction was left stirring at rt for 4 hrs. To the solution were added NaHCO3 saturated solution and DCM and the aqueous layer was extracted with DCM. Organic layers were combined and filtered through a phase separator tube and concentrated. The crude was purified by SP4 (12M cartridge; eluent from 90:10 to 50:50 Cy:EtOAc). Relevant fractions were collected obtaining methyl (5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-3-carboxylate (24 mg, 0.040 mmol) as a mixture of diastereoisomers; 1H NMR (500 MHz, DMSO-d6) δ ppm 7.99 (s, 1H) 7.70 (s, 2H) 7.08-7.24 (m, 1H) 6.84-6.98 (m, 1H) 6.71-6.80 (m, 1H) 5.21-5.43 (m, 1H) 3.95-4.24 (m, 1H) 3.60 (s, 3H) 3.20-3.41 (m, 1H) 2.93-3.21 (m, 2H) 2.82-2.99 (m, 1H) 2.66-2.80 (m, 1H) 2.71 (s, 3H) 2.34 (s, 3H) 2.32 (br. s., 1H) 1.48 (d, 3H) 1.34-2.13 (m, 6H); the sample consists of a mixture of two diastereoisomers (visible on the signal of OCH3(22)). The atom numbering shown in the following structure is included for the purpose of correlation with the NMR data only.

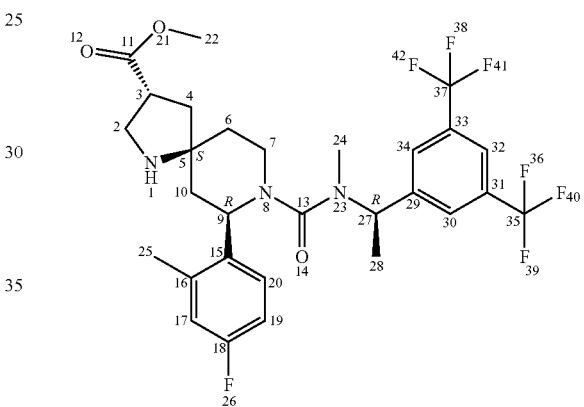

UPLC: Rt=0.71 mins, m/z=604 [M+H]+.

Intermediate 37

(2R,4E/Z)-N-{(1R)-1-[3,5-bis(trifluoromethyl)phenyl]ethyl}-2-(4-fluoro-2-methylphenyl)-4-(hydroxyimino)-N-methyl-1-piperidinecarboxamide

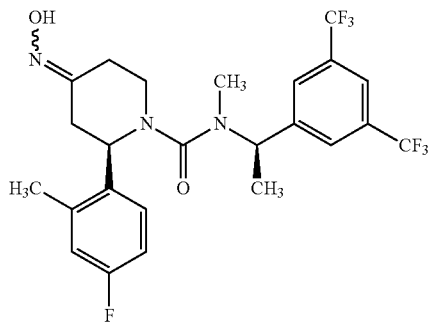 [SMILES: Cc1cc(F)ccc1[C@H]1CC(=NO)CCN1C(=O)N(C)[C@H](C)c1cc(C(F)(F)F)cc(C(F)(F)F)c1]

(2R)-N-{(1R)-1-[3,5-bis(trifluoromethyl)phenyl]ethyl}-2-(4-fluoro-2-methylphenyl)-N-methyl-4-oxo-1-piperidinecarboxamide (WO0232867 4 g, 7.93 mmol) was dissolved in Ethanol (20 ml). The solution was warmed to 50° C., then hydroxylamine hydrochloride (1.212 g, 17.45 mmol) and sodium bicarbonate (1.199 g, 14.27 mmol) were added and the mixture was stirred at 50° C. for 2 hrs. The solvent was removed in vacuo, then EtOAc was added followed by saturated NaHCO3 solution and water. The two phases were separated and the organic phase was dried and evaporated to give the title compound (4.1 g, 7.89 mmol, 100% yield) as a mixture of geometric isomers (E/Z); UPLC: 2 peaks Rt=0.84 and 0.86 mins, m/z=520 [M+H]+.

Intermediate 38

(2R)-N-{(1R)-1-[3,5-bis(trifluoromethyl)phenyl] ethyl}-2-(4-fluoro-2-methylphenyl)-N-methyl-4-nitro-1-piperidinecarboxamide

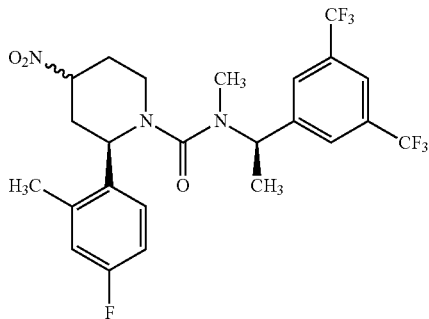 [SMILES: Cc1cc(F)ccc1[C@H]1CC([N+](=O)[O-])CCN1C(=O)N(C)[C@H](C)c1cc(C(F)(F)F)cc(C(F)(F)F)c1]

(2R,4E/Z)-N-{(1R)-1-[3,5-bis(trifluoromethyl)phenyl] ethyl}-2-(4-fluoro-2-methylphenyl)-4-(hydroxyimino)-N-methyl-1-piperidinecarboxamide (Intermediate 37, 4.1 g, 7.89 mmol) was dissolved in Acetonitrile (80 ml), UREA (2.370 g, 39.5 mmol) and Na2HPO4 (9.36 g, 65.9 mmol) were added and the mixture warmed at 80° C. for 30 mins. Then mCPBA (4.10 g, 23.76 mmol) was added portionwise (15 mins between one addition and the other). The reaction was refluxed for 5 hrs. Then it was cooled to rt and the salts were filtered and washed with CH3CN. The volume of the filtered solution was reduced and it was diluted with Et2O and NaHCO3 saturated solution. The phases were separated, washed with Na2S2O3 saturated solution, water and NaHCO3 saturated solution until disappearance of MCPBA. The organic phase was dried over Na2SO4, and evaporated to give the title compound (4.1 g, 7.66 mmol, 97% yield) as a mixture of diastereoisomers; UPLC: 2 peaks Rt=0.94 and 0.96 mins, m/z=536 [M+H]+.

Intermediate 39 dimethyl 2-[(2R,4R)-1-{[{(1R)-1-[3,5-bis(trifluoromethyl)phenyl]ethyl}(methyl) amino]carbonyl}-2-(4-fluoro-2-methylphenyl)-4-nitro-4-piperidinyl] butanedioate)

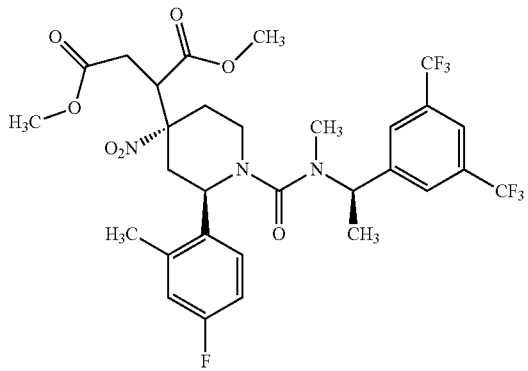 [SMILES: COC(=O)CC(C(=O)OC)[C@@]1([N+](=O)[O-])CCN(C(=O)N(C)[C@H](C)c2cc(C(F)(F)F)cc(C(F)(F)F)c2)[C@@H](c2ccc(F)cc2C)C1]

(2R)-N-{(1R)-1-[3,5-bis(trifluoromethyl)phenyl]ethyl}-2-(4-fluoro-2-methylphenyl)-N-methyl-4-nitro-1-piperidinecarboxamide (Intermediate 38, 500 mg, 0.934 mmol) was dissolved in Dimethyl Sulfoxide (DMSO) (6 ml) and to this solution were added potassium fluoride (271 mg, 4.67 mmol) and tetrabutylammonium iodide (345 mg, 0.934 mmol). The mixture was left stirring at rt for 10 min (pink mixture), then dimethyl maleate (0.584 ml, 4.67 mmol) was added. The mixture was left stirring at rt for 4 hrs and at 40° C. for 1 hr, then water and Et2O were added. The two phases were separated and the organic one was washed with 1N HCl. The organic phase was dried over Na2SO4 and evaporated to dryness. The crude was purified by flash chromatography (40M cartridge; eluting from 9:1 to 7:3 Cy:EtOAc) to give two batches of the title compound:

1st batch (388 mg, 0.571 mmol, 61.1% yield); 1H NMR (500 MHz, DMSO-$d_6$) δ ppm 8.00 (s, 1H) 7.68 (s, 2H) 7.21-7.28 (m, 1H) 6.90-7.01 (m, 1H) 6.73-6.86 (m, 1H) 5.25-5.40 (m, 1H) 4.05 (d, 1H) 3.60 (s, 3H) 3.56 (s, 3H) 3.27-3.45 (m, 1H) 2.71 (s, 3H) 2.52-2.92 (m, 4H) 2.30 (s, 3H) 1.53-2.47 (m, 4H) 1.48 (d, 3H), the sample consists of a mixture of two diastereoisomers at CH(9) (~55:45). The relative stereochemistry anti has been determined by dipolar correlations between CH(9) and CH2(5)ax. The atom numbering shown in the following structure is included for the purpose of correlation with the NMR data only.

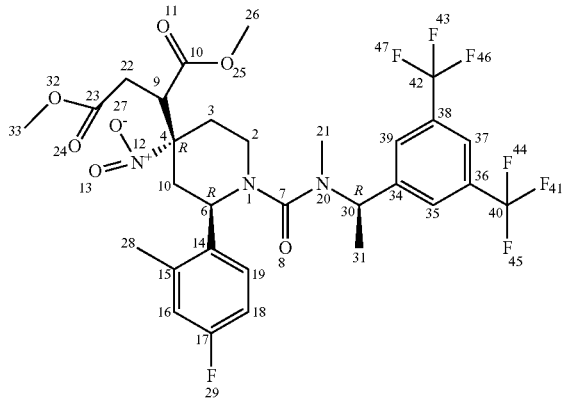

UPLC: Rt=0.96 mins, m/z=680 [M+H]+.
2nd batch (111 mg, 0.163 mmol, 17.49% yield).

Intermediate 40 methyl (5R,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5] decane-4-carboxylate

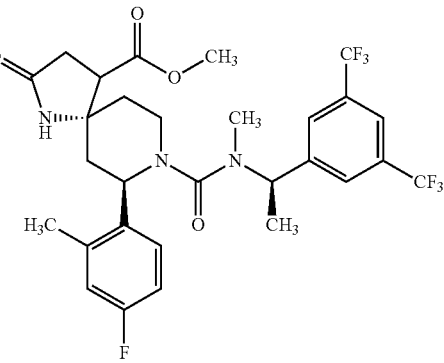

Dimethyl 2-[(2R,4R)-1-{[{(1R)-1-[3,5-bis(trifluoromethyl)phenyl]ethyl}(methyl)amino]carbonyl}-2-(4-fluoro-2-methylphenyl)-4-nitro-4-piperidinyl]butanedioate (Intermediate 39, 250 mg, 0.368 mmol) was dissolved in Methanol (6 ml) and to this solution was added Raney®-Nickel. The reaction mixture was left stirring under H2 at 1 atm for 3 hrs. The solid was filtered out and the solution was refluxed for 2 hrs. The solvent was removed in vacuo and the crude purified by Flash Chromatography (SP4, 25M cartridge, eluent from 90%:10% to 70%:30% Cy:EtOAc). The solvent was removed in vacuo obtaining the title compound (70 mg, 0.113 mmol, 30.8% yield) as a mixture of diastereoisomers. UPLC: Rt=0.83 mins, nm/z=618 [M+H]+.

Intermediate 41 methyl (5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-4-carboxylate

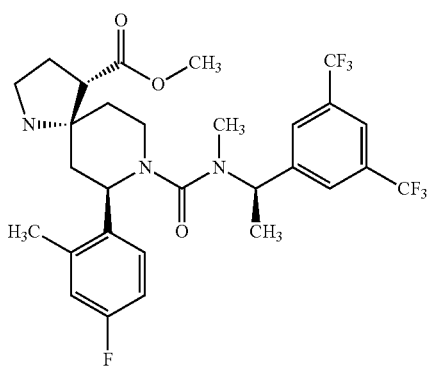 [SMILES: COC(=O)[C@H]1CCN[C@@]12CCN(C(=O)N(C)[C@H](C)c1cc(C(F)(F)F)cc(C(F)(F)F)c1)[C@@H](c1ccc(F)cc1C)C2]

A solution of trimethyloxonium tetrafluoroborate (33.5 mg, 0.226 mmol) and methyl (5R,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-4-carboxylate (Intermediate 40, 70 mg, 0.113 mmol) in Dichloromethane (DCM) (3 ml) was stirred at rt overnight. The mixture was washed with NaHCO3 saturated solution and the aqueous layer was extracted with DCM. The organic layers were combined, filtered through a phase separator tube and concentrated. The residue obtained was dissolved in Methanol (3 ml) and to the solution, cooled to 0° C., was added sodium cyanoborohydride (28.5 mg, 0.454 mmol). A solution of 1.25M HCl in MeOH was added maintaining the pH around 3-4 and the reaction was left stirring at rt for 2 hrs. To the solution NaHCO3 saturated solution and DCM were added and the aqueous layer was extracted with DCM. Organic layers were combined and filtered through a phase separator tube and concentrated. The crude was purified by SP4 (12M cartridge, eluting from 90%:10% to 50%:50% Cy:EtOAc). Relevant fractions were collected obtaining the title compound (12 mg, 0.020 mmol, 17.54% yield) as a single diastereoisomer. 1H NMR (500 MHz, DMSO-$d_6$) δ ppm 7.99 (s, 1H) 7.68 (s, 2H) 7.13 (dd, 1H) 6.89 (dd, 1H) 6.76 (t, 1H) 5.20-5.40 (m, 1H) 4.43 (dd, 1H) 3.61 (s, 3H) 3.11-3.19 (m, 1H) 3.01-3.10 (m, 1H) 2.89-2.97 (m, 1H) 2.80-2.88 (m, 1H) 2.71 (s, 3H) 2.45-2.55 (m, 1H) 2.32 (s, 3H) 1.85-2.05 (m, 2H) 1.61-1.71 (m, 1H) 1.53-1.60 (m, 2H) 1.46 (d, 3H) 1.38-1.50 (m, 1H); Despite some signals' overlapping (H10 eq and H6 eq), causing missing information, stereochemistry could be assigned on the basis of the following noe data:

1. no noe H4 with either H9ax or H7ax was observed suggesting stereochemistry at 5 as drawn.

2. observed noe H4/H10ax, indicating the position of the carbonyl group on the same part as C6 and C7 with respect to the pirrolidine plane, and confirming stereochemistry at 5 as drawn.

Verification was carried out also at the following step (see Example 10) confirming this result. The atom numbering shown in the following structure is included for the purpose of correlation with the NMR data only.

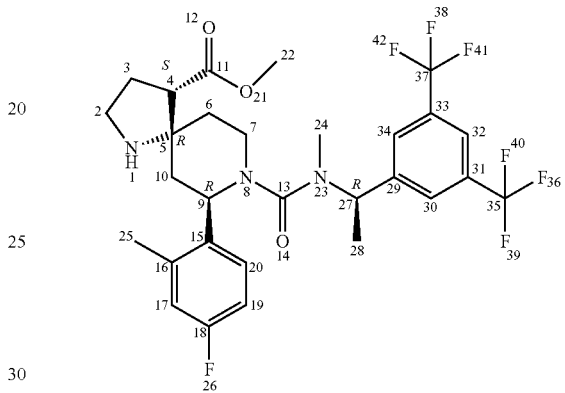

UPLC: Rt=0.71 mins, m/z=604 [M+H]+.

Intermediate 42

(5S,7R)-N-{(1R)-1-[3,5-bis(trifluoromethyl)phenyl]ethyl}-7-(4-fluoro-2-methylphenyl)-N-methyl-2-oxo-1,8-diazaspiro[4.5]decane-8-carboxamide

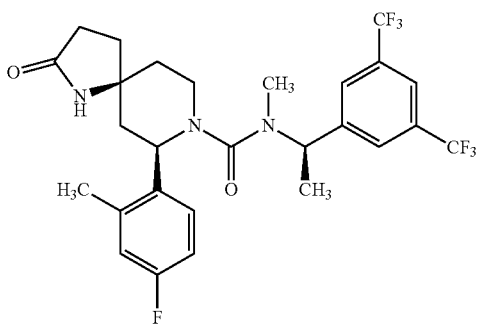 [SMILES: Cc1cc(F)ccc1[C@H]1C[C@]2(CCC(=O)N2)CCN1C(=O)N(C)[C@H](C)c1cc(C(F)(F)F)cc(C(F)(F)F)c1]

phenylmethyl (5S,7R)-8-{[{(1R)-1-[3,5-bis(trifluoromethyl)phenyl]ethyl}(methyl)amino]carbonyl}-7-(4-fluoro-2-methylphenyl)-2-oxo-1,8-diazaspiro[4.5]decane-1-carboxylate (Intermediate 33 70 mg, 0.101 mmol) was dissolved in Methanol (3 ml) and to the solution was added Pd/C (10.74 mg, 10.09 μmol) The suspension was left stirring under H2 atmosphere for 30 mins. The palladium was filtered out and the solvent removed in vacuo obtaining the title compound (53.6 mg, 0.096 mmol, 95% yield); UPLC: Rt=0.81 mins, m/z=560 [M+H]+; MS: m/z=560 [M+H]+ and 582 [M+Na]+.

Intermediate 43

1-(1,1-dimethylethyl) 2-methyl (2S,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-1,2-dicarboxylate

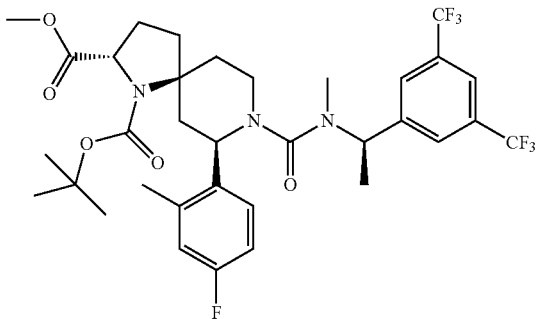 [SMILES: COC(=O)[C@@H]1CC[C@@]2(CCN(C(=O)N(C)[C@H](C)c3cc(C(F)(F)F)cc(C(F)(F)F)c3)[C@@H](c3ccc(F)cc3C)C2)N1C(=O)OC(C)(C)C]

To a solution of methyl (2S,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 13, 12 g, 19.88 mmol) in dry Dichloromethane (DCM) (80 ml) TEA (4.16 ml, 29.8 mmol) and then BOC-Anhydride (5.54 ml, 23.86 mmol) were added and the reaction mixture was stirred overnight at r.t. The reaction was diluted with NaHCO3 sat. sol. (400 ml) and two phases were separated. The organic layer was dried (Na2SO4), filtered and evaporated in vacuo and the residue was purified by flash chromatography on silica gel using a Biotage 65i as column and Cyclohexane to Cyclohexane/Ethyl acetate 7:3 as eluent affording the title compound (12.2 g, 17.43 mmol, y=87.7%).

UPLC: Rt=1.04 mins, m/z 704 [M+H]$^+$

Intermediate 44 methyl (2R,5S,7R)-8-{[{(1R)-1-[3,5-bis(trifluoromethyl)phenyl]ethyl}(methyl)amino]carbonyl}-7-(4-fluoro-2-methylphenyl)-2-methyl-1,8-diazaspiro[4.5]decane-2-carboxylate and

Intermediate 45 methyl (2S,5S,7R)-8-{[{(1R)-1-[3,5-bis(trifluoromethyl)phenyl]ethyl}(methyl)amino]carbonyl}-7-(4-fluoro-2-methylphenyl)-2-methyl-1,8-diazaspiro[4.5]decane-2-carboxylate

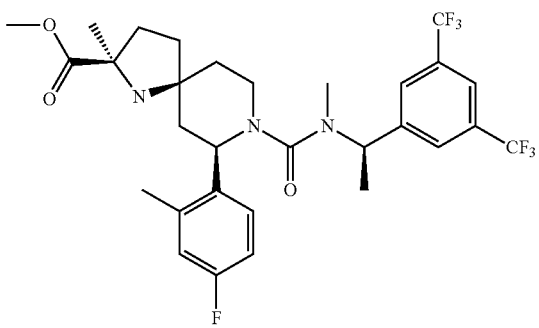

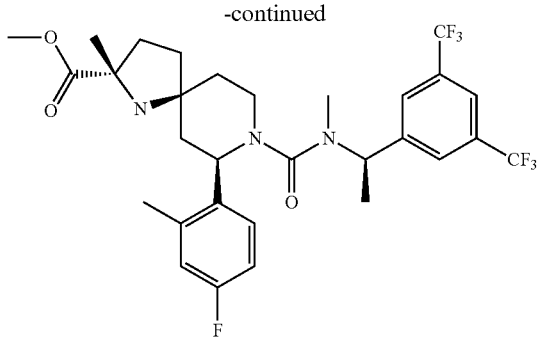

To a solution of 1-(1,1-dimethylethyl) 2-methyl (2S,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-1,2-dicarboxylate (Intermediate 43, 1 g, 1.421 mmol) in dry Tetrahydrofuran (THF) (16 ml) at -78° C. LiHMDS 1M in THF (2.132 ml, 2.132 mmol) was added and the reaction mixture was stirred for 10 mins at r.t. iodomethane (0.355 ml, 5.68 mmol) was then added and the reaction mixture was stirred for 30 mins at r.t. The reaction was quenched with brine (1 ml), diluted with water (10 ml) and extracted with ethyl acetate (3×30 ml). Combined organic layers were dried (Na2SO4), filtered and evaporated in vacuo. The residue was dissolved in Dichloromethane (15 ml) and the stirring solution was cooled at 0° C. TFA (5 ml, 64.9 mmol) was added and the reaction mixture was stirred at 0° C. for 1.30 h. The solvent and the excess of TFA were evaporated in vacuo. The residue was dissolved in 20 ml of ethyl acetate and washed with NaHCO3 sat. sol. (5 ml). The organic layer was dried, filtered and evaporated and the residue was purified by flash chromatography on silica gel using a Biotage SNAP 50 g as column and Cyclohexane to Cyclohexane/Ethyl acetate 1:1 as eluent affording the title compounds:

Intermediate 44 308 mg, 0.499 mmol, y=35.1%). HPLC: Rt=6.46 mins; MS: m/z 618 [M+H]$^+$
and Intermediate 45 353 mg, 0.571 mmol, y=40.2%); HPLC: Rt=6.37 mins; MS: m/z 618 [M+H]$^+$

Intermediate 46

(2R,5S,7R)-N-{(1R)-1-[3,5-bis(trifluoromethyl)phenyl]ethyl}-7-(4-fluoro-2-methylphenyl)-N,2-dimethyl-2-{[(trimethylsilyl)oxy]methyl}-1,8-diazaspiro[4.5]decane-8-carboxamide

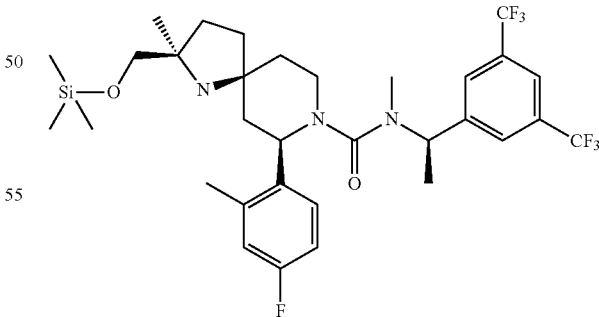

To a solution of (2R,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide (Example 18, 80 mg, 0.136 mmol) in Dichloromethane (DCM) (2 ml), TEA (0.021 ml, 0.149 mmol) was added and the reaction mixture was stirred at 0° C. for 5 min. TMS-Cl (0.026 ml, 0.204 mmol) was added dropwise and mixture was stirred at the same temperature overnight. Water (2 ml) was added and two phases were separated. The organic layer was dried and evaporated in vacuo affording the title compound (84 mg) that was used in the next step without further purifications. LC/MS (Basic gradient conditions): Rt=4.205 min, m/z 662 [M+H]⁺.

Intermediate 47

(2R,4S,8a'R)-N-{(1R)-1-[3,5-bis(trifluoromethyl) phenyl]ethyl}-2-(4-fluoro-2-methylphenyl)-3'-hydroxy-N,8a'-dimethylhexahydro-1H-spiro[piperidine-4,6'-pyrrolo[2,1-c][1,4]oxazine]-1-carboxamide

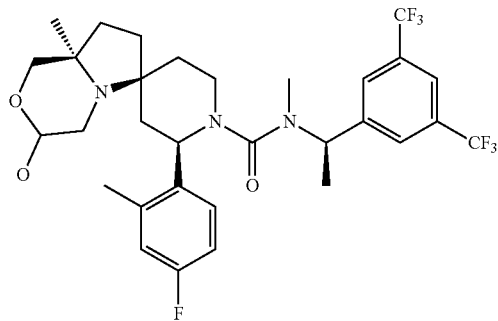

Ethanedial (0.218 ml, 1.904 mmol) was dissolved in Acetonitrile (1 ml) and stirred at r.t. A solution of (2R,5S,7R)-N-{(1R)-1-[3,5-bis(trifluoromethyl)phenyl]ethyl}-7-(4-fluoro-2-methylphenyl)-N,2-dimethyl-2-{[(trimethylsilyl) oxy]methyl}-1,8-diazaspiro[4.5]decane-8-carboxamide (Intermediate 46, 84 mg, 0.127 mmol) in acetonitrile (1 ml) was added dropwise and mixture was stirred at r.t. for 30 minutes then sodium cyanoborohydride (9.57 mg, 0.152 mmol) was added and the reaction mixture was stirred overnight. The reaction was quenched with water (2 ml) and acetonitrile was removed under vacuo. Aqueous layer was extracted with Ethyl acetate (3×5 ml). Organic phase was dried and evaporated in vacuo affording the title compound (84 mg) that was used in the next step without further purifications.
UPLC: Rt=0.78 mins, m/z 632 [M+H]⁺

Intermediate 48

(2S,5S,7R)-N-{(1R)-1-[3,5-bis(trifluoromethyl)phenyl]ethyl}-7-(4-fluoro-2-methylphenyl)-N,2-dimethyl-2-{[(trimethylsilyl)oxy]methyl}-1,8-diazaspiro [4.5]decane-8-carboxamide

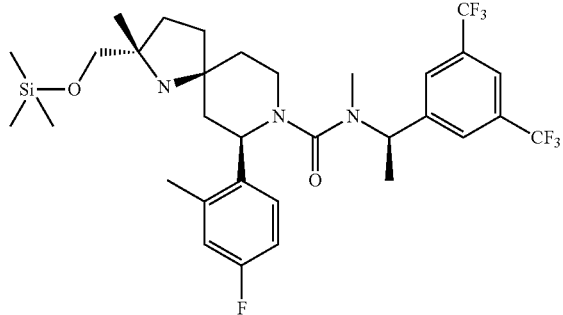 [SMILES: Cc1cc(F)ccc1[C@H]1C[C@@]2(CCN1C(=O)N(C)[C@H](C)c1cc(C(F)(F)F)cc(C(F)(F)F)c1)CC[C@@](C)(CO[Si](C)(C)C)N2]

To a solution of (2S,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide (Example 19, 80 mg, 0.136 mmol) in dichloromethane (DCM) (2 ml), TEA (0.021 ml, 0.149 mmol) was added and the reaction mixture was stirred at 0° C. for 5 min. TMS-Cl (0.026 ml, 0.204 mmol) was added dropwise and mixture was stirred at the same temperature overnight. Water (2 ml) was added and two phases were separated. The organic layer was dried and evaporated in vacuo affording the title compound (88 mg) that was used in the next step without further purifications.
LCMS (Basic gradient conditions): Rt=4.205, m/z 662 [M+H]⁺

Intermediate 49

(2R,4S,8a'S)-N-{(1R)-1-[3,5-bis(trifluoromethyl) phenyl]ethyl}-2-(4-fluoro-2-methylphenyl)-3'-hydroxy-N,8a'-dimethylhexahydro-1H-spiro[piperidine-4,6'-pyrrolo[2,1-c][1,4]oxazine]-1-carboxamide

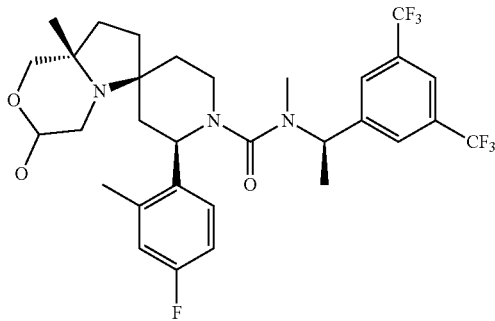

Ethanedial (0.229 ml, 1.995 mmol) was dissolved in Acetonitrile (1 ml) and stirred at rt. A solution of (2S,5S,7R)-N-{(1R)-1-[3,5-bis(trifluoromethyl)phenyl]ethyl}-7-(4-fluoro-2-methylphenyl)-N,2-dimethyl-2-{[(trimethylsilyl) oxy]methyl}-1,8-diazaspiro[4.5]decane-8-carboxamide (Intermediate 48, 88 mg, 0.133 mmol) in acetonitrile (1 ml) was added dropwise and mixture was stirred at RT for 30 min then sodium cyanoborohydride (10.03 mg, 0.160 mmol) was added and the reaction mixture was stirred overnight. The reaction was quenched with water (2 ml) and acetonitrile was removed under vacuo. Aqueous layer was extracted with ethyl acetate (3×5 ml). Organic phase was dried and evaporated in vacuo affording the title compound (88 mg) that was used in the next step without further purifications.
UPLC: Rt=0.77 mins, m/z 632 [M+H]⁺

Intermediate 50

(2R,4S,8a'S)-N-{(1R)-1-[3,5-bis(trifluoromethyl) phenyl]ethyl}-2-(4-fluoro-2-methylphenyl)-3'-hydroxy-N-methylhexahydro-1H-spiro[piperidine-4,6'-pyrrolo[2,1-c][1,4]oxazine]-1-carboxamide

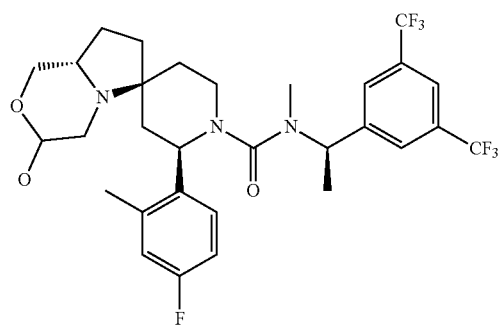

Ethanedial (0.299 ml, 2.61 mmol) was dissolved in Acetonitrile (1.5 ml) and stirred at rt. A solution of (2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide (Example 26, 100 mg, 0.174 mmol) in acetonitrile (1 ml) was added dropwise and mixture was stirred at RT for 30 min then sodium cyanoborohydride (13.10 mg, 0.208 mmol) was added and the reaction mixture was stirred overnight. The reaction was quenched with water (2 ml) and acetonitrile was removed under vacuo. Aqueous layer was extracted with Ethyl acetate (3×5 ml). Organic phase was dried and evaporated in vacuo affording the title compound (115 mg) that was used in the next step without further purifications.

UPLC: Rt=0.70 mins, m/z 618 [M+H]$^+$

Intermediate 51

(2R,4S,8a'R)-N-{(1R)-1-[3,5-bis(trifluoromethyl)phenyl]ethyl}-2-(4-fluoro-2-methylphenyl)-3'-hydroxy-N-methylhexahydro-1H-spiro[piperidine-4,6'-pyrrolo[2,1-c][1,4]oxazine]-1-carboxamide

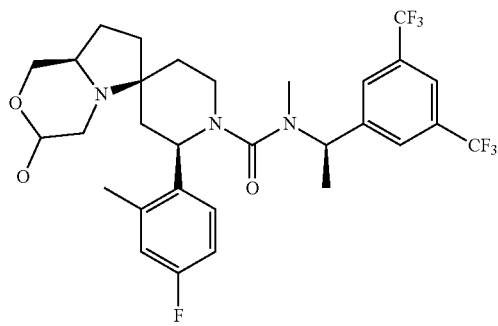

Ethanedial (0.299 ml, 2.61 mmol) was dissolved in Acetonitrile (1.5 ml) and stirred at rt. A solution of (2R,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide (Example 24, 100 mg, 0.174 mmol) in acetonitrile (1 ml) was added dropwise and mixture was stirred at rt for 30 min then sodium cyanoborohydride (13.10 mg, 0.208 mmol) was added and the reaction mixture was stirred overnight. The reaction was quenched with water (2 ml) and acetonitrile was removed under vacuo. Aqueous layer was extracted with Ethyl acetate (3×5 ml). Organic phase was dried and evaporated in vacuo affording the title compound (120 mg) that was used in the next step without further purifications.

UPLC: Rt=0.71 mins, m/z 618 [M+H]$^+$

Intermediate 52 methyl (2R)-2-({[(1,1-dimethylethyl)oxy]carbonyl}amino)-4-pentenoate

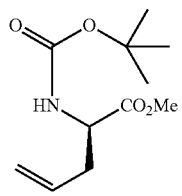 [SMILES: C=CC[C@@H](NC(=O)OC(C)(C)C)C(=O)OC]

To a suspension of (2R)-2-amino-4-pentenoic acid (6 g, 52.1 mmol, Aldrich) in dry methanol (60 ml) chilled at 0° C. by an ice bath under an argon atmosphere, thionyl chloride (7.61 ml, 104 mmol) was carefully added over 10 minutes keeping internal temperature below 10° C. Solid dissolved and the homogeneous colourless solution was allowed to reach room temperature and left to stir overnight.

The mixture was evaporated to dryness and the residue was diluted in 1,4-Dioxane (60.0 ml) and sat. NaHCO$_3$ solution was cautiously added in order to reach a basic pH and get the free base (a clear homogeneous solution was obtained). Di-tert-butyl dicarbonate (14.52 ml, 62.5 mmol) was added portionwise and the mixture stirred for 20 hours at room temperature, during which time some white solid precipitated.

EtOAc (200 ml) and water (50 ml) were added and the phases were separated. The aqueous phase was further back-extracted with EtOAc (200 ml) and finally the collected organics were washed with brine (50 ml).

After drying over Na$_2$SO$_4$ and evaporation of the solvent, 16 g of crude material were recovered as colourless oil that was purified with SiO$_2$ flash chromatography (biotage 65m) eluting with cyclohexane/AcOEt 9/1 (Rf=0.3). Evaporation of volatiles afforded title compound (12 g, 52.3 mmol, 100% yield) as colourless oil.

UPLC: Rt=0.68 mins, m/z=230 [M+H]+.

1H NMR (400 MHz, CHLOROFORM-d) δ ppm 5.53-5.84 (m, 1H), 4.90-5.36 (m, 3H), 4.27-4.53 (m, 1H), 3.76 (s, 3H), 2.31-2.77 (m, 2H), 1.46 (s, 9H)

Intermediate 53

(2R)-N-{(1R)-1-[3,5-bis(trifluoromethyl)phenyl]ethyl}-2-(4-fluoro-2-methylphenyl)-N-methyl-4-methylidene-1-piperidinecarboxamide

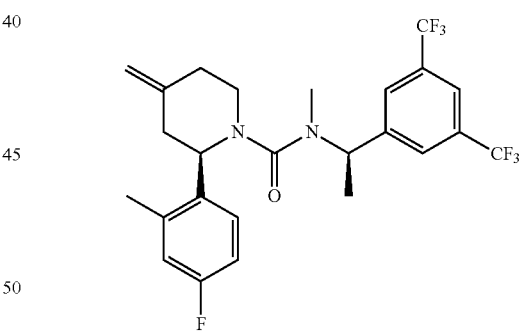

To a solution of potassium tert-butoxide (1.491 g, 12.89 mmol) in dry tetrahydrofuran (THF) (50 ml) under an argon atmosphere, methyltriphenylphosphonium bromide (4.60 g, 12.89 mmol) was added and the resulting heterogeneous yellow mixture was heated at reflux for 1 h. The slurry was then chilled at −15° C. and a solution of (2R)-N-{(1R)-1-[3,5-bis(trifluoromethyl)phenyl]ethyl}-2-(4-fluoro-2-methylphenyl)-N-methyl-4-oxo-1-piperidinecarboxamide (WO02328675 g, 9.91 mmol) in dry THF (20 ml) was added dropwise to the mixture in about 20 min not allowing the internal temperature to exceed −10° C. At the end of the addition, colour turned orange and after 10 min bath temperature was raised to 0° C. Reaction was left stirring at this temperature for 10 min then at room temperature for 1.5 h.

Reaction mixture was quenched with sat NH₄Cl (30 mL)/water (30 ml). Taken up with AcOEt (200 mL). Phases were separated and the aqueous one back-extracted with AcOEt (200 ml). Combined organics were dried over MgSO₄ and evaporated to dryness. Crude material (12 g as pale yellow solid) was purified by SiO₂ flash chromatography (biotage 65i) eluting with cyclohexane/AcOEt from 95/5 to 85/15 to give title compound (4.79 g, 9.53 mmol, 96% yield) as thick pale yellow oil.

UPLC: Rt 1.08 min, m/z=503 [M+H]⁺.

¹H NMR (400 MHz, CHLOROFORM-d) δ ppm 7.79 (s, 1H), 7.65 (s, 2H), 7.36-7.42 (m, 1H), 6.75-6.93 (m, 2H), 5.41-5.54 (m, 1H), 4.83-4.93 (m, 2H), 4.66-4.76 (m, 1H), 3.04-3.31 (m, 2H), 2.68 (s, 3H), 2.38 (s, 3H), 2.32-2.68 (m, 4H), 1.54 (d, 3H)

Intermediate 54 methyl (2R,4E)-4-[(2R)-1{[{(1R)-1-[3,5-bis(trifluoromethyl)phenyl]ethyl}(methyl)amino]carbonyl}-2-(4-fluoro-2-methylphenyl)-4-piperidinylidene]-2-({[(1,1-dimethylethyl)oxy]carbonyl}amino)butanoate as mixture E/Z

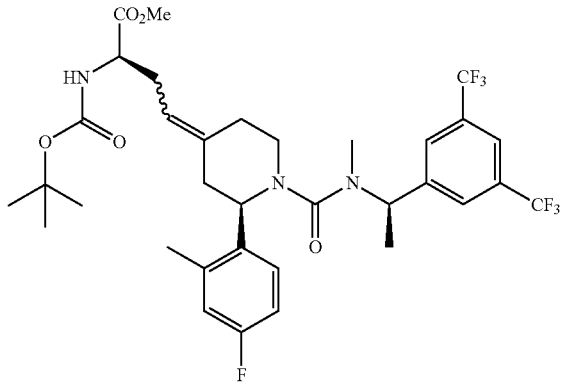 [SMILES: COC(=O)[C@@H](CC=C1CCN(C(=O)N(C)[C@H](C)c2cc(C(F)(F)F)cc(C(F)(F)F)c2)[C@@H](c2ccc(F)cc2C)C1)NC(=O)OC(C)(C)C]

A solution of (2R)-N-{(1R)-1-[3,5-bis(trifluoromethyl)phenyl]ethyl}-2-(4-fluoro-2-methylphenyl)-N-methyl-4-methylidene-1-piperidinecarboxamide (intermediate 53 3 g, 5.97 mmol) and methyl (2R)-2-({[(1,1-dimethylethyl)oxy]carbonyl}amino)-4-pentenoate (4.11 g, 17.91 mmol) in dry, degassed dichloromethane (DCM) (24 ml), was added to a flame dried round bottomed flask containing (1,3-bis-(2,4,6-trimethylphenyl)-2-imidazolidinylidene)dichloro(o-isopropoxyphenylmethylene)ruthenium, Hoveyda-Grubbs catalyst 2ⁿᵈ generation, (0.187 g, 0.299 mmol) under a nitrogen atmosphere. The green mixture was stirred and heated at reflux for 30 h (T bath=47° C.).

Reaction mixture was evaporated to small volume and loaded on to a SiO₂ column. Purification eluting with cyclohexane/AcOEt from 8/2 to 7/3 afforded, after evaporation of solvent, the title compound as an off white foam, (3.92 g, 5.57 mmol, 93% yield) as mixture of isomers E/Z.

UPLC: Rt=1.05 min, m/z=704 [M+H]⁺; and Rt=1.06 min, m/z=704 [M+H]⁺

¹H NMR (400 MHz, DMSO-d₆) δ ppm 7.98 (s, 1H), 7.72 (s, 2H), 6.75-7.44 (m, 5H), 3.74-5.55 (m, 5H), 3.61 (s, 3H), 2.61 (s, 3H), 2.28 (s, 3H), 2.07-3.47 (m, 6H), 1.46-1.58 (m, 3H), 1.36 (s, 9H).

Intermediate 55 methyl (2R,7R)-8-{[{(1R)-1-[3,5-bis(trifluoromethyl)phenyl]ethyl}(methyl)amino]carbonyl}-7-(4-fluoro-2-methylphenyl)-4-iodo-1,8-diazaspiro[4.5]decane-2-carboxylate

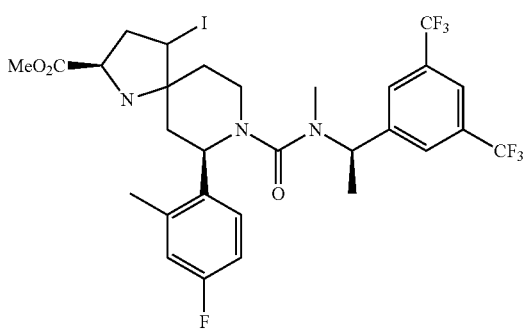 [SMILES: COC(=O)[C@H]1CC(I)C2(CCN(C(=O)N(C)[C@H](C)c3cc(C(F)(F)F)cc(C(F)(F)F)c3)[C@@H](c3ccc(F)cc3C)C2)N1]

1ˢᵗᵒ Step:

To a solution of methyl (2R,4E)-4-[(2R)-1-{[{(1R)-1-[3,5-bis(trifluoromethyl)phenyl]ethyl}(methyl)amino]carbonyl}-2-(4-fluoro-2-methylphenyl)-4-piperidinylidene]-2-({[(1,1-dimethylethyl)oxy]carbonyl}amino)butanoate (intermediate 54, 1.5 g, 2.132 mmol) in dry dichloromethane (DCM) (20 ml) at 0° C. under a nitrogen atmosphere, TFA (5 ml, 64.9 mmol) was added dropwise and the solution stirred at 0° C. for 3 h.

The mixture was evaporated to dryness without heating, then treated with 10% K₂CO₃ aqueous solution (20 ml) and DCM (40 ml). Phases were separated and the aqueous one back-extracted with DCM (2×50 ml). Combined organics were dried over Mg₂SO₄ and concentrated to dryness to get a crude residue 1.132 g as pale brown foam, used without further purification in the next iodo-cyclization step.

2ⁿᵈ Step:

To the crude residue coming from step 1°, 1.132 g, in dry acetonitrile (15 ml) under N₂ at room temperature was added solid sodium bicarbonate (0.537 g, 6.39 mmol) followed portionwise by solid iodine (1.623 g, 6.39 mmol).

Mixture was left stirring overnight at room temperature.

Mixture was treated with aqueous sat. Na₂S₂O₃ (30 ml) and DCM (100 ml). Phases were separated and the aqueous one back-extracted with DCM (2×50 ml). Combined organics were dried over Mg₂SO₄ and evaporated to dryness to get crude material, 1.4 g as pale yellow thick oil, that was purified by SiO₂ flash chromatography eluting with cyclohexane/AcOEt from 9/1 to 1/1, to give, after evaporation of volatiles, title compound (867 mg, 1.189 mmol, 55.8% yield; spot Rf=0.58 plus spot Rf=0.51 cyclohexane/AcOEt 1/1).

UPLC: Rt=0.89 min, m/z=730 [M+H]⁺; Rt=0.9 min, m/z=730 [M+H]⁺; Rt=1.02 min, m/z=730 [M+H]⁺.

¹H NMR (400 MHz, CHLOROFORM-d) δ ppm 7.81 (s, 1H), 7.60 (s, 2H), 7.14-7.23 (m, 1H), 6.76-6.92 (m, 2H), 5.39-5.70 (m, 1H), 3.82-4.79 (m, 3H), 3.81 (s, 3H), 2.77-3.43 (m, 2H), 2.74 (s, 3H), 2.44 (s, 3H), 1.64-2.20 (m, 6H), 1.49 (s, 3H).

Example 1

(5R,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide (diastereoisomer 1)

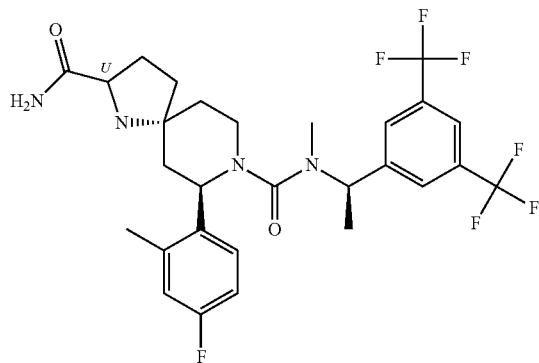

In a sealed tube a solution of Methyl (5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (diastereoisomer 1) (Intermediate 7, 6 mg, 9.94 μmol) in 7N Ammonia in MeOH (5 mL, 35.0 mmol) was stirred at 25° C. for 1 day and then it was left still for 2 days. The solvent was evaporated to dryness and the crude was purified by silica cartridges twice (1st time: from 1:0 to 95:5 DCM/MeOH; 2nd time: EtOAc and then 97.5:2.5 DCM/0.5M NH₃ in MeOH) to give the title compound (4.7 mg, 7.99 μmol, 80% yield). 1H NMR (500 MHz, DMSO-d₆) δ ppm 7.95-8.03 (m, 1H) 7.63-7.73 (m, 2H) 7.29-7.37 (m, 1H) 7.12-7.20 (m, 1H) 7.00-7.06 (m, 1H) 6.86-6.92 (m, 1H) 6.71-6.79 (m, 1H) 5.27-5.38 (m, 1H) 4.34-4.43 (m, 1H) 3.54-3.64 (m, 1H) 3.16-3.25 (m, 1H) 3.03-3.14 (m, 1H) 2.67-2.84 (m, 3H) 2.30-2.41 (m, 3H) 1.96-2.08 (m, 1H) 1.62-1.80 (m, 2H) 1.38-1.58 (m, 8H).

Example 2

(5R,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide (diastereoisomer 2)

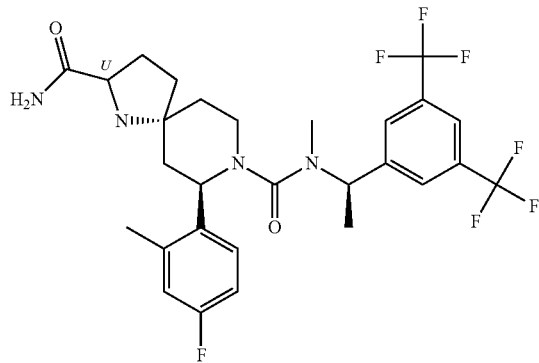

A solution of Methyl (5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (diastereoisomer 2) (Intermediate 8, 18 mg, 0.030 mmol) in 7N Ammonia in MeOH (5 mL, 35.0 mmol) was stirred at 25° C. for 1 day and then it was left still for 2 days. The solvent was evaporated to dryness and the crude was purified by SCX and silica cartridges (from 1:0 to 97.5:2.5 DCM/0.5 M NH₃ in MeOH) to give two batches of the title compound as colourless oil (total amount: 14.9 mg, 0.025 mmol, 84% yield). 1H NMR (400 MHz, DMSO-d₆) δ ppm 7.90-8.08 (m, 1H) 7.62-7.77 (m, 2H) 7.26-7.46 (m, 1H) 7.04-7.23 (m, 2H) 6.84-6.96 (m, 1H) 6.69-6.80 (m, 1H) 5.24-5.41 (m, 1H) 4.31-4.49 (m, 1H) 3.49-3.65 (m, 1H) 3.10-3.25 (m, 1H) 2.94-3.08 (m, 1H) 2.61-2.87 (m, 3H) 2.35 (s, 3H) 1.92-2.10 (m, 1H) 1.62-1.84 (m, 2H) 1.38-1.60 (m, 8H).

Example 3

(2R,5S,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide

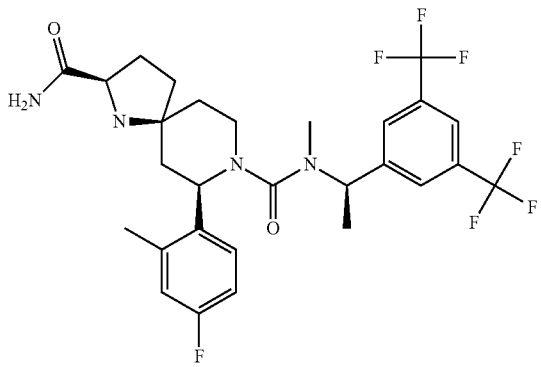 [SMILES: Cc1cc(F)ccc1[C@H]1C[C@]2(CC[C@H](C(N)=O)N2)CCN1C(=O)N(C)[C@H](C)c1cc(C(F)(F)F)cc(C(F)(F)F)c1]

In a sealed tube a solution of Methyl (2R, 5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 12, 21.6 mg, 0.036 mmol) in 7N Ammonia in MeOH (5 mL, 35.0 mmol) was stirred at 25° C. for 1 day. The solvent was evaporated to dryness and the crude was purified by silica cartridge (2 g) (at first EtOAc and then 97.5:2.5 DCM/0.5 M NH₃ in MeOH) to give 17.8 mg of the title compound as a white foam. 1H NMR (500 MHz, DMSO-d₆) δ ppm 8.00 (s, 1H) 7.70 (s, 2H) 7.28 (d, 1H) 7.15 (dd, 1H) 7.03 (d, 1H) 6.92 (dd, 1H) 6.78 (t, 1H) 5.31 (q, 1H) 4.14 (dd, 1H) 3.47 (t, 1H) 3.27-3.38 (m, 1H) 2.75 (s, 3H) 2.76 (t, 1H) 2.32 (s, 3H) 2.05-2.15 (m, 1H) 1.68-1.85 (m, 3H) 1.52-1.68 (m, 3H) 1.47 (d, 3H) 1.39-1.54 (m, 1H). NMR analysis revealed the presence of a large amount of DCM (~55% w/w). HPLC: Rt 4.90 mins. This batch was used directly in the next step.

Example 4

(2R,5S,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide hydrochloride

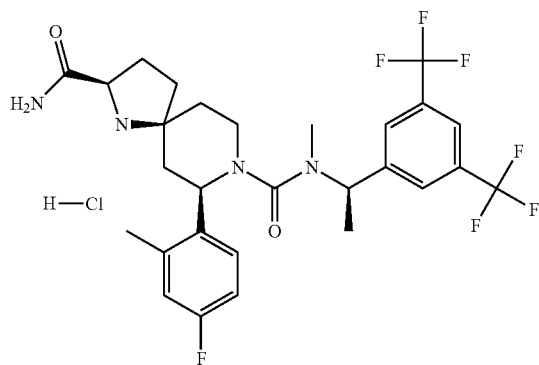

To a cold (0° C.) solution of (2R,5S,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide (Example 3, 16.9 mg) in Diethyl ether (1 mL) was added dropwise 1N HCl in Diethyl ether (0.039 mL, 0.039 mmol) and the reaction mixture was stirred for 30 mins. The solvent was evaporated to dryness to give the title compound (18.1 mg) as a white solid.

1H NMR (500 MHz, DMSO-d₆) d ppm 9.29 (br. s., 1H) 8.52 (br. s., 1H) 8.01 (s, 1H) 7.87 (br. s., 1H) 7.74 (br. s., 1H) 7.69 (s, 2H) 7.16 (dd, 1H) 6.96 (dd, 1H) 6.78-6.91 (m, 1H) 5.20-5.36 (m, 1H) 4.07-4.39 (m, 2H) 3.36-3.47 (m, 1H) 2.78-2.88 (m, 1H) 2.75 (s, 3H) 2.42-2.48 (m, 1H) 2.32-2.37 (m, 3H) 1.78-2.20 (m, 7H) 1.47 (d, 3H). NMR analysis revealed the presence of a large amount of DCM (~20% w/w). HPLC: Rt 4.89 mins. This batch of the title compound was dried under vacuum overnight at 40° C. to give 14 mg.

Example 5

(2S,5S,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide

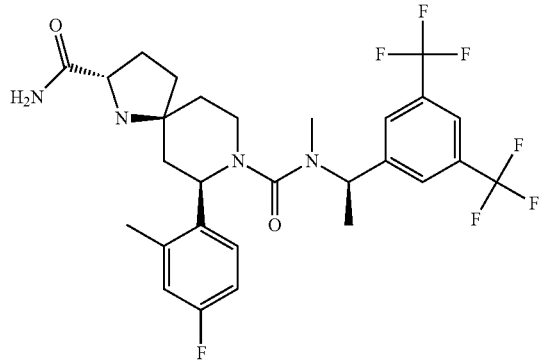 [SMILES: Cc1cc(F)ccc1[C@H]1C[C@]2(CC[C@@H](C(N)=O)N2)CCN1C(=O)N(C)[C@H](C)c1cc(C(F)(F)F)cc(C(F)(F)F)c1]

In a sealed tube a solution of Methyl (2S,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 13, 24.1 mg, 0.04 mmol) in 7N Ammonia in MeOH (5 mL, 35.0 mmol) was stirred at 25° C. for 1 day. The solvent was evaporated to dryness and the crude was purified twice by silica cartridges (2 g) (1ˢᵗ time: with EtOAc and then 97.5:2.5 DCM/0.5 M NH₃ in MeOH and 2ⁿᵈ time: from 98.75:1.25 to 95:5 DCM/0.5 M NH₃ in MeOH) to give the title compound (22.5 mg, 0.038 mmol, 96% yield) as a white solid. 1H NMR (400 MHz, DMSO-d6) δ ppm 7.92-8.05 (m, 1H) 7.61-7.77 (m, 2H) 7.21-7.27 (m, 1H) 7.13-7.19 (m, 1H) 6.87-6.97 (m, 2H) 6.73-6.83 (m, 1H) 5.25-5.37 (m, 1H) 4.08-4.20 (m, 1H) 3.44-3.55 (m, 1H) 3.26-3.38 (m, 1H) 2.57-2.85 (m, 4H) 2.26-2.36 (m, 3H) 1.98-2.16 (m, 1H) 1.41-1.82 (m, 10H).

Example 6

(2S,5S,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide hydrochloride

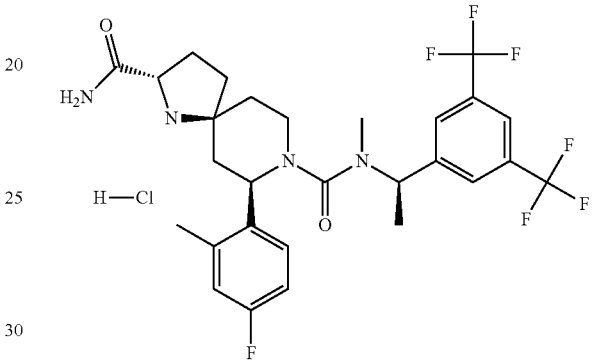

To a cold (0° C.) solution of (2S,5S,7R)-N⁸-{(1R)-1-[3,5-bis(trifluoromethyl)phenyl]ethyl}-7-(4-fluoro-2-methylphenyl)-N⁸-methyl-1,8-diazaspiro[4.5]decane-2,8-dicarboxamide (Example 5, 21 mg, 0.036) in Diethyl ether (1 mL) was added 1N HCl in Diethyl ether (60 μl, 0.060 mmol) and the reaction mixture was stirred for 30 mins. The solvent was evaporated to dryness to give the title compound (23.8 mg, quantitative yield) as a white solid. 1H NMR (500 MHz, DMSO-d₆) δ ppm 7.61-8.07 (m, 5H) 7.11-7.24 (m, 1H) 6.91-6.99 (m, 1H) 6.79-6.90 (m, 1H) 5.23-5.34 (m, 1H) 4.13-4.31 (m, 2H) 3.26-3.47 (m, 1H) 2.79-2.92 (m, 1H) 2.70-2.79 (m, 3H) 1.79-2.66 (m, 11H) 1.38-1.54 (m, 3H). Presence of acid protons in the region between 8.30 and 9.66 ppm.

Example 7

(2R,5S,7R)-N⁸-{[3,5-bis(trifluoromethyl)phenyl]methyl}-7-(4-fluoro-2-methylphenyl)-N⁸-methyl-1,8-diazaspiro[4.5]decane-2,8-dicarboxamide

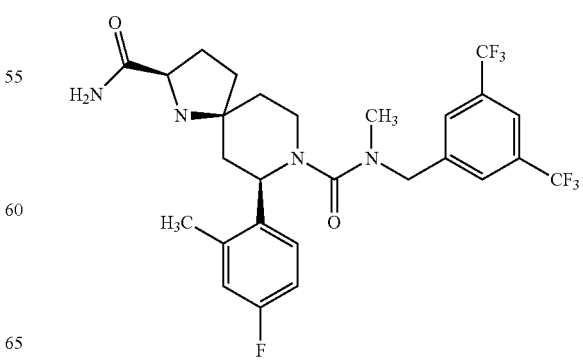

In a sealed tube a solution of methyl (5S,7R)-8-{[{[3,5-bis(trifluoromethyl)phenyl]methyl}(methyl)amino]carbonyl}-7-(4-fluoro-2-methylphenyl)-1,8-diazaspiro[4.5]decane-2-carboxylate (Intermediate 22, 63 mg, 0.107 mmol) in 7 N ammonia solution in MeOH (5 ml, 35.0 mmol) was shaken overnight. The solvent was evaporated to dryness and the crude was purified by flash-chromatography [Si cartridge (5 g), from 1:0 to 95:5 DCM/MeOH] to give the title compound (53.5 mg, 0.093 mmol, 87% yield) as a white solid. 1H NMR (500 MHz, DMSO-$d_6$) δ ppm 7.95 (s, 1H) 7.61 (s, 2H) 7.24-7.32 (m, 1H) 7.15-7.24 (m, 1H) 6.98-7.05 (m, 1H) 6.92 (d, 1H) 6.79 (t, 1H) 4.65 (d, 1H) 4.36 (d, 1H) 4.15 (d, 1H) 3.44-3.59 (m, 1H) 3.38 (d, 1H) 2.93 (s, 3H) 2.75 (t, 1H) 2.65 (br. s., 1 H) 2.33 (s, 3H) 1.99-2.21 (m, 1H) 1.51-1.93 (m, 6H) 1.45 (t, 1H); HPLC: Rt 4.88 mins; MS: m/z=575 [M+H]$^+$.

Example 8

(2R,5S,7R)-$N^8$-{[3,5-bis(trifluoromethyl)phenyl]methyl}-7-(4-fluoro-2-methylphenyl)-$N^8$-methyl-1,8-diazaspiro[4.5]decane-2,8-dicarboxamide hydrochloride

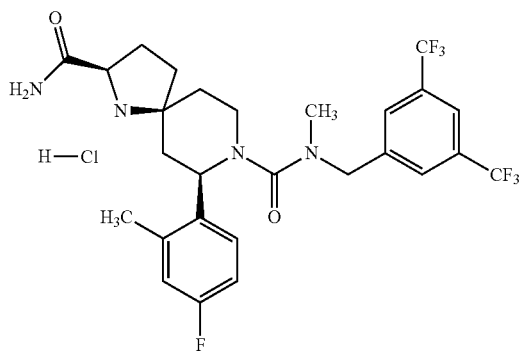

To a solution of (2R,5S,7R)-$N^8$-{[3,5-bis(trifluoromethyl)phenyl]methyl}-7-(4-fluoro-2-methylphenyl)-$N^8$-methyl-1,8-diazaspiro[4.5]decane-2,8-dicarboxamide (Example 7, 45.5 mg, 0.079 mmol) in Diethyl ether (1 ml) was added 1M HCl in Et2O (0.107 mL, 0.107 mmol) and the resulting mixture was stirred for 30 mins. The solvent was evaporated to give the title compound (40 mg, 0.065 mmol, 82% yield) as a white foam. 1H NMR (500 MHz, DMSO-$d_6$) δ ppm 9.49-9.85 (m, 1H) 8.36-8.60 (m, 1H) 7.96 (s, 1H) 7.92 (br. s., 1H) 7.69 (br. s., 1H) 7.61 (s, 2H) 7.16-7.27 (m, 1H) 6.96 (d, 1H) 6.84 (t, 1H) 4.65 (d, 1H) 4.35 (d, 1H) 4.24-4.32 (m, 1H) 4.20 (dd, 1H) 3.47 (d, 1H) 2.95 (s, 3H) 2.79 (t, 1H) 2.41-2.57 (m, 1H) 2.36 (s, 3H) 1.75-2.23 (m, 7H); HPLC: Rt 4.84 mins (free base); MS: m/z=575 [M+H]$^+$ (free base).

Example 9

(2S,5S,7R)-$N^8$-{[3,5-bis(trifluoromethyl)phenyl]methyl}-7-(4-fluoro-2-methylphenyl)-$N^8$-methyl-1,8-diazaspiro[4.5]decane-2,8-dicarboxamide

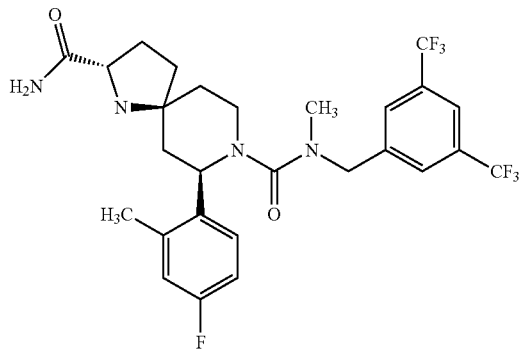 [SMILES: Cc1cc(F)ccc1[C@H]1C[C@]2(CC[C@@H](C(N)=O)N2)CCN1C(=O)N(C)Cc1cc(C(F)(F)F)cc(C(F)(F)F)c1]

In a sealed tube a solution of methyl (2S,5S,7R)-8-{[{[3,5-bis(trifluoromethyl)phenyl]methyl}(methyl)amino]carbonyl}-7-(4-fluoro-2-methylphenyl)-1,8-diazaspiro[4.5]decane-2-carboxylate (Intermediate 23, 80 mg, 0.136 mmol) in 7 M methanolic ammonia (5 ml, 35.0 mmol) was shaken overnight. The solvent was evaporated to dryness and the crude was purified by flash-chromatography (Si cartridge 5 g; from 1:0 to 95:5 DCM/MeOH) to give the title compound (74.4 mg, 0.129 mmol, 95% yield) as a white solid. 1H NMR (500 MHz, DMSO-$d_6$) δ ppm 7.95 (s, 1H) 7.61 (s, 2H) 7.15-7.28 (m, 2H) 6.84-6.97 (m, 2H) 6.78 (t, 1H) 4.63 (d, 1H) 4.34 (d, 1H) 4.08-4.22 (m, 1H) 3.48-3.55 (m, 1H) 3.33-3.42 (m, 1H) 2.93 (s, 3H) 2.76 (t, 1H) 2.65 (br. s., 1H) 2.31 (s, 3H) 2.01-2.16 (m, 1H) 1.38-1.85 (m, 7H); HPLC: Rt=4.91 mins; MS: m/z=575 [M+H]+ and 597 [M+Na]+.

Example 10

(2S,5S,7R)-$N^8$-{[3,5-bis(trifluoromethyl)phenyl]methyl}-7-(4-fluoro-2-methylphenyl)-$N^8$-methyl-1,8-diazaspiro[4.5]decane-2,8-dicarboxamide hydrochloride

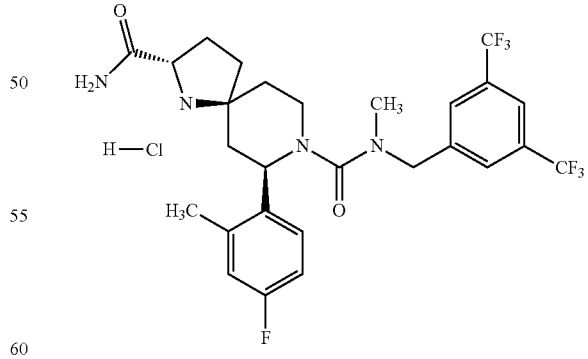

To a solution of (2S,5S,7R)-$N^8$-{[3,5-bis(trifluoromethyl)phenyl]methyl}-7-(4-fluoro-2-methylphenyl)-$N^8$-methyl-1,8-diazaspiro[4.5]decane-2,8-dicarboxamide (Example 9, 66 mg, 0.115 mmol) in Diethyl ether (1 ml) was added 1M HCl in Et2O (0.2 ml, 0.200 mmol) and the resulting mixture was stirred for 30 mins. The solvent was evaporated to dryness to give the title compound (61.7 mg, 0.101 mmol, 88% yield). 1H NMR (500 MHz, DMSO-$d_6$) δ ppm 9.50-9.86 (m, 1H) 8.25-8.50 (m, 1H) 7.87-8.01 (m, 2H) 7.67 (s, 1H) 7.60 (s, 2H) 7.20-7.29 (m, 1H) 6.90-7.00 (m, 1H) 6.80-6.90 (m, 1H) 4.58-4.70 (m, 1H) 4.31-4.43 (m, 1H) 4.13-4.30 (m, 2H) 3.42-3.54 (m, 1H) 2.95 (s, 3H) 2.75-2.88 (m, 1H) 1.74-2.67 (m, 11H). HPLC: Rt=4.82 mins (free base); MS: m/z=575 [M+H]+ and 597 [M+Na]+ (free base).

Example 11

(2R,5S,7R)-$N^8$-{(1S)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide

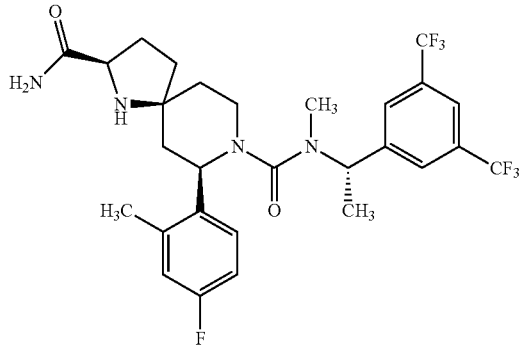 [SMILES: Cc1cc(F)ccc1[C@H]1C[C@]2(CC[C@H](C(N)=O)N2)CCN1C(=O)N(C)[C@@H](C)c1cc(C(F)(F)F)cc(C(F)(F)F)c1]

In a sealed tube a solution of methyl (2R,5S,7R)-8-{[{(1S)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 28, 90 mg, 0.149 mmol) in 7M methanolic ammonia (5 ml, 35.0 mmol) was shaken overnight. The solvent was evaporated and the crude was purified by flash-chromatography (Si cartridge 5 g; from 1:0 to 95:5 DCM/MeOH) to give the title compound (63.3 mg, 0.108 mmol, 72.1% yield) as a white solid. 1H NMR (500 MHz, DMSO-$d_6$) δ ppm 7.93 (s, 1H) 7.56 (s, 2H) 7.23-7.31 (m, 1H) 7.14-7.21 (m, 1H) 6.95-7.05 (m, 1H) 6.90 (d, 1H) 6.76 (t, 1H) 5.27-5.43 (m, 1H) 4.14 (d, 1H) 3.41-3.56 (m, 1H) 3.23-3.39 (m, 1H) 2.84 (s, 3H) 2.72 (t, 1H) 2.60-2.68 (m, 1H) 2.32 (s, 3H) 2.06-2.18 (m, 1H) 1.53-1.87 (m, 6H) 1.49 (d, 3H) 1.42 (t, 1H); HPLC: peak @ Rt=4.91 mins; MS: m/z=589 [M+H]+ and 611 [M+Na]+

Example 12

(2R,5S,7R)-$N^8$-{(1S)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide hydrochloride

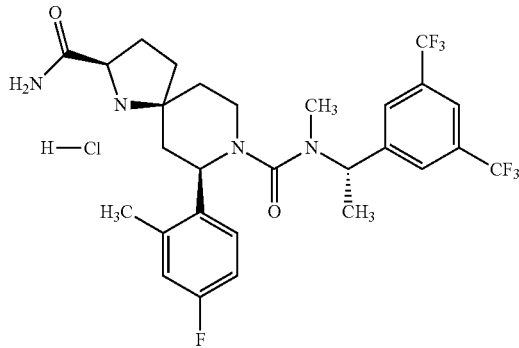

To a solution of (2R,5S,7R)-$N^8$-{(1S)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide (Example 11, 54 mg, 0.092 mmol) in Diethyl ether (1 ml) was added 1M HCl in Et2O (200 μL, 0.200 mmol) and the resulting mixture was stirred for 30 mins. Then the solvent was evaporated to dryness to give the title compound (57.4 mg, 0.091 mmol, 99% yield). 1H NMR (500 MHz, DMSO-$d_6$) δ ppm 9.35-9.68 (m, 1H) 8.35-8.60 (m, 1H) 7.95 (s, 1H) 7.90 (br. s., 1H) 7.70 (br. s., 1H) 7.56 (s, 2H) 7.11-7.25 (m, 1H) 6.94 (d, 1H) 6.80 (t, 1H) 5.28-5.39 (m, 1H) 4.13-4.35 (m, 2H) 3.44 (d, 1H) 2.85 (s, 3H) 2.77 (t, 1H) 2.40-2.59 (m, 1H) 2.35 (s, 3H) 1.75-2.21 (m, 7H) 1.50 (d, 3H); HPLC: Rt=4.95 mins (free base); MS: m/z=589 [M+H]+ (free base)

Example 13

(2S,5S,7R)-$N^8$-{(1S)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide

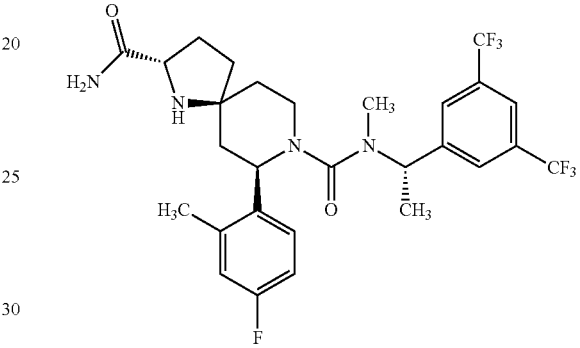

In a sealed tube a solution of methyl (2S,5S,7R)-8-{[{(1S)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 29, 80 mg, 0.133 mmol) in 7M methanolic ammonia (5 ml, 35.0 mmol) was shaken overnight. The solvent was evaporated and the crude was purified was purified by flash-chromatography (Si cartridge 5 g; from 1:0 to 95:5 DCM/MeOH) to give the title compound (76.1 mg, 0.129 mmol, 98% yield) as a white solid. 1H NMR (500 MHz, DMSO-$d_6$) δ ppm 7.94 (s, 1H) 7.56 (s, 2H) 7.24 (s, 1H) 7.15-7.21 (m, 1H) 6.84-6.96 (m, 2H) 6.71-6.81 (m, 1H) 5.30-5.40 (m, 1H) 4.09-4.18 (m, 1H) 3.47-3.57 (m, 1H) 3.24-3.40 (m, 1H) 2.83 (s, 3H) 2.59-2.78 (m, 2H) 2.31 (s, 3H) 2.03-2.17 (m, 1H) 1.42-1.85 (m, 10H). HPLC: Rt=4.91 mins; MS: m/z=589 [M+H]+ and 611 [M+Na]+.

Example 14

(2S,5S,7R)-$N^8$-{(1S)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide hydrochloride

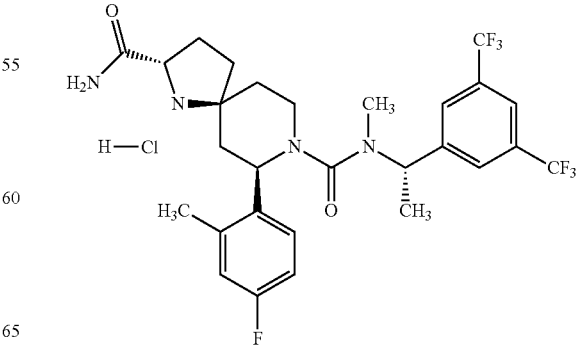

To a solution of (2S,5S,7R)-N$^8$-{(1S)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (Example 13, 67 mg, 0.113 mmol) in Diethyl ether (1 ml) was added 1M HCl in Et2O (200 µl, 0.200 mmol) and the resulting mixture was stirred for 30 mins. Then the solvent was evaporated to dryness to give the title compound (68.2 mg, 0.109 mmol, 96% yield) as a white solid. 1H NMR (500 MHz, DMSO-d$_6$) δ ppm 9.67 (br. s., 1H) 8.34 (br. s., 1H) 7.87-8.00 (m, 2H) 7.66 (s, 1H) 7.55 (s, 2H) 7.13-7.32 (m, 1H) 6.94 (d, 1H) 6.76-6.89 (m, 1H) 5.25-5.43 (m, 1H) 4.07-4.38 (m, 2H) 3.40-3.51 (m, 1H) 2.84 (s, 3H) 2.71-2.91 (m, 1H) 2.33 (s, 3H) 1.78-2.58 (m, 8H) 1.50 (d, 3H); HPLC: Rt=4.93 mins (free base); MS: peak @ m/z=589 [M+H]+ and 611 [M+Na]+ (free base).

Example 15 sodium (5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-3-carboxylate

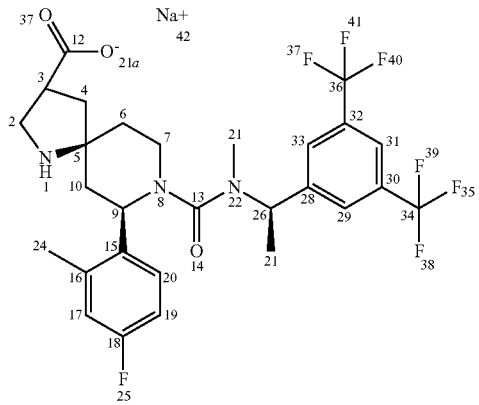

HPLC: two close peaks Rt=4.94 and 4.99 mins; UPLC: Rt=0.66 mins (large peak), m/z=590 [M−Na+2H]+.

Example 16 lithium (4S,5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-4-carboxylate

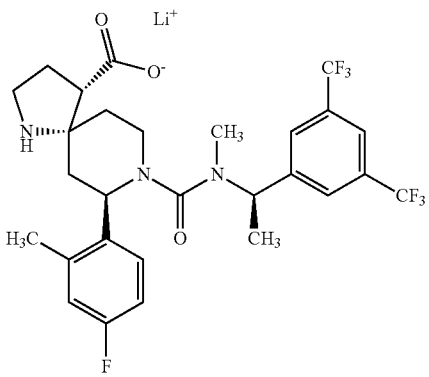 [SMILES: [Li+] ; Cc1cc(F)ccc1[C@H]1C[C@@]2(CCN1C(=O)N(C)[C@H](C)c1cc(C(F)(F)F)cc(C(F)(F)F)c1)NCC[C@@H]2C(=O)[O-]]

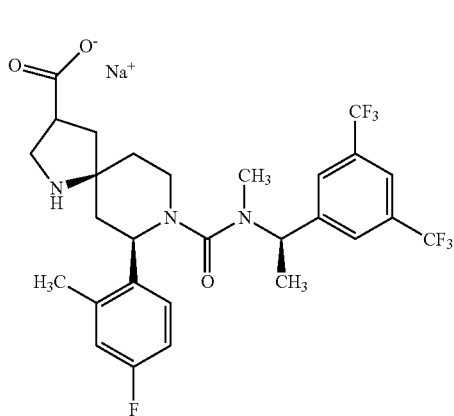

Methyl (5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-3-carboxylate (Intermediate 36, 22 mg, 0.036 mmol) was dissolved in Methanol (1 ml) and to this solution was added NaOH (1.604 mg, 0.040 mmol) in Water (0.2 ml). The reaction mixture was left stirring at rt overnight. Then the solution was heated at 45° C. for 12 more hrs. The solvents were removed in vacuo and the residue was washed several times with Et2O, the solid was dried under vacuum obtaining the title compound (20.3 mg, 0.033 mmol, 91% yield) as a mixture of diastereoisomers. ratio estimated ca. 2:1, 1H NMR (500 MHz, DMSO-d$_6$) δ ppm 7.99 (s, 1H) 7.70 (s, 2H) 7.04-7.22 (m, 1H) 6.85-6.98 (m, 1H) 6.66-6.82 (m, 1H) 5.20-5.43 (m, 1H) 4.06-4.25 (m, 1H) 2.77 (s, 3H) 2.55-3.57 (m, 5H) 2.33 (s, 3H) 1.46 (d, 3H) 1.06-2.06 (m, 6H);

Methyl (5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-4-carboxylate (Intermediate 41, 12 mg, 0.020 mmol) was dissolved in Methanol (0.3 ml) and Water (0.3 ml). To the mixture was added LiOH.H2O (0.918 mg, 0.022 mmol) and the reaction mixture was left stirring overnight at 50° C. To the solution was added Tetrahydrofuran (THF) (0.3 ml) and it was heated at 70° C. for 1 more hour. The solvent was removed in vacuo obtaining the title compound (11.2 mg, 0.019 mmol, 96% yield); 1H NMR (400 MHz, DMSO-d$_6$) δ ppm 7.98 (s, 1H) 7.69 (s, 2H) 7.07-7.15 (m, 1H) 6.84-6.91 (m, 1H) 6.69-6.79 (m, 1H) 5.25-5.38 (m, 1H) 4.43 (d, 1H) 2.98-3.23 (m, 2H) 2.69 (s, 3H) 2.60-2.92 (m, 2H) 2.31 (s, 3H) 1.56-2.04 (m, 5H) 1.48 (d, 3H) 1.40-1.54 (m, 1H) 1.33 (d, 1H). Stereochemistry consistent with the following data:
1. no noe with either H9ax or H7ax, suggesting stereochemistry at 5 as drawn
2. observed noe H4/H10 ax and H4/H10 eq, indicating stereochemistry at 4 and providing confirmation of stereochemistry at 5. The atom numbering shown in the following structure is included for the purpose of correlation with the NMR data only.

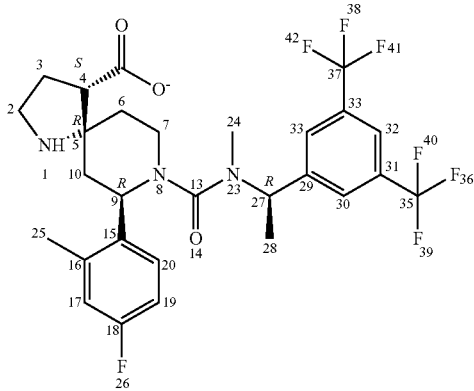

UPLC: Rt=0.67 mins, m/z=590 [M−Li+2H]+.

Example 17

(5S,7R)-N-{(1R)-1-[3,5-bis(trifluoromethyl)phenyl]ethyl}-7-(4-fluoro-2-methylphenyl)-N-methyl-1,8-diazaspiro[4.5]decane-8-carboxamide

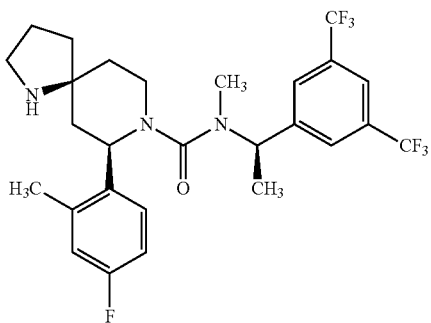 [SMILES: Cc1cc(F)ccc1[C@H]1C[C@]2(CCCN2)CCN1C(=O)N(C)[C@H](C)c1cc(C(F)(F)F)cc(C(F)(F)F)c1]

A solution of trimethyloxonium tetrafluoroborate (5.39 mg, 0.036 mmol) and (5S,7R)-N-{(1R)-1-[3,5-bis(trifluoromethyl)phenyl]ethyl}-7-(4-fluoro-2-methylphenyl)-N-methyl-2-oxo-1,8-diazaspiro[4.5]decane-8-carboxamide (Intermediate 42, 17 mg, 0.030 mmol) in Dichloromethane (DCM) (2 ml) was stirred at rt for 3 hrs. The mixture was washed with NaHCO3 saturated solution and the aqueous layer was extracted with DCM. The organic layers were combined, filtered through a phase separator tube and concentrated. The residue was dissolved in Methanol (2 ml) and to this solution, cooled to 0° C., was added Sodium cyanoborohydride (5.73 mg, 0.091 mmol). A solution of 1.25M HCl in MeOH was added maintaining the pH around 3-4 and the reaction was left stirring at rt overnight. To the solution NaHCO3 saturated solution and DCM were added and the aqueous layer was extracted with DCM. Organic layers were combined, filtered through a phase separator tube and concentrated. The crude was purified by SP4 (12M cartridge; eluting from 90%:10% to 50%:50% Cy:EtOAc). Relevant fractions were collected obtaining the title compound, (13 mg, 0.024 mmol, 78% yield); 1H NMR (500 MHz, DMSO-$d_6$) δ ppm 8.01 (s, 1H) 7.69 (s, 2H) 7.15-7.21 (m, 1H) 6.94 (dd, 1H) 6.83 (t, 1H) 5.20-5.41 (m, 1H) 4.02-4.27 (m, 1H) 3.35-3.44 (m, 1H) 3.02-3.20 (m, 2H) 2.86 (t, 1H) 2.76 (s, 3H) 2.34 (s, 3H) 1.59-2.19 (m, 8H) 1.47 (d, 3H); UPLC: Rt=0.68 mins, m/z=546 [M+H]+; HPLC: Rt=5.67 mins.

Example 18

(2R,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide

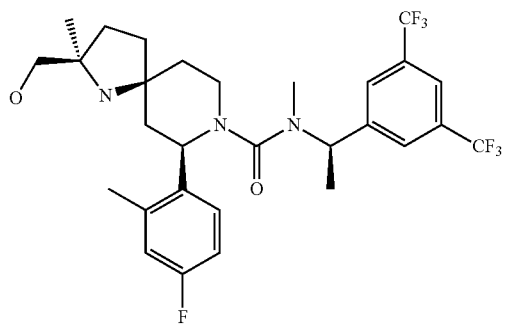 [SMILES: Cc1cc(F)ccc1[C@H]1C[C@@]2(CCN1C(=O)N(C)[C@H](C)c1cc(C(F)(F)F)cc(C(F)(F)F)c1)CC[C@](C)(CO)N2]

To a solution of methyl (2R,5S,7R)-8-{[{(1R)-1-[3,5-bis(trifluoromethyl)phenyl]ethyl}(methyl)amino]carbonyl}-7-(4-fluoro-2-methylphenyl)-2-methyl-1,8-diazaspiro[4.5]decane-2-carboxylate (Intermediate 44, 69 mg, 0.112 mmol) in Tetrahydrofuran (THF) (2.5 ml) at 0° C. lithium borohydride (0.164 ml, 0.335 mmol) was added and the reaction mixture was stirred at room temperature and under nitrogen atmosphere for 3 days. Volatiles were evaporated in vacuo and the residue was dissolved in Methanol (2 ml)/HCl 1 N in water (3 ml). After 1 h stirring combined solvents were evaporated in vacuo. The residue was dissolved in Ethyl acetate (4 ml) and washed with NaHCO3 sat. sol. (2×3 ml). Organic phase was dried and evaporated and the residue was purified by flash chromatography on silica gel using a Biotage SNAP 10 g as column and Dichloromethane/Methanol 95:5 as eluent affording the title compound (28 mg, 0.047 mmol, y=66.8%).

H-NMR (500 Mhz) DMSO-$d_6$ δ ppm 7.80 (s, 1H), 7.65 (s, 2H), 7.18 (dd, 1H), 6.73 (dd, 1H), 6.63-6.69 (m, 1H), 5.3 (q, 1H), 4.22 (dd, 1H), 3.26-3.36 (m, 1H), 3.18-3.25 (s, 2H), 2.85-2.96 (m, 1H), 2.72 (s, 3H), 2.31 (s, 3H), 1.97-2.04 (m, 1H), 1.95-1.98 (m, 2H), 1.68-1.79 (m, 4H), 1.59-1.66 (m, 1H), 1.41 (d, 3H), 1.08 (s, 3H).

UPLC: RT 0.73 mins, m/z 590 [M+H]+

Example 19

(2S,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide

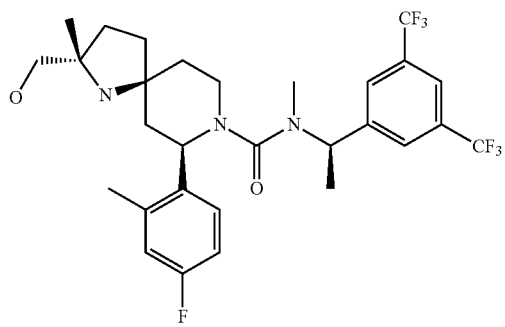 [SMILES: Cc1cc(F)ccc1[C@H]1C[C@@]2(CCN1C(=O)N(C)[C@H](C)c1cc(C(F)(F)F)cc(C(F)(F)F)c1)CC[C@@](C)(CO)N2]

To a solution of methyl (2S,5S,7R)-8-{[{(1R)-1-[3,5-bis(trifluoromethyl)phenyl]ethyl}(methyl)amino]carbonyl}-7-(4-fluoro-2-methylphenyl)-2-methyl-1,8-diazaspiro[4.5]decane-2-carboxylate (Intermediate 45, 72.9 mg, 0.118 mmol) in Tetrahydrofuran (THF) (2.5 ml) at 0° C. lithium borohydride (0.174 ml, 0.354 mmol) was added and the reaction mixture was stirred at room temperature and under nitrogen atmosphere for 3 days. Volatiles were evaporated in vacuo and the residue was dissolved in Methanol (2 ml)/HCl 1 N in water (3 ml). After 1 h stirring combined solvents were evaporated in vacuo. The residue was dissolved in Ethyl acetate (4 ml) and washed with NaHCO3 sat. sol. 2×3 ml. Organic phase was dried and evaporated and the residue was purified by flash chromatography on silica gel using a Biotage SNAP 10 g as column and Dichloromethane/Methanol 95:5 as eluent affording the title compound (39.8 mg, 0.068 mmol, y=57.2%).

H-NMR (500 Mhz) DMSO-$d_6$ δ ppm 7.92 (s, 1H), 7.78 (s, 2H), 7.27 (dd, 1H), 6.84 (dd, 1H), 6.73-6.80 (m, 1H), 5.50 (q, 1H), 4.28 (dd, 1H), 3.36-3.44 (m, 1H), 3.13-3.22 (m, 2H), 2.89-2.95 (m, 1H), 2.40 (s, 3H), 1.94 (s, 3H), 1.87-1.95 (m, 3H), 1.77-1.86 (m, 1H), 1.64-1.72 (m, 1H), 1.55-1.64 (m, 3H), 1.52 (d, 3H), 1.13 (s, 3H).

Dipolar correlation between Me-36 and H-3 eq

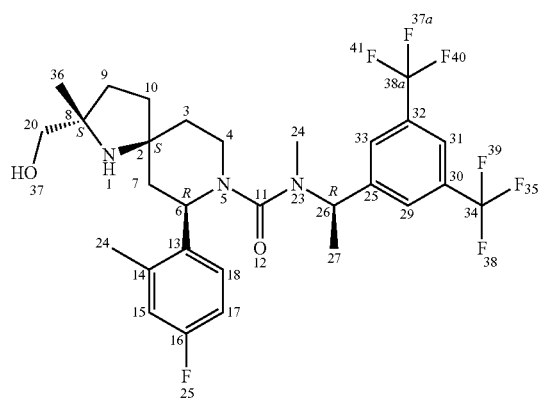

UPLC: Rt 0.72 mins, m/z 590 [M+H]$^+$

Example 20

(2R,5S,7R)-$N^8$-{(1R)-1-[3,5-bis(trifluoromethyl)phenyl]ethyl}-7-(4-fluoro-2-methylphenyl)-$N^8$,2-dimethyl-1,8-diazaspiro[4.5]decane-2,8-dicarboxamide

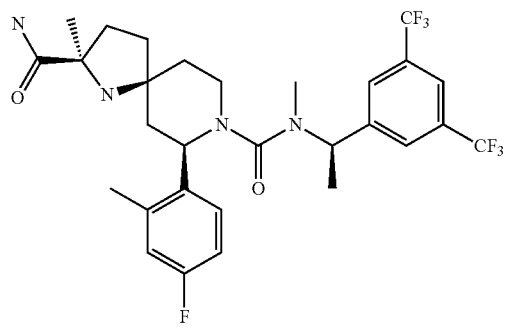 [SMILES: Cc1cc(F)ccc1[C@H]1C[C@@]2(CCN1C(=O)N(C)[C@H](C)c1cc(C(F)(F)F)cc(C(F)(F)F)c1)CC[C@](C)(C(N)=O)N2]

In a sealed tube a solution of methyl (2R,5S,7R)-8-{[{(1R)-1-[3,5-bis(trifluoromethyl)phenyl]ethyl}(methyl)amino]carbonyl}-7-(4-fluoro-2-methylphenyl)-2-methyl-1,8-diazaspiro[4.5]decane-2-carboxylate (Intermediate 44, 70 mg, 0.113 mmol) in 7 N methanolic ammonia (5 mL, 35.0 mmol) was shaken at 40° C. for 5 days by PLS. Volatiles were removed in vacuo and the residue was purified by flash chromatography on silica gel using a SNAP 10 g as column and Dichloromethane/Methanol 98:2 as eluent affording the title compound (38 mg, 0.063 mmol, y=55.7%).

H-NMR (400 Mhz) DMSO-$d_6$ δ ppm 8.01 (s, 1H), 7.70 (s, 2H), 7.49 (d, 1H), 7.17 (dd, 1H), 7.00 (d, 1H), 6.93 (dd, 1H), 6.76-6.83 (m, 1H), 5.32 (q, 1H), 4.19 (dd, 1H), 3.27-3.31 (m, 1H), 2.74-2.81 (m, 1H), 2.74 (s, 3H), 2.42 (bs, 1H), 2.35 (s, 3H), 2.11-2.22 (m, 1H), 1.81 (m, 2H), 1.61-1.72 (m, 3H), 1.54-1.60 (m, 2H), 1.48 (d, 3H), 1.21 (s, 3H).

HPLC: Rt=6.16 mins

Example 21

(2S,5S,7R)-$N^8$-{(1R)-1-[3,5-bis(trifluoromethyl)phenyl]ethyl}-7-(4-fluoro-2-methylphenyl)-$N^8$,2-dimethyl-1,8-diazaspiro[4.5]decane-2,8-dicarboxamide

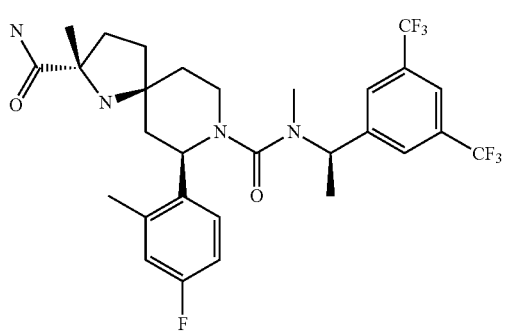 [SMILES: Cc1cc(F)ccc1[C@H]1C[C@@]2(CCN1C(=O)N(C)[C@H](C)c1cc(C(F)(F)F)cc(C(F)(F)F)c1)CC[C@@](C)(C(N)=O)N2]

In a sealed tube a solution of methyl (2S,5S,7R)-8-{[{(1R)-1-[3,5-bis(trifluoromethyl)phenyl]ethyl}(methyl)amino]carbonyl}-7-(4-fluoro-2-methylphenyl)-2-methyl-1,8-diazaspiro[4.5]decane-2-carboxylate (Intermediate 45, 75 mg, 0.121 mmol) in 7 N methanolic ammonia (5 ml, 35.0 mmol) was shaken at 40° C. for 5 days by PLS. Volatiles were removed in vacuo and the residue was purified by flash chromatography on silica gel using a SNAP 10 g as column and Dichloromethane/Methanol 98:2 as eluent affording the title compound (27 mg, 0.45 mmol, y=37.2%).

H-NMR (400 Mhz) DMSO-$d_6$ δ ppm 8.01 (s, 1H), 7.71 (s, 2H), 7.39 (d, 1H), 7.16 (dd, 1H), 6.91 (dd, 1H), 6.86 (d, 1H), 6.75-6.83 (m, 1H), 5.33 (q, 1H), 4.08-4.15 (m, 1H), 3.28-3.31 (m, 1H), 2.77-2.83 (m, 1H), 2.76 (s, 3H), 2.43 (bs, 1H), 2.30 (s, 3H), 2.15 (dd, 1H), 1.74-1.87 (m, 1H), 1.59-1.73 (m, 4H), 1.50-1.57 (m, 2H), 1.48 (d, 3H), 1.26 (s, 3H).

HPLC: Rt=6.18 mins

Example 22

(2R,4S,8a'R)-N-{(1R)-1-[3,5-bis(trifluoromethyl)phenyl]ethyl}-2-(4-fluoro-2-methylphenyl)-N,8a'-dimethylhexahydro-1H-spiro[piperidine-4,6'-pyrrolo[2,1-c][1,4]oxazine]-1-carboxamide

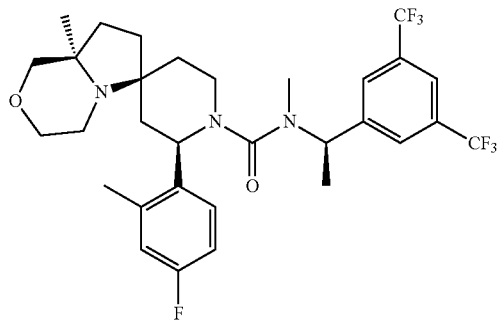 [SMILES: Cc1cc(F)ccc1[C@H]1C[C@@]2(CCN1C(=O)N(C)[C@H](C)c1cc(C(F)(F)F)cc(C(F)(F)F)c1)CC[C@]1(C)COCCN12]

(2R,4S,8a'R)-N-{(1R)-1-[3,5-bis(trifluoromethyl)phenyl]ethyl}-2-(4-fluoro-2-methylphenyl)-3'-hydroxy-N,8a'-dimethylhexahydro-1H-spiro[piperidine-4,6'-pyrrolo[2,1-c][1,4]oxazine]-1-carboxamide (Intermediate 47, 67 mg, 0.106 mmol) was dissolved in Dichloromethane (DCM) (1 ml), Boron trifluoride diethyl etherate (0.016 ml, 0.127 mmol) and triethylsilane (0.068 ml, 0.424 mmol) were added and the reaction mixture was stirred at 100° C. under microwave irradiation for 40 minutes. The mixture was washed with water (3 ml). Organic layer was dried and evaporated in vacuo. The residue was purified by flash chromatography on SPE NH2-cartridge 10 g as column and Cyclohexane/Ethyl acetate 95:5 to Cyclohexane/Ethyl acetate 8:2 as eluent affording the title compound (28.5 mg, 0.046 mmol, y=43.4%).

H-NMR (400 Mhz) DMSO-$d_6$ δ ppm 7.99 (s, 1H), 7.71 (s, 2H), 7.11-7.21 (m, 1H), 6.91 (d, 1H), 6.77 (t, 1H), 5.29-2.43 (m, 1H), 4.10 (d, 1H), 3.70 (d, 1H), 3.55 (d, 1H), 3.24-3.38 (m, 1H), 3.19 (t, 1H), 3.00 (d, 1H), 2.57-2.91 (m, 3H), 2.76 (s, 3H), 2.34 (s, 3H), 1.90-2.03 (m, 1H), 1.79-1.92 (m, 1H), 1.12-1.91 (m, 6H), 1.47 (d, 3H), 1.04 (s, 3H).

HPLC: Rt=6.00 mins, m/z 616 [M+H]$^+$

Example 23

(2R,4S,8a'S)-N-{(1R)-1-[3,5-bis(trifluoromethyl)phenyl]ethyl}-2-(4-fluoro-2-methylphenyl)-N,8a'-dimethylhexahydro-1H-spiro[piperidine-4,6'-pyrrolo[2,1-c][1,4]oxazine]-1-carboxamide

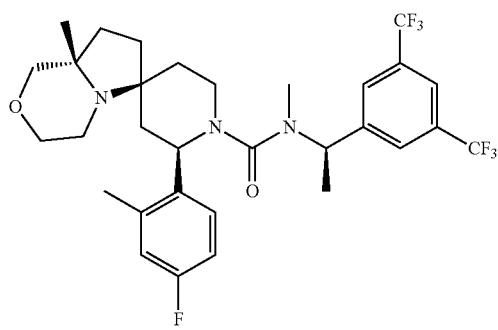 [SMILES: Cc1cc(F)ccc1[C@H]1C[C@@]2(CCN1C(=O)N(C)[C@H](C)c1cc(C(F)(F)F)cc(C(F)(F)F)c1)CC[C@@]1(C)COCCN12]

(2R,4S,8a'S)-N-{(1R)-1-[3,5-bis(trifluoromethyl)phenyl]ethyl}-2-(4-fluoro-2-methylphenyl)-3'-hydroxy-N,8a'-dimethylhexahydro-1H-spiro[piperidine-4,6'-pyrrolo[2,1-c][1,4]oxazine]-1-carboxamide (Intermediate 49, 66 mg, 0.104 mmol) was dissolved in Dichloromethane (DCM) (1 ml), Boron trifluoride diethyl etherate (0.017 ml, 0.136 mmol) and triethylsilane (0.050 ml, 0.313 mmol) were added and mixture was stirred at 100° C. under microwave irradiation for 25 minutes. The mixture was washed with water (3 ml), organic layer was dried and evaporated in vacuo. The residue was purified by flash chromatography on SPE NH2-cartridge 10 g as column and Cyclohexane/Ethyl acetate 9:1 to Cyclohexane/Ethyl acetate 8:2 as eluent affording the title compound (20 mg, 0.032 mmol, y=30.7%).

H-NMR (500 Mhz) DMSO-$d_6$ δ ppm 7.80 (s, 1H), 7.57-7.73 (m, 2H), 7.17 (t, 1H), 6.57-6.77 (m, 2H), 5.35-5.43 (m, 1H), 4.19-4.28 (m, 1H), 3.55-3.61 (m, 1H), 3.42-3.49 (m, 1H), 3.24-3.33 (m, 1H), 3.00-3.12 (m, 1H), 2.84-2.93 (m, 1H), 2.73-2.83 (m, 2H), 2.68 (s, 3H), 2.45-2.55 (m, 1H), 2.31 (s, 3H), 1.85-2.01 (m, 2H), 1.66-1.78 (m, 1H), 1.45-1.61 (m, 3H), 1.41 (d, 3H), 1.32-1.38 (m, 1H), 1.19-1.27 (m, 1H), 1.01 (s, 3H).

UPLC: Rt=0.76 mins, m/z 616 [M+H]$^+$

Example 24

(2R,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide

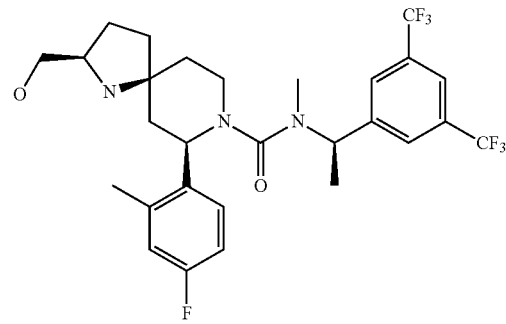 [SMILES: Cc1cc(F)ccc1[C@H]1C[C@]2(CC[C@H](CO)N2)CCN1C(=O)N(C)[C@H](C)c1cc(C(F)(F)F)cc(C(F)(F)F)c1]

To a solution of methyl (2R,5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-2-carboxylate (Intermediate 12, 350 mg, 0.580 mmol) in Tetrahydrofuran (THF) (6 ml) at 0° C. lithium borohydride (0.568 ml, 1.160 mmol) was added and the reaction mixture was stirred at room temperature and under nitrogen atmosphere overnight. Volatiles were evaporated in vacuo and the residue was dissolved in Methanol (2 ml)/HCl 1 N in water (4 ml). After 1 h stirring combined solvents were evaporated in vacuo. The residue was dissolved in Ethyl acetate (4 ml) and washed with NaHCO3 sat. sol. (2×3 ml). Organic phase was dried and evaporated and the residue was purified by flash chromatography on silica gel using a Biotage 12+M as column and Dichloromethane/Methanol 95:5 as eluent affording the title compound (160 mg, 0.278 mmol, y=47.9%).

H-NMR (400 Mhz) DMSO-$d_6$ δ ppm 8.01 (s, 1H), 7.71 (s, 2H), 7.15 (dd, 1H), 6.92 (dd, 1H), 6.75-6.83 (m, 1H), 5.32 (q, 1H), 4.43 (bs, 1H), 4.10-4.21 (m, 1H), 3.21-3.30 (m, 3H), 3.09-3.21 (m, 1H), 2.75-2.84 (m, 1H), 2.75 (s, 3H), 2.34 (s, 3H), 1.70-1.92 (m, 3H), 1.34-1.67 (m, 5H), 1.48 (d, 3H).

HPLC: Rt=6.56 mins; MS: m/z 576 [M+H]$^+$

Example 25

(2R,4S,13a'R)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide

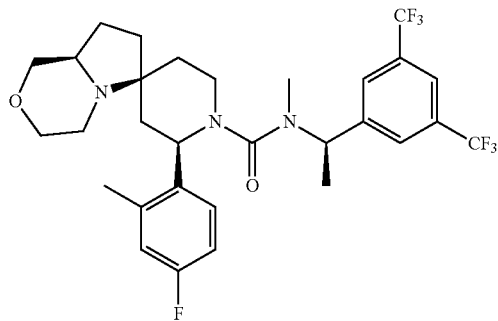

(2R,4S,8a'R)-N-{(1R)-1-[3,5-bis(trifluoromethyl)phenyl]ethyl}-2-(4-fluoro-2-methylphenyl)-3'-hydroxy-N-methylhexahydro-1H-spiro[piperidine-4,6'-pyrrolo[2,1-c][1,4]oxazine]-1-carboxamide (Intermediate 51, 120 mg, 0.194 mmol) was dissolved in Dichloromethane (DCM) (2 ml), boron trifluoride diethyl etherate (0.029 ml, 0.233 mmol) and triethylsilane (0.124 ml, 0.777 mmol) were added and mixture was stirred at 100° C. under microwave irradiation for 50 minutes. The mixture was washed with water (3 ml), organic layer was dried and evaporated in vacuo. The residue was purified by flash chromatography on SPE NH2-cartridge 10 g as column and Cyclohexane/Ethyl acetate 9:1 to Cyclohexane/Ethyl acetate 8:2 as eluent affording the title compound (31 mg, 0.051 mmol, y=26.3%).

H-NMR (400 Mhz) DMSO-$d_6$ δ ppm 8.01 (s, 1H), 7.71 (s, 2H), 7.18 (dd, 1H), 6.93 (dd, 1H), 6.78 (td, 1H), 5.35 (d, 1H), 4.17 (dd, 1H), 3.78-3.92 (m, 1H), 3.73 (d, 1H), 3.19-3.42 (m, 2H), 3.00 (t, 1H), 2.79-2.86 (m, 1H), 2.76 (s, 3H), 2.66-2.75 (m, 1H), 2.51-2.65 (m, 1H), 2.35 (s, 3H), 2.25-2.35 (m, 1H), 1.98 (td, 1H), 1.53-1.90 (m, 4H), 1.48 (d, 3H), 1.09-1.43 (m, 3H).

LC/MS (Acidic gradient conditions): Rt=2.066 mins, m/z 602 [M+H]$^+$

Example 26

(2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide

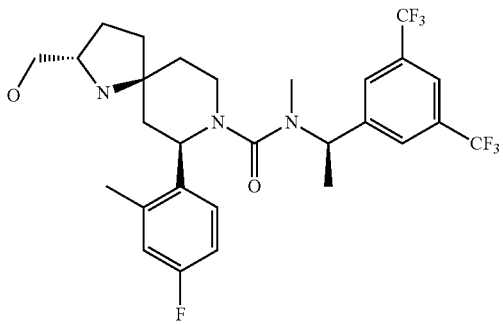 [SMILES: Cc1cc(F)ccc1[C@H]1C[C@]2(CC[C@@H](CO)N2)CCN1C(=O)N(C)[C@H](C)c1cc(C(F)(F)F)cc(C(F)(F)F)c1]

To a solution of methyl (2S,5S,7R)-8-{[{(1R)-1-[3,5-bis(trifluoromethyl)phenyl]ethyl}methyl)amino]carbonyl}-7-(4-fluoro-2-methylphenyl)-1,8-diazaspiro[4.5]decane-2-carboxylate (Intermediate 13, 350 mg, 0.580 mmol) in Tetrahydrofuran (THF) (7 ml) at 0° C. lithium borohydride (0.568 ml, 1.160 mmol) was added and the reaction mixture was stirred at room temperature and under nitrogen atmosphere for 3 days. Volatiles were evaporated in vacuo and the residue was dissolved in Methanol (2 ml)/HCl 1 N in water (3 ml). After 1 h stirring combined solvents were evaporated in vacuo. The residue was dissolved in Ethyl acetate (4 ml) and washed with NaHCO3 sat. sol. (2×3 ml). Organic phase was dried and evaporated and the residue was purified by flash chromatography on silica gel using a Biotage SNAP 10 g as column and Dichloromethane/Methanol 98:2 as eluent affording the title compound (110 mg, 0.191 mmol, y=33.0%).

H-NMR (400 Mhz) DMSO-$d_6$ δ ppm 8.01 (s, 1H), 7.71 (s, 2H), 7.17 (dd, 1H), 6.92 (dd, 1H), 6.74-6.84 (m, 1H), 5.33 (q, 1H), 4.41 (bs, 1H), 4.16 (dd, 1H), 3.31-3.42 (m, 1H), 3.20-3.28 (m, 2H), 3.12-3.21 (m, 1H), 2.76-2.84 (m, 1H), 2.75 (s, 3H), 2.34 (s, 3H), 1.77-1.89 (m, 1H), 1.60-1.77 (m, 4H), 1.49-1.58 (m, 3H), 1.48 (d, 3H).

HPLC: Rt=6.53 mins; MS: m/z 576 [M+H]$^+$

Example 27

(2R,4S,8a'S)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide

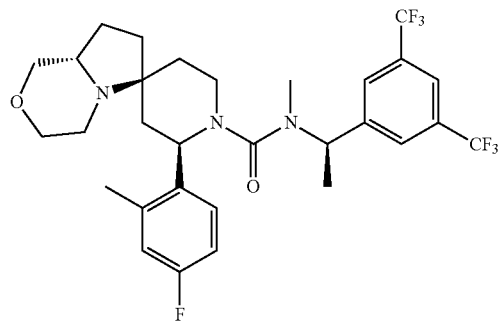 [SMILES: Cc1cc(F)ccc1[C@H]1C[C@]2(CC[C@H]3COCCN32)CCN1C(=O)N(C)[C@H](C)c1cc(C(F)(F)F)cc(C(F)(F)F)c1]

(2R,4S,8a'S)-N-{(1R)-1-[3,5-bis(trifluoromethyl)phenyl]ethyl}-2-(4-fluoro-2-methylphenyl)-3'-hydroxy-N-methylhexahydro-1H-spiro[piperidine-4,6'-pyrrolo[2,1-c][1,4]oxazine]-1-carboxamide (Intermediate 50 115 mg, 0.186 mmol) was dissolved in Dichloromethane (DCM) (2 ml), Boron trifluoride diethyl etherate (0.022 ml, 0.223 mmol) and triethylsilane (0.119 ml, 0.745 mmol) were added and mixture was stirred at 100° C. under microwave irradiation for 50 minutes. The mixture was washed with water (3 ml), organic layer was dried and evaporated in vacuo. The residue was purified by flash chromatography on SPE NH2-cartridge 10 g as column and Cyclohexane/Ethyl acetate 9:1 to Cyclohexane/Ethyl acetate 8:2 as eluent affording the title compound (21 mg, 0.035 mmol, y=26.3%).

H-NMR (400 Mhz) DMSO-$d_6$ δ ppm 8.01 (s, 1H), 7.71 (s, 2H), 7.20 (dd, 1H), 6.92 (dd, 1H), 6.68-6.84 (m, 1H), 5.36 (q, 1H), 4.19 (dd, 1H), 3.86 (dd, 1H), 3.74 (d, 1H), 3.33-3.46 (m, 1H), 3.15-3.28 (m, 1H), 2.99 (t, 1H), 2.81 (1H), 2.75 (s, 3H), 2.66-2.75 (m, 1H), 2.53-2.66 (m, 1H), 2.39-2.50 (m, 1H), 2.34 (s, 3H), 1.57-1.89 (m, 5H), 1.44-1.55 (m, 1H), 1.49 (d, 3H), 1.09-1.35 (m, 2H).

UPLC: Rt=0.70 mins, m/z 602 [M+H]$^+$

Formation of Hydrochloride Salt (Summarized in the Table 1)
General Procedure:

To a solution of free base in diethyl ether was added HCl 1N in diethyl ether (1.1-2.0 eq).

The solvent was removed under vacuum and the residue was triturated in diethyl ether or n-pentane to afford the corresponding hydrochloride salt.

TABLE 1

| Example | Structure | Chemical name | Analytical data | Free base Example |
|---|---|---|---|---|
| 28 | 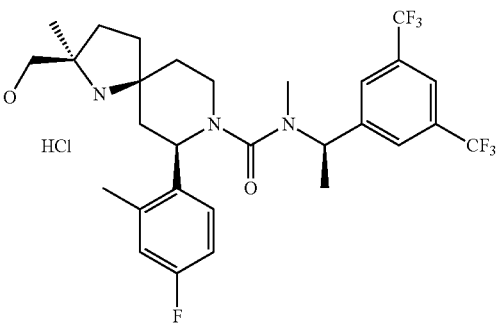 [SMILES: Cc1cc(F)ccc1[C@H]1C[C@@]2(CCN1C(=O)N(C)[C@H](C)c1cc(C(F)(F)F)cc(C(F)(F)F)c1)CC[C@](C)(CO)N2 ; Cl] | (2R,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide hydrochloride | HPLC: Rt = 6.39 mins MS: m/z 590 [M(free base) + H]+ | 18 |
| 29 | 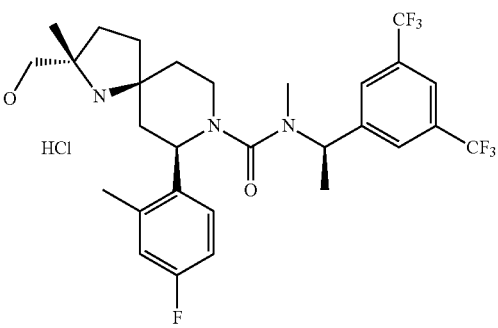 [SMILES: Cc1cc(F)ccc1[C@H]1C[C@@]2(CCN1C(=O)N(C)[C@H](C)c1cc(C(F)(F)F)cc(C(F)(F)F)c1)CC[C@@](C)(CO)N2 ; Cl] | (2S,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide hydrochloride | HPLC: Rt = 6.37 mins MS: m/z 590 [M(free base) + H]+ | 19 |
| 30 | 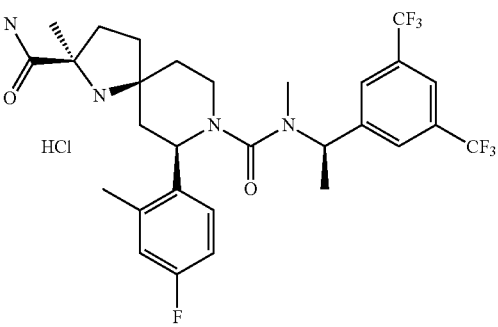 [SMILES: Cc1cc(F)ccc1[C@H]1C[C@@]2(CCN1C(=O)N(C)[C@H](C)c1cc(C(F)(F)F)cc(C(F)(F)F)c1)CC[C@](C)(C(N)=O)N2 ; Cl] | (2R,5S,7R)-N~8~-{(1R)-1-[3,5-bis(trifluoromethyl)phenyl]ethyl}-7-(4-fluoro-2-methylphenyl)-N~8~,2-dimethyl-1,8-diazaspiro[4.5]decane-2,8-dicarboxamide hydrochloride | HPLC: Rt = 6.24 mins MS: m/z 603 [M(free base) + H]+ | 20 |
| 31 | 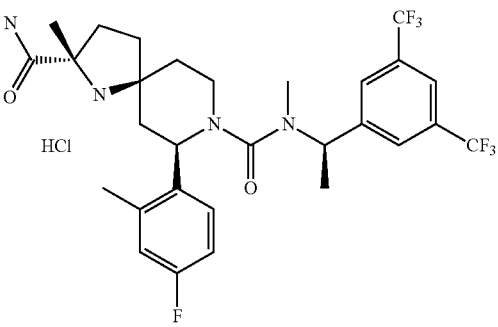 [SMILES: Cc1cc(F)ccc1[C@H]1C[C@@]2(CCN1C(=O)N(C)[C@H](C)c1cc(C(F)(F)F)cc(C(F)(F)F)c1)CC[C@@](C)(C(N)=O)N2 ; Cl] | (2S,5S,7R)-N~8~-{(1R)-1-[3,5-bis(trifluoromethyl)phenyl]ethyl}-7-(4-fluoro-2-methylphenyl)-N~8~,2-dimethyl-1,8-diazaspiro[4.5]decane-2,8-dicarboxamide Hydrochloride | HPLC: Rt = 6.24 mins MS: m/z 603 [M(free base) + H]+ | 21 |

TABLE 1-continued

| Example | Structure | Chemical name | Analytical data | Free base Example |
|---|---|---|---|---|
| 32 | 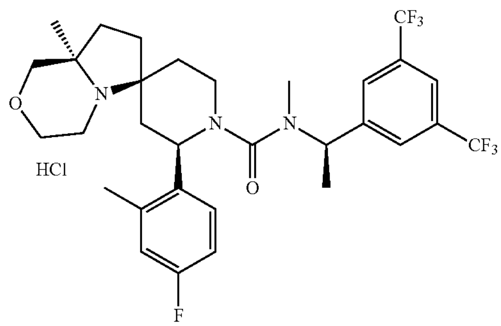 [SMILES: Cc1cc(F)ccc1[C@H]1C[C@@]2(CCN1C(=O)N(C)[C@H](C)c1cc(C(F)(F)F)cc(C(F)(F)F)c1)CC[C@]1(C)COCCN12 ; Cl] | (2R,4S,8a'R)-N-{(1R)-1-[3,5-bis(trifluoromethyl)phenyl]ethyl}-2-(4-fluoro-2-methylphenyl)-N,8a'-dimethylhexahydro-1H-spiro[piperidine-4,6'-pyrrolo[2,1-c][1,4]oxazine]-1-carboxamide hydrochloride. | UPLC: Rt 0.78 mins, m/z 616 [M(free base) + H]+ | 22 |
| 33 | 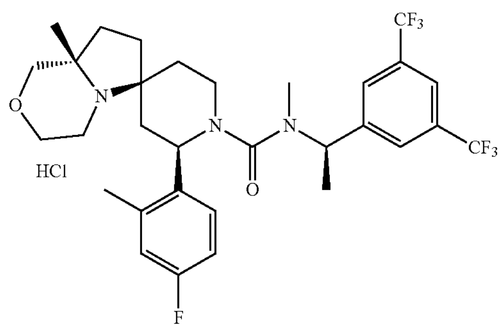 [SMILES: Cc1cc(F)ccc1[C@H]1C[C@@]2(CCN1C(=O)N(C)[C@H](C)c1cc(C(F)(F)F)cc(C(F)(F)F)c1)CC[C@@]1(C)COCCN12 ; Cl] | (2R,4S,8a'S)-N-{(1R)-1-[3,5-bis(trifluoromethyl)phenyl]ethyl}-2-(4-fluoro-2-methylphenyl)-N,8a'-dimethylhexahydro-1H-spiro[piperidine-4,6'-pyrrolo[2,1-c][1,4]oxazine]-1-carboxamide hydrochloride | HPLC: Rt = 5.42 mins MS: m/z 616 [M(free base) + H]+ | 23 |
| 34 | 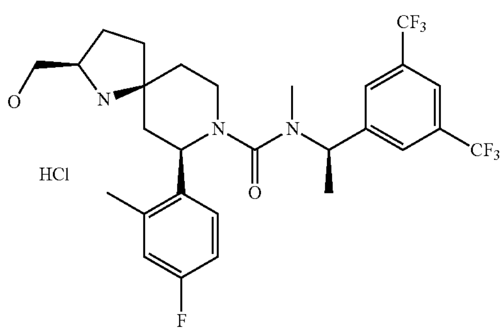 [SMILES: Cc1cc(F)ccc1[C@H]1C[C@]2(CC[C@H](CO)N2)CCN1C(=O)N(C)[C@H](C)c1cc(C(F)(F)F)cc(C(F)(F)F)c1 ; Cl] | (2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide hydrochloride | H-NMR (400 Mhz) DMSO-d6 δ ppm 9.21-9.40 (m, 1H), 8.61-8.76 (m, 1H), 8.01 (s, 1H), 7.71 (s, 2H), 7.18 (dd, 1H), 6.97 (dd, 1H), 6.79-6.91 (m, 1H), 5.29 (q, 1H), 4.23 (dd, 1H), 3.67-3.75 (m, 1H), 3.56-3.69 (m, 2H), 3.38-3.45 (m, 1H), 2.79-2.93 (m, 1H), 2.77 (s, 3H), 2.37 (s, 3H), 1.69-2.24 (m, 8H), 1.48 (d, 3H). HPLC: Rt = 6.64 mins MS: m/z 576 [M(free base) + H]+ | 24 |
| 35 | 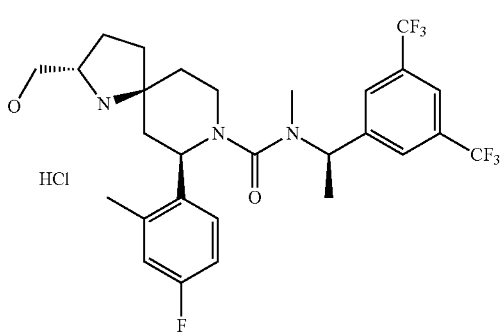 [SMILES: Cc1cc(F)ccc1[C@H]1C[C@]2(CC[C@@H](CO)N2)CCN1C(=O)N(C)[C@H](C)c1cc(C(F)(F)F)cc(C(F)(F)F)c1 ; Cl] | (2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide hydrochloride | H-NMR (400 Mhz) DMSO-d6 δ ppm 9.27-9.40 (m, 1H), 8.44-8.56 (m, 1H), 8.02 (s, 1H), 7.71 (s, 2H), 7.19 (dd, 1H), 6.96 (dd, 1H), 6.82-6.90 (m, 1H), 5.30 (q, 1H), 4.18-4.25 (m, 1H), 3.70 (bs, 1H), 3.60-3.70 (m, 1H), 3.53-3.62 (m, 1H), 3.35-3.52 (m, 1H), 2.85-2.96 (m, 1H), 2.77 (s, 3H), 2.35 (s, 3H), 1.87-2.22 (m, 7H), 1.74-1.87 (m, 1H), 1.47 (d, 3H). HPLC: Rt = 6.57 mins MS: m/z 576 [M(free base) + H]+ | 26 |

TABLE 1-continued

| Example | Structure | Chemical name | Analytical data | Free base Example |
|---|---|---|---|---|
| 36 | 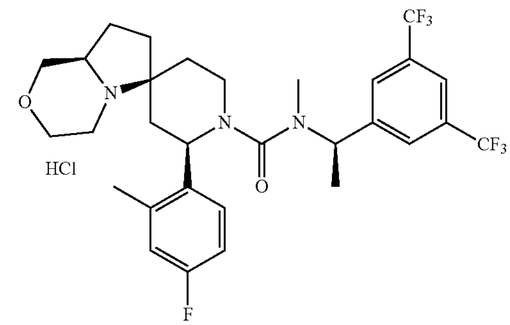 [SMILES: Cc1cc(F)ccc1[C@H]1C[C@]2(CC[C@@H]3COCCN32)CCN1C(=O)N(C)[C@H](C)c1cc(C(F)(F)F)cc(C(F)(F)F)c1 ; Cl] | (2R,4S,8a'R)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide hydrochloride | LC/MS (Acidic gradient conditions): Rt = 2.014 mins, m/z 602 [M(free base) + H]+ | 25 |
| 37 | 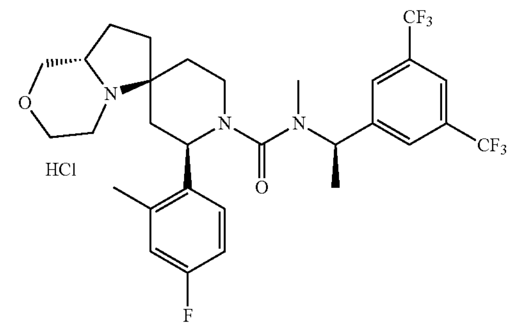 [SMILES: Cc1cc(F)ccc1[C@H]1C[C@]2(CC[C@H]3COCCN32)CCN1C(=O)N(C)[C@H](C)c1cc(C(F)(F)F)cc(C(F)(F)F)c1 ; Cl] | (2R,4S,8a'S)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide hydrochloride | UPLC: Rt 0.70 mins, m/z 602 [M(free base) + H]+ | 27 |

Biological Data

Compounds of the invention may be tested for in vitro biological activity in accordance with the following assays:

A) Measurement of NK Binding Affinity

The NK1 binding affinity of the compounds of the invention was determined using the following filtration binding assay using [$^3$H]-GR205171 as radioligand for human NK1 receptor stably expressed in CHO (Chinese Hamster Ovary) cells (see C. Griffante et al, Br. J. Pharmacol. 2006, 148, 39-45; H. M. Sarau et al, J. Pharmacol. Experimental Therapeutics 2000, 295(1), 373-381 and D. T. Beattie et al., Br. J. Pharmacol. 1995, 116, 3149-3157).

CHO cells stably expressing the human cloned neurokinin NK1 receptor were cultured in Dulbecco's Modified Eagle's Medium/F12 Ham (DMEM/F12Ham) supplemented with 10% foetal bovine serum and 2 mM L-glutamine. Cells were maintained in 5% $CO_2$ in a humidified incubator at 37° C. Cells were harvested at confluency with PBS/EDTA (5 mM) and then pelleted by centrifugation (1000 g, 8 min, 4° C.). To prepare membranes, cell pellets were homogenised in 10 volumes of membrane preparation buffer and centrifuged (48,000 g, 20 min, 4° C.). The membranes were then re-suspended as 500 μL aliquots and stored at −80° C. until use.

Binding assay was carried out in 96 deep well polypropylene plates (Whatman) in a volume of 400 μl consisted of 100 μl of incubation buffer (containing 50 mM HEPES, pH 7.4, 3 mM $MnCl_2$, and 0.02% BSA), 4 μl of DMSO (total binding) or increasing concentrations of the compounds in the invention dissolved in DMSO (1 pM-1 μM final concentration), 100 μl of the radioligand [$^3$H]-GR205171 (0.2 nM final concentration) in incubation buffer and 200 μl of human NK1-CHO cell membranes suspension (4 μg/ml final) in incubation buffer. Non specific binding was defined by the addition of 1 μM unlabelled GR205171. The incubation proceeded at room temperature for 60 minutes. The reaction was stopped by rapid filtration through GF/C filterplates pre-soaked in 0.5% polyetylenimmine (PEI) followed by 3 washes with 1 ml ice cold 0.9% NaCl using a Cell Harvester (Perkin-Elmer). Filterplates were dried and retained radioactivity was counted in a Top Count (Perkin-Elmer).

Specific binding was determined by subtracting total binding from nonspecific binding, which was assessed as the binding in the presence of 1 μM GR205171. Percent inhibition of specific binding was determined for each concentration of the compounds of the invention and the $IC_{50}$, defined as the concentration required inhibiting 50% of the specific binding, obtained from concentration-response curves.

The affinity value was expressed as negative logarithm of the inhibition constant (pKi,) and was calculated from the $IC_{50}$ by the Cheng-Prusoff equation using the dissociation constant ($K_D$) of the radioligand and its concentration in the assay.

B) Measurement of NK Functional Potency:

Compounds of the invention were further characterised in a functional assay using FLIPR technology for the determination of their effect to inhibit the intracellular calcium release induced by interaction of NK receptors with its perspective ligands. Human U2OS cells transiently transduced with recombinant BacMam virus expressing human NK1, NK2 and NK3 receptors were used in the studies (see J. P. Condreay et al, Proc. Natl. Acad. Sci. USA 1999, 96(1): 127-132). Briefly, U2OS cells were harvested from tissue culture flasks, re-suspended to a cell density of 200-300K/ml and mixed with recombinant BacMam virus carrying NKR gene in a virus/cell ratio of 1% (v/v). 10K-15K cells/well were then seeded in 384-well Greiner bio-one plate in culture medium (DMEM with 10% FBS), incubated overnight in 5% $CO_2$ at 37° C. After aspirating the medium, cells were loaded 18-24 hr later with cytoplasmic calcium indicator Fluo-4 Calcium 3 dye (Molecular Devices Co.) in 30 uL/well buffer (Hank's balanced salts with 20 mM Hepes) and incubated in $CO_2$ at 37° C. for 60 minutes. 10 uL/well assay buffer (Hank's balanced salts with 20 mM Hepes) containing different concentrations of compounds were then added to the cells for 30 minutes incubation at 37° C. Finally, 10 uL/well of NKR ligands in assay buffer containing 0.1% BSA was added to the cells and fluorescence signal read on a FLIPR system. Substance P, NKA and NKB peptides were used as the ligands for NK1, NK2 and NK3 receptor, respectively. IC50 values of each compound were determined by an 11-point 3×-dilution inhibition curve. The potency each antagonist (fpK$_i$) was calculated from pIC50 by the Cheng-Prusoff equation using EC50 of ligand determined in a separate experiment.

Results

The compounds of Examples 1, 2, 4, 6, 7, 9, 11, 13, 15, 16, 17 and from 28 to 37 were tested in the NK1 functional assay (B) and exhibited binding potency >9.0 pK$_i$.

The ability of the compounds of the invention to penetrate the central nervous system and to bind at the NK, receptor may be determined using the gerbill foot tapping model as described by Rupniak & Williams, Eur. Jour. of Pharmacol., 1994.

Intracerebroventricular (icy) administration of the NK$_1$ receptor agonist GR73632 (R. M. Hagan et al., Neuropeptides 1991, 19 (2), 127-135) a characteristic hind leg foot tapping (GFT) response in gerbils which can be inhibited by potent NK$_1$ receptor antagonists. The gerbil foot tapping paradigm was carried out as follows; gerbils were dosed with compound of the invention, and following an appropriate pre-treatment time were anaesthetised using isofluorane/oxygen mixture. The skull was then exposed and 5 ul of GR73632 (3 pmol conc.) was injected by insertion of a cuffed 25 G needle to a depth of 4 mm below bregma, directly into the lateral ventricle (intracerebroventricular dosing). Immediately following the injection, gerbils were placed individually into a clear observation box to recover.

Upon the gerbil regaining its righting reflex, the duration of repetitive hind foot tapping was recorded over a 5 minute period. The dose of the test compound required to inhibit by 50% the tapping induced by the NK1 agonist expressed as mg/kg is referred to as the ID$_{50}$ values.

GR73632-induced Foot Tapping behaviour was significantly attenuated by Example 4 over a dose range of 0.1 to 10 mg/kg p.o. with a calculated ID$_{50}$ of approximately 0.67 mg/kg.

What is claimed is:

1. A method for the treatment of insomnia and/or circadian rhythm sleep disorders in mammals, which comprises administering to the sufferer a therapeutically effective amount of a compound of formula (I):

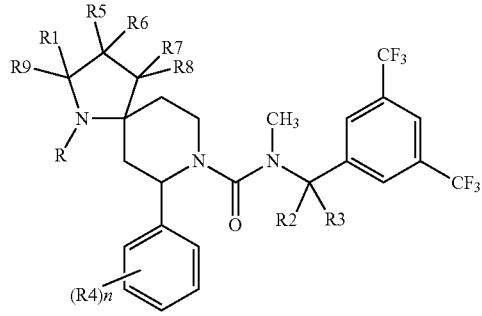

wherein
R is hydrogen or $C_{1-4}$ alkyl;
R$_1$ is hydrogen, $C_{1-4}$ alkyl, C(O)OH, C(O)NH$_2$ or (C$_{1-4}$ alkylene)R$_{10}$;
R$_2$ and R$_3$ are independently hydrogen, $C_{1-4}$ alkyl or R$_2$ together with R$_3$ and together with the carbon atom to which they are attached form a C$_{3-8}$ cycloalkyl group;
R$_4$ is $C_{1-4}$ alkyl, $C_{1-4}$ alkoxy or halogen;
R$_5$ and R$_7$ are independently hydrogen, hydroxy, halogen, C(O)NH$_2$, C(O)OH or (C$_{1-4}$ alkylene) R$_{10}$;
R$_6$ and R$_8$ are independently hydrogen or halogen;
R$_9$ is hydrogen, (C$_{1-4}$ alkylene)R$_{10}$, C(O)NH$_2$, C(O)OH or R$_9$ together with R form a 6 membered heterocyclic ring optionally containing a further heteroatom selected from oxygen, sulphur or nitrogen;
R$_{10}$ is hydrogen, halogen, hydroxy, C(O)NH$_2$, C(O)NH (C$_{1-4}$ alkyl), C(O)N(C$_{1-4}$ alkyl)$_2$ or C(O)OH;
n is 0, 1 or 2:
or a pharmaceutically acceptable salt thereof.

2. The method according to claim 1, wherein the compound of formula (I) is selected from:
(5R,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (diastereoisomer 1);
(5R,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide (diastereoisomer 2);
(2S,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;
(2S,5S,7R)-N$^8$-{(1R)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;
(2S,5S,7R)-N$^8$-{[3,5-bis(trifluoromethyl)phenyl]ethyl}-7-(4-fluoro-2-methylphenyl)-N$^8$-methyl-1,8-diazaspiro[4.5]decane-2,8-dicarboxamide;
(2S,5S,7R)-N$^8$-{[3,5-bis(trifluoromethyl)phenyl]ethyl}-7-(4-fluoro-2-methylphenyl)-N$^8$-methyl-1,8-diazaspiro[4.5]decane-2,8-dicarboxamide;
(2S,5S,7R)-N$^8$-{(1S)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;
(2S,5S,7R)-N$^8$-{(1S)-1-[3,5-bis(trifluoromethyl)phenyl]ethyl}-7-(4-fluoro-2-methylphenyl)-N$^8$-methyl-1,8-diazaspiro[4.5]decane-2,8-dicarboxamide;
sodium(5S,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-3-carboxylate;
lithium(4S,5R,7R)-8-{[{(1R)-1-[3,5-bis(trifluoromethyl)phenyl]ethyl}(methyl)amino]carbonyl}-7-(4-fluoro-2-methylphenyl)-1,8-diazaspiro[4.5]decane-4-carboxylate;
(5S,7R)-N-{(1R)-1-[3,5-bis(trifluoromethyl)phenyl]ethyl}-7-(4-fluoro-2-methylphenyl)-N-methyl-1,8-diazaspiro[4.5]decane-8-carboxamide;
(2R,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide;
(2S,5S,7R)-N-{(1R)-1-[3,5-bis(trifluoromethyl)phenyl]ethyl}-7-(4-fluoro-2-methylphenyl)-2-(hydroxymethyl)-N,2-dimethyl-1,8-diazaspiro[4.5]decane-8-carboxamide;
(2S,5S,7R)-N$^8$-{(1R)-1-[3,5-bis(trifluoromethyl)phenyl]ethyl}-7-(4-fluoro-2-methylphenyl)-N$^8$,2-dimethyl-1,8-diazaspiro[4.5]decane-2,8-dicarboxamide;
(2S,5S,7R)-N$^8$-{(1R)-1-[3,5-bis(trifluoromethyl)phenyl]ethyl}-7-(4-fluoro-2-methylphenyl)-N$^8$,2-dimethyl-1,8-diazaspiro[4.5]decane-2,8-dicarboxamide;

(2S,4S,8a'R)-N-{(1R)-1-[3,5-bis(trifluoromethyl)phenyl]ethyl}-2-(4-fluoro-2-methylphenyl)-N,8a'-dimethyl-hexahydro-1H-spiro[piperidine-4,6'-pyrrolo[2,1-c][1,4]oxazine]-1-carboxamide;

(2S,4S,8a'S)-N-{(1R)-1-[3,5-bis(trifluoromethyl)phenyl]ethyl}-2-(4-fluoro-2-methylphenyl)-N,8a'-dimethyl-hexahydro-1H-spiro[piperidine-4,6'-pyrrolo[2,1-c][1,4]oxazine]-1-carboxamide;

(2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide;

(2S,4S,8a'R)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide;

(2S,5S,7R)-N-{(1R)-1-[3,5-bis(trifluoromethyl)phenyl]ethyl}-7-(4-fluoro-2-methylphenyl)-2-(hydroxymethyl)-N-methyl-1,8-diazaspiro[4.5]decane-8-carboxamide;

(2S,4S,8a'S)-N-{(1R)-1-[3,5-bis(trifluoromethyl)phenyl]ethyl}-2-(4-fluoro-2-methylphenyl)-N-methylhexahydro-1H-spiro[piperidine-4,6'-pyrrolo[2,1-c][1,4]oxazine]-1-carboxamide;

or a pharmaceutically acceptable salt thereof.

3. The method according to claim 1, wherein the compound of formula (I) is (2R,5S,7R)-$N^8$-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide

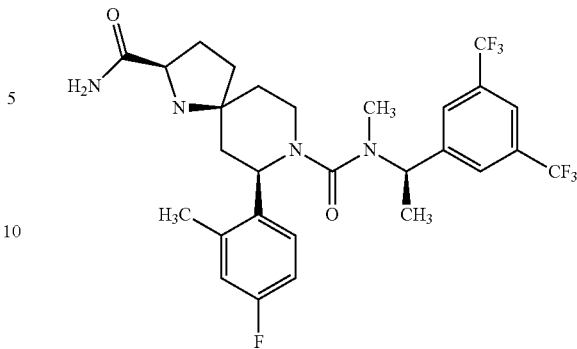

or a pharmaceutically acceptable salt thereof.

4. The method according to claim 1, wherein the compound of formula (I) is (2R,5S,7R)-$N^8$-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide.

5. The method according to claim 1, wherein the compound of formula (I) is (2R,5S,7R)-$N^8$-{(1R)-1-[3,5-bis(trifluoromethyl)phenyl]ethyl}-7-(4-fluoro-2-methylphenyl)-$N^8$-methyl-1,8-diazaspiro[4.5]decane-2,8-dicarboxamide hydrochloride.

6. The method according to claim 1, wherein said mammal is a human.

* * * * *